(12) United States Patent
Fischer et al.

(10) Patent No.: US 6,825,325 B1
(45) Date of Patent: Nov. 30, 2004

(54) MOLECULAR PATHOGENICIDE MEDIATED PLANT DISEASE RESISTANCE

(75) Inventors: Rainer Fischer, Aachen (DE); Stefan Schillberg, Aachen (DE); Jörg Nähring, Aachen (DE); Markus Sack, Aachen (DE); Michael Monecke, Aachen (DE); Yu-Cai Liao, Aachen (DE); Holger Spiegel, Aachen (DE); Sabine Zimmerman, Aachen (DE); Neil Emans, Thimister-Clermont (BE)

(73) Assignee: Fraunhofer Gesellschaft zur Forderung der angewandten Forschung e.V., Munich (DE)

( * ) Notice: Subject to any disclaimer, the term of this patent is extended or adjusted under 35 U.S.C. 154(b) by 0 days.

(21) Appl. No.: 09/419,788

(22) Filed: Oct. 18, 1999

(30) Foreign Application Priority Data

Oct. 16, 1998 (EP) .............................. 98119630
Oct. 16, 1998 (IN) ..................... 666/BOM/98

(51) Int. Cl.$^7$ ................................ C12P 21/08
(52) U.S. Cl. ................. 530/388.2; 530/388.3; 530/388.4; 530/388.5; 530/388.6; 530/387.3
(58) Field of Search .......................... 530/388.2, 388.5, 530/388.3, 388.4, 388.6, 387.3

(56) References Cited

U.S. PATENT DOCUMENTS 5,374,548 A * 12/1994 Caras
5,698,679 A * 12/1997 Nemazee
5,876,950 A * 3/1999 Siadak et al.

FOREIGN PATENT DOCUMENTS

WO    WO 96/09398    * 3/1996

* cited by examiner

*Primary Examiner*—Patrick J. Nolan
(74) *Attorney, Agent, or Firm*—Birch, Stewart, Kolasch & Birch, LLP

(57) ABSTRACT

The present invention is drawn to a fusion protein containing at least one binding domain that specifically recognizes an eptitope of a plant pathogen and at least one additional domain made from a protein or peptide sequence which is toxic to the pathogen or detrimental the replication, transmission or life cycle of the pathogen. The present invention is further drawn to a pathogenocide made from the binding domain, a cellular targeting sequence and/or membrane localization sequence that leads to membrane anchoring. The present invention is further drawn to nucleotide sequences encoding fusion proteins and pathogenocides and to vectors containing the nucleotide sequences; as well as methods of making the fusion proteins and pathogencides and methods of making pathogen resistant plants, plant cells, or plant tissues with the fusion proteins and pathogenocides.

25 Claims, 26 Drawing Sheets

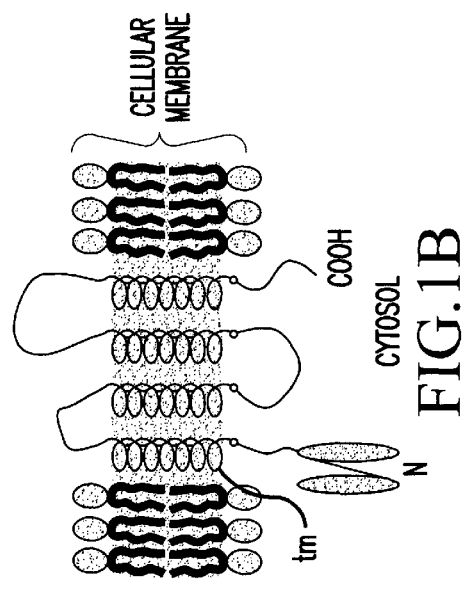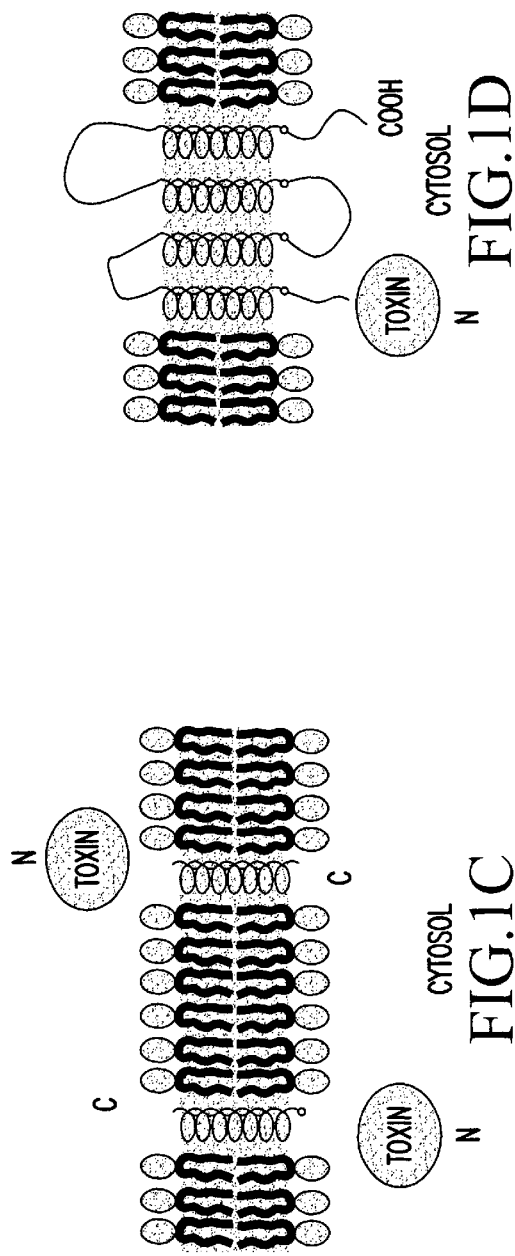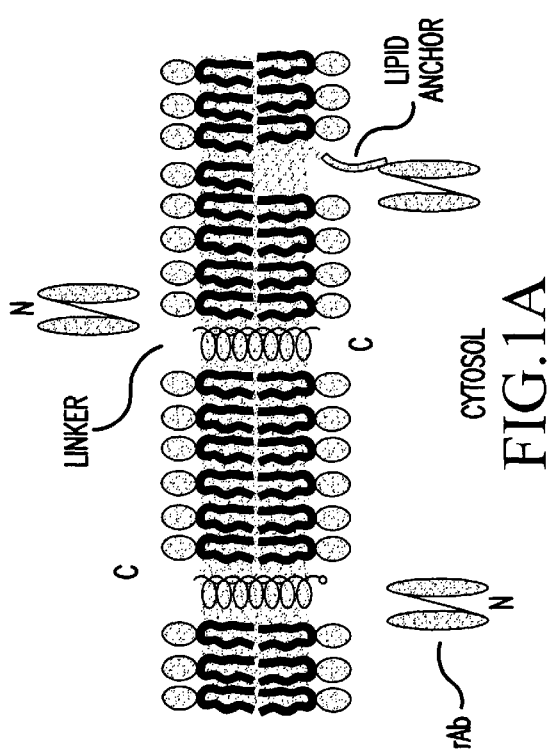

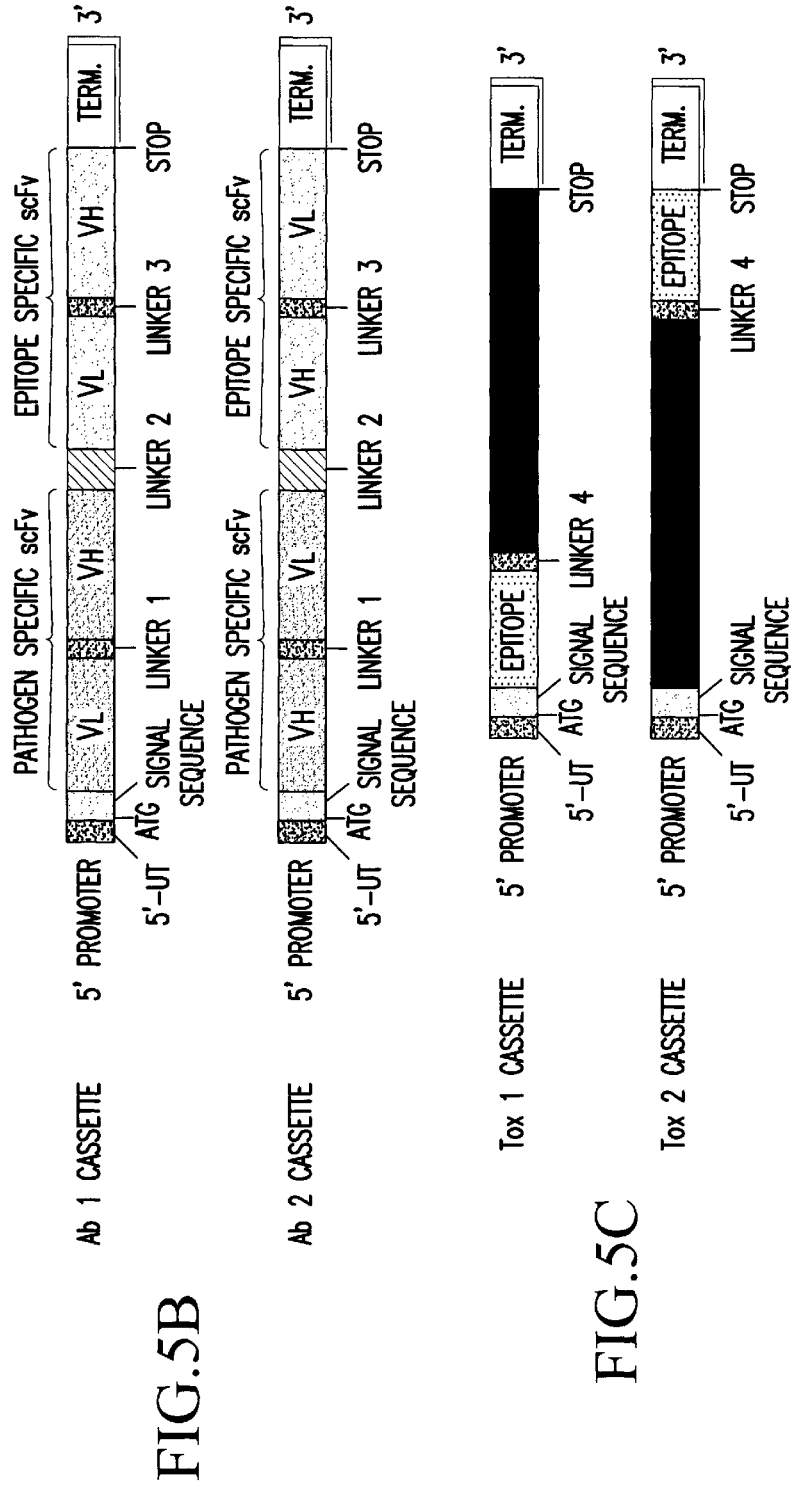

| | | | | | |
|---|---|---|---|---|---|
| scFv24 | MQIVLTQSPA | IMSASPGEKV | TMTC SASSSV | SKMQ WYQQKS | GTSPKRWIY D |
| | Framework I | | CDR LI | | Framework II |
| scFv24 | TSKLAS GVPG | RFSGSGSGTS | YSLTISSMEA | EDAATYYC QQ | WSSNPLT FGA |
| | CDR LII | | Framework III | | CDR LIII |
| scFv24 | GTKLEI KGST | SGSGKSSEGK | GE VQLQQSGP | ELVNPGASVK | MSCKASGYTF |
| | Framework IV | Linker 212 | | Framework I | |
| scFv24 | ITYVMH WVKQ | KPGQGLEWIG | YINPNKDGTK | FNEKFKG KAT | LTSDKSSNTA |
| | CDR LI | Framework II | CDR LII | | Framework III |
| scFv24 | YMELSSLTSE | DSAVYYCAR D | YDYDWFAY WG | QGTLVTVSAV | D GGGS MKRML |
| | Framework III | | CDR LIII | Framework IV | Linker RNAse |
| RnaseE | INATQQEELR | VALVDGQRLY | DLDIESPGHE | QKKANIYKGK | ITRIEPSLEA |
| | E. coli RNAse E gene ---> | | | | |
| RnaseE | AFVDYGAERH | GFLPLKEIAR | EYFPANYSAH | GRPNIKDVLR | EGQEVIVQID |
| RnaseE | KEERGNKGAA | LTTFISLAGS | YLVLMPNNPR | AGGISRRIEG | DDRTELKEAL |
| RnaseE | ASLELPEGMG | LIVRTAGVGK | SAEALQWDLS | FRLKHWEAIK | KAAESRPAPF |
| RnaseE | LIHQESNVIV | RAFRDYLRQD | IGEILIDNPK | VLELARQHIA | ALGRPDFSSK |
| RnaseE | IKLYTGEIPL | FSHYQIESQI | ESAFQREVRL | PSGGSIVIDS | TEALTAIDIN |
| RnaseE | SARATRGGDI | EETAFNTNLE | AADEIARQLR | LRDLGGLIVI | DFIDMTPVRH |
| RnaseE | QRAVENRLRE | AVRQDRARIQ | ISHISRFGLL | EMSRHRLSPS | LGESSHHVCP |
| RnaseE | RCSGTGTVRD | NESLSLSILR | LIEEEALKEN | TQEVHAIVPV | PIASYLLNEK |
| RnaseE | RSAVNAIETR | QDGVRCVIVP | NDQMETPHYH | VVRVRKGEET | PTLSYMLPKL |
| RnaseE | HEEAMALPSE | EEFAERKRPE | QPALATFAMP | DVPPAPTPAE | PAAPVVAPAP |
| RnaseE | KAAPATPAAP | AQPGLLSRFF | GALKALFSGG | EETKPTEQPA | PKAEAKPERQ |
| RnaseE | QDRRKPRQNN | RRDRNERRDT | RSERTEGSDN | REENRRNRRQ | AQQQTAETRE |
| RnaseE | SRQQAEVTEK | ARTADEQQAP | RRERSRRRND | DKRQAQQEAK | ALNVEEQSVQ |
| RnaseE | ETEQEERVRP | VQPRRKQRQL | NQKVRYEQSV | AEEAVVAPVV | EETVAAEPIV |
| RnaseE | QEAPAPRTEL | VKVPLPVVAQ | TAPEQQEENN | ADNRDNGGMP | SFSPLASSPA |
| RnaseE | RKWSASSSLS | | | | |

FIG. 14

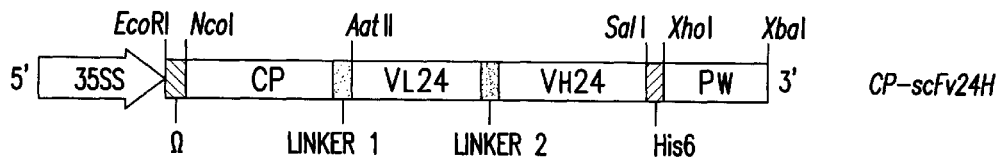
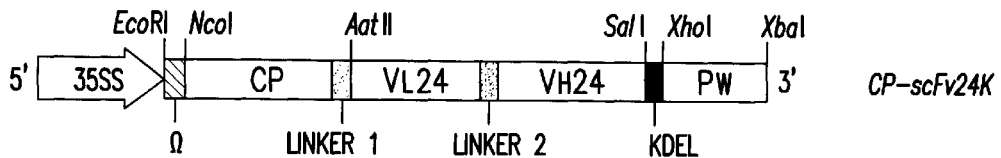
FIG.15A
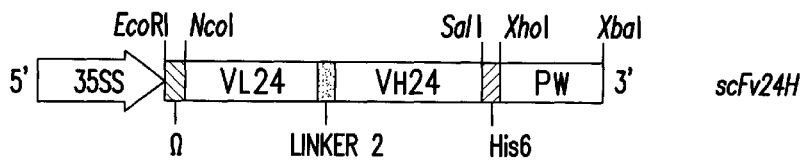
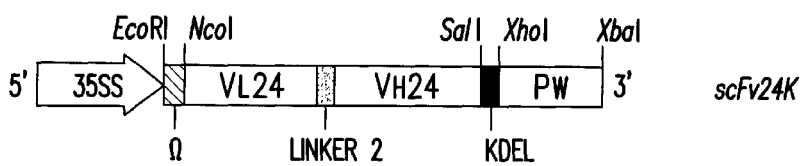
FIG.15B
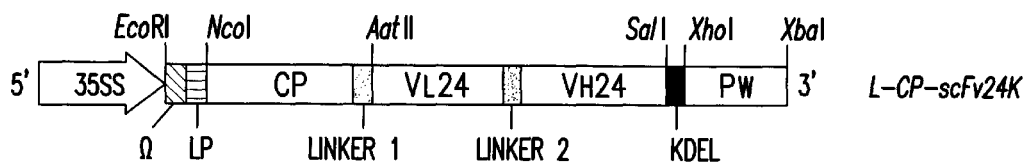
FIG.15C
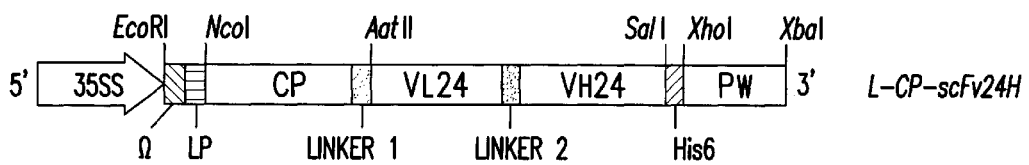
FIG.15D

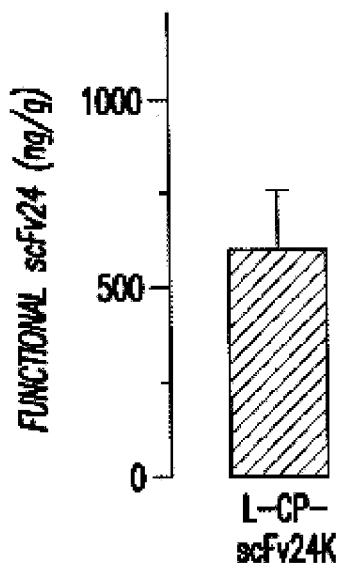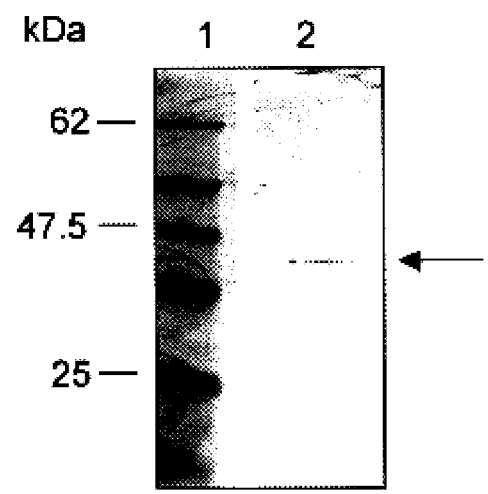
FIG.16  FIG.17
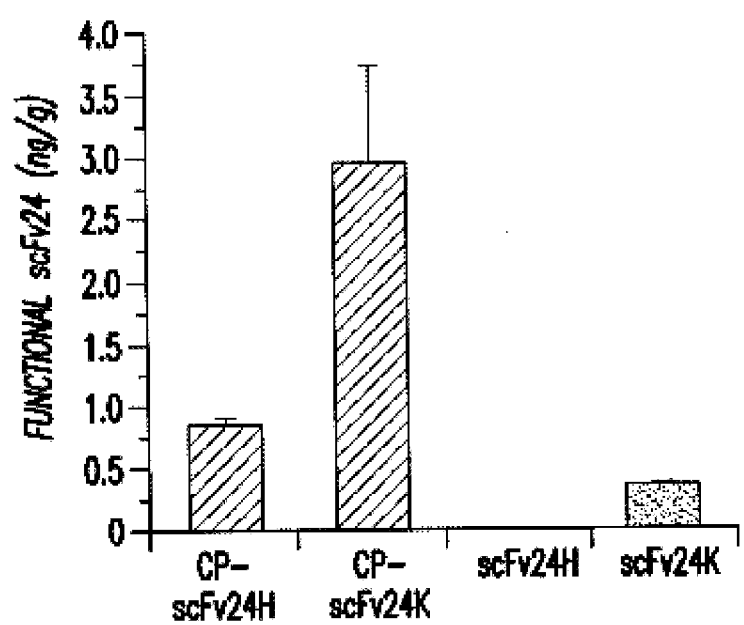
FIG.18

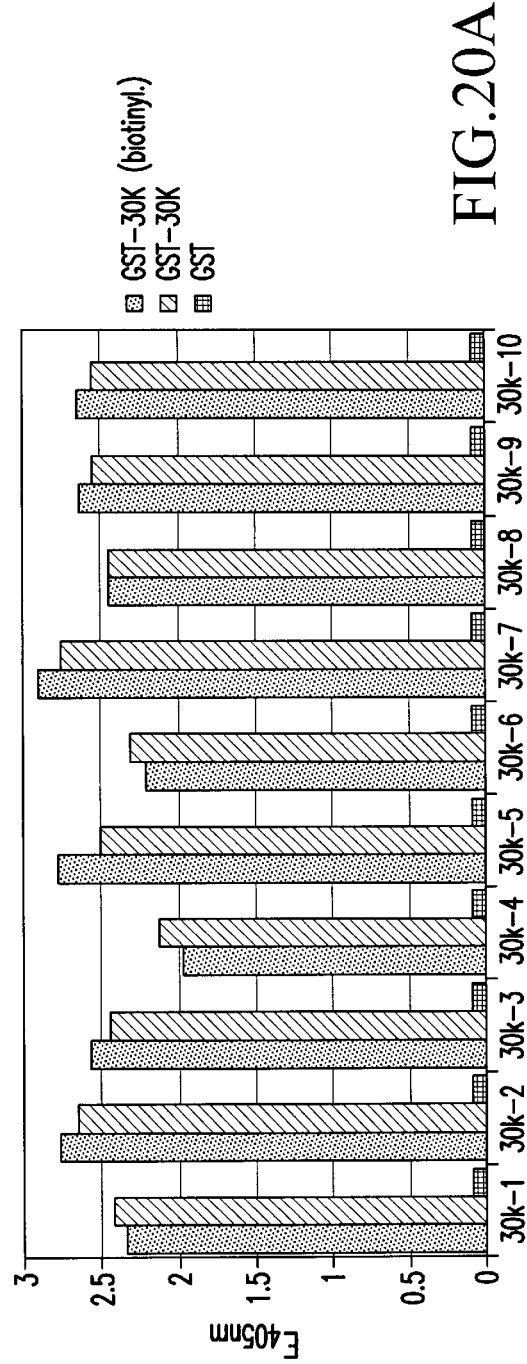
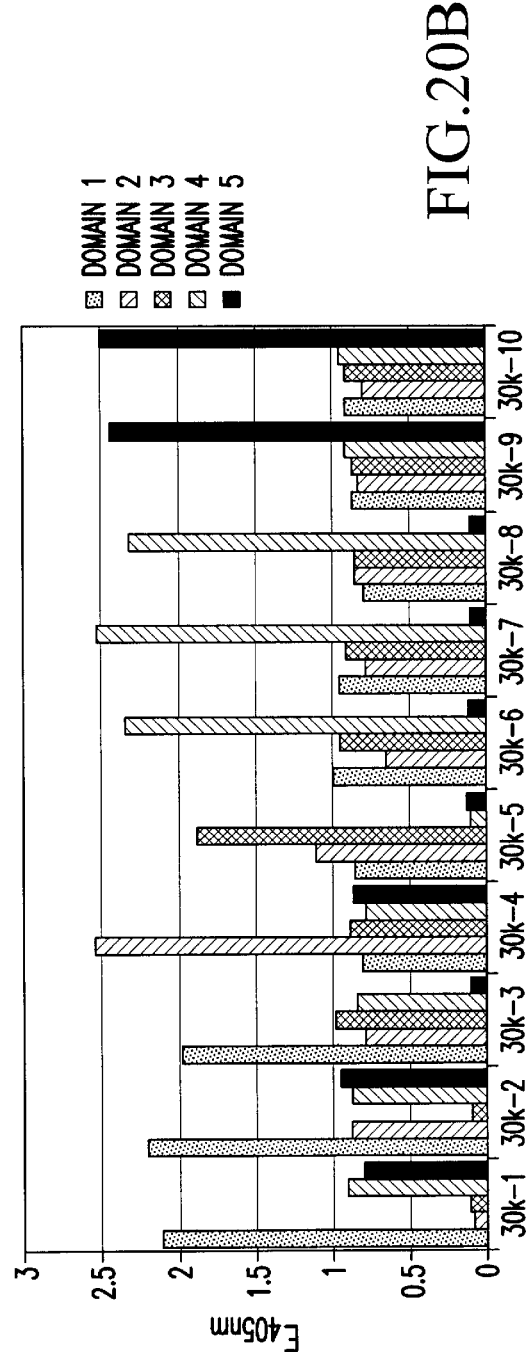
FIG.20A
FIG.20B

| | | | | | |
|---|---|---|---|---|---|
| scFv 30-1 | --EVHCKQSG | AELVKPGASV | KLSCRASDYT | FTSYYMYWVK | QRPGQGLEWI |
| scFv 30-2 | --EVKLQQSG | AELVKPGASV | KISCKASDYS | FTGYNMNWVK | QSHGKSLEWI |
| | | Framework I | | CDR H1 | Framework II |

| | | | | | |
|---|---|---|---|---|---|
| scFv 30-1 | GEIKPSGNGI | NENEKFKSKA | TLTSDYSSST | AYMQLSSLTS | EDSAVYYCTR |
| scFv 30-2 | GNINPYYGSI | SYNQKFKGKA | TLTVDKSSST | AYMQLNSLTS | EDSAVYYCAV |
| | CDR HII | | Framework III | | |

| | | | | | |
|---|---|---|---|---|---|
| scFv 30-1 | SGNAMD---Y | WGQGTTVTVS | SGGGGSGGGG | SGGGGSDIVL | TLSPATLSVT |
| scFv 30-2 | GGNYVDWFAY | WGQGTLVTVS | SGGGGSGGGG | SGGGGSDILL | TQSPLSLPVS |
| | CDR HIII | Framework IV | Linker (Gly₄Ser)₃ | | |

| | | | | | |
|---|---|---|---|---|---|
| scFv 30-1 | PGDRVSLSCR | ASQSISNFLH | -----WYQQK | SHESPRLLIK | YTSQSISGIP |
| scFv 30-2 | LGDHASISCR | SSQSLVHSNG | NTYLHWYLQN | PGQSPKLLIY | KVSNRFSGIP |
| | Framework I | CDR LI | | Framework II | CDR LII |

| | | | | | |
|---|---|---|---|---|---|
| scFv 30-1 | STFSGSGSGT | DFTLSINSVD | TEDFGMYFCQ | QSNSWPHRFG | SGIKLELKSA |
| scFv 30-2 | DRFSGSGSGT | DFTLKISRVE | AEDLGVYFCS | QSTHVPYTFG | GGTKLELKRA |
| | | Framework III | | CDR LIII | Framework IV |

| | | |
|---|---|---|
| scFv 30-1 | VDAAAEQKLI | SEEDLNGAA* |
| scFv 30-2 | VDAAAEQKLI | SEEDLNGAA* |
| | c-myc tag | |

FIG. 21

MAEVQLQQSG AELVKPGASV KMSCKASGYT FTNYNMHWVK QTPGQGLEWI
GAIYPRNGDT SYNQKFKGKA TLTADKSSST AYMQLSSLTS EDSAVYYCAR
PDVWGAGTLL TVSAGAGPTS GSGKPGPGEG STKGAPDVLM TQAPLTLSVT
IGQPASISCK SSQSLLDGDG KTYLNWLLQR PGQSPKRLIY LYSKLDSGVP
DRFTGSGSGT DFTLKISRVE AEDLGVYYCW QGTHFPHTFG GGTKLEIKRA
RAVDAAA

AMINOACID SEQUENCE OF scFv-3a-2 DERIVED FROM cDNA

FIG.23A

MAQVTLKESG PGILKPSQTL SLTCSFSGFS LSTSGMGVGW IRQPSGKGLE
WLAHIWWDDD KYYNPSLRSQ LTISKDTSRN QVFLRITNVD TADTATYYCA
RGYYGNDSPF AYWGQGTLLT VSSGAGPTSG SGKPGPGEGS TKGAPDIVLS
QSPKFMSTSV GDRVSITCKA SQIVRTAVAW FQQKPGQSPK ALIYLASNRH
TGVPDRFTGS GSGTDFTLTI SNVQSEDLAD YFCLQHWNYP FTFGSGTKLE
IKRAVDAAA

AMINOACID SEQUENCE OF scFv 54-1 DERIVED FROM cDNA

FIG.23B

MAQIQLVQSG PELKKPGQTV KISCKASAYT FTDYSMHWVK QAPGKGLKWM
GWINTETGEP TYADDFKGRF AFSLETSAST AYLQINTLKN EDSATYFCAR
GSGFNPYWGQ GTLVTVSAGA GPTSGSGKPG PGEGSTKGAP DIVLSQSPSS
LAVSVGEKVT MSCKSSQSLL YSSNQKNYLA WYQQKPGQSP KLLIYWASTR
ESGVPDRFTG SGSGTDFTLT INSVKAEDLA VYYCQQYYSY VTFGAGTKLE
IKRAVDAAA

AMINOACID SEQUENCE OF scFv-3min DERIVED FROM cDNA

FIG.23C (a)

| | 127 | 128 | 129 | 130 | 131 | 132 | 133 | 134 | 135 | 136 | 137 | 138 |
|---|---|---|---|---|---|---|---|---|---|---|---|---|
| TMV-coatprotein: | N | L | I | V | E | L | I | R | G | T | G | S |
| pVIII 9aa: | | | | | | | | | | | | |
| A1: | | | | K | T | D | L | VC | R | A | T | |
| A2: | | R | I | V | I | C | | G | R | V | T | |
| A4: | | | R | G | T | L | | PA | R | G | T | |
| A5: | | | | V | G | R | | Q | R | D | T | Q | S |
| B5: | F | L | R | V | D | A | | | R | E | T | |
| C4: | | V | A | G | M | L | | G | K | G | T | |
| D5: | | | R | W | E | L | | AN | R | S | T | |
| E5: | | | P | S | A | L | | GT | R | E | T | |
| F3: | | | K | N | D | L | | VS | R | A | T | |
| G1: | | Q | I | V | S | A | | W | R | E | T | |
| pVIII 9aa.Cys: | | | | | | | | | | | | |
| B9/G1: | | | | C | A | L | | PA | R | H | I | R | R | C |
| F3: | | | | C | Q | L | | PA | R | A | T | S | S | C |
| H1: | | | C | I | T | S | Q | | R | E | T | G | W | C |
| H5: | | | | | | C | | R | R | S | T | T | G | I | C |
| H10: | | | C | S | T | T | L | YK | R | G | T | C | | |
| consensus-sequence: | | | R | V | D | L | | PA | R | E | T | |

(b)

| | 402 | 403 | 404 | 405 | 406 | 407 | 408 | 409 | 410 | 411 | 412 | 413 |
|---|---|---|---|---|---|---|---|---|---|---|---|---|
| 54K-protein: | K | H | I | K | D | W | E | H | L | E | E | F |
| A2/A9/B8/C9: | | K | R | K | D | G | E | H | W | L | | |
| A6/B5/F8/H1: | R | Q | A | K | S | W | S | N | L | | | |
| G5: | Y | Q | A | K | E | W | S | N | L | | | |
| H10: | | | | K | D | W | E | H | R | V | P | S |
| consensus-sequence: | | | | K | D | W | E/S | H | L | | | |

(c)

| | | ← GST → | | | | | ← 3min → | | | | | |
|---|---|---|---|---|---|---|---|---|---|---|---|---|
| | -6 | -5 | -4 | -3 | -2 | -1 | +1 | +2 | +3 | +4 | +5 | +6 |
| GST-3min: | P | K | S | D | P | Q | M | G | K | R | R | R |
| pVIII 9aa: | | | | | | | | | | | | |
| A8: | | | | | H | P | R | P | Q | L | A | S | L |
| C2: | | | | | H | P | D | P | Q | L | S | H | S |
| E7: | R | | F | T | D | P | Q | L | H | P | | | |
| F5: | | | K | Q | D | P | Q | Q | H | K | Q | | |
| F8: | | | V | P | D | S | Q | L | E | W | P | | |
| G7: | | | H | C | D | P | Q | L | Y | Q | E | | |
| H1: | | | | | D | P | Q | M | F | R | R | H | C |
| H5: | | | F | K | D | G | Q | L | R | P | Q | | |
| pVIII 9aa.Cys: | | | | | | | | | | | | |
| A4: | | | C | P | D | P | Q | L | R | L | H | R | C |
| A5: | | | C | P | D | P | Q | L | N | G | T | R | C |
| A7/B10/H4: | | | C | P | D | P | Q | L | S | S | L | R | C |
| A8: | | | C | P | D | P | Q | L | R | L | H | R | C |
| A9: | | | C | P | D | P | Q | L | T | L | H | R | C |
| G4: | | | C | P | D | P | Q | L | S | L | Q | R | C |
| H6: | | | C | P | D | A | Q | L | S | G | T | R | C |
| consensus-sequence: | | | H | P | D | P | Q | L | S | L | H | R | |

FIG. 25

FIG.26A  biscFv2429-apoplast
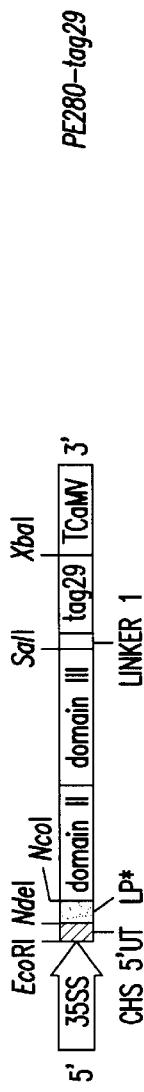
FIG.26B  PE280-tag29
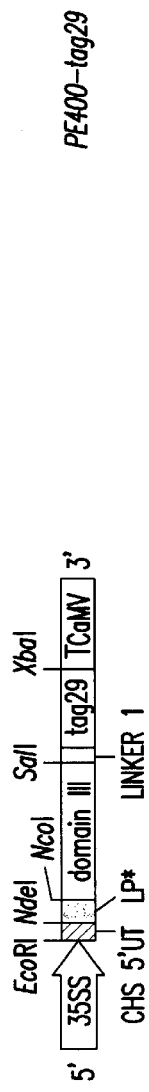
FIG.26C  PE400-tag29
FIG.26D  GST-tag29 pscFv24-PDGFR

SEQUENCE LISTING

<160> NUMBER OF SEQ ID NOS: 168

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: synthetic,
      no natural origin

<400> SEQUENCE: 1
gccgtcgacg aggacctgaa caaggtgttc cca                                 33

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: synthetic,
      no natural origin

<400> SEQUENCE: 2
gcctctagat cagaaatcct ttctcttg                                       28

<210> SEQ ID NO 3
<211> LENGTH: 1378
<212> TYPE: DNA
<213> ORGANISM: Artificial Sequence
<220> FEATURE:
<223> OTHER INFORMATION: Description of Artificial Sequence: synthetic, no natural origin

<400> SEQUENCE: 3

```
gaattcacac acaatcagat ttatagagag atttataaaa aaaaaaaaac atatggattt      60
tcaagtgcag attttcagct tcctgctaat cagtgcctca gtcataatat ctagaggaca     120
aattgttctc acccagtctc cagcaatcat gtctgcatct ccaggggaga aggtcaccat     180
gacctgcagt gccagttcaa gtgtaagtaa aatgcaatgg tatcagcaga agtcaggcac     240
ctcccccaaa agatggattt atgacacatc caaactggcc tctggagtcc ctggtcgctt     300
cagtggcagt gggtctggga cctcttactc tctcacaatc agcagcatgg aggctgaaga     360
tgctgccact tattactgcc agcagtggag tagtaacccg ctcacgttcg gtgctgggac     420
caagctggag ataaaaggct ctactagtgg ttccggaag agctctgaag gtaaaggtga      480
ggtccagctg cagcagtctg gacctgagct ggtaaatcct ggggcttcag tgaagatgtc     540
ctgcaaggcc tctggataca cattcattac ctatgttatg cactgggtga agcagaagcc     600
tgggcagggc cttgagtgga ttggatatat taatcctaac aaagacggta caaagttcaa     660
tgagaagttc aaaggcaagg ccacactgac ttcagacaaa tcctccaaca cagcctacat     720
ggagctcagc agcctgacct ctgaggactc tgcggtctat tactgtgcaa gagactatga     780
ttacgactgg tttgcttact ggggccaggg gactctggtc actgtctctg cagtcgacga     840
ggacctgaac aaggtgttcc cacccgaggt cgctgtgttt gagccatcag aagcagagat     900
ctcccacacc caaaaggcca cactggtgtg cctggccaca ggcttcttcc ctgaccacgt     960
ggagctgagc tggtgggtga atgggaagga ggtgcacagt ggggtcagca cggacccgca    1020
gcccctcaag gagcagcccg ccctcaatga ctccagatac tgcctgagca gccgcctgag    1080
ggtctcggcc accttctggc agaaccccg caaccacttc gctgtcaag tccagttcta     1140
cgggctctcg gagaatgacg agtggaccca ggatagggcc aaacccgtca cccagatcgt    1200
cagcgccgag gcctggggta gagcagactg tggcttaacc tcggtgtcct accagcaagg    1260
ggtcctgtct gccaccatcc tctatgagat cctgctaggg aaggccaccc tgtatgctgt    1320
gctggtcagt gcccttgtgt tgatggccat ggtcaagaga aaggatttct gatctaga     1378
```

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: synthetic,
      no natural origin

<400> SEQUENCE: 4

```
gttttcccag tcacgac                                                    17
```

<210> SEQ ID NO 5
<211> LENGTH: 130
<212> TYPE: DNA
<213> ORGANISM: Artificial Sequence
<220> FEATURE:
<223> OTHER INFORMATION: Description of Artificial Sequence: synthetic,
      no natural origin

<400> SEQUENCE: 5

```
ggctctagac gctcgagttt aaaacctata atacacatag atgttgcaat aaagcaaaat     60
cagtatacaa atagtccacc agaaatactc cctatacttc ttagcggccg cagaacctcc    120
acctccgtcg                                                           130
```

```
<210> SEQ ID NO 6
<211> LENGTH: 148
<212> TYPE: DNA
<213> ORGANISM: Artificial Sequence
<220> FEATURE:
<223> OTHER INFORMATION: Description of Artificial Sequence: synthetic,
      no natural origin

<400> SEQUENCE: 6
ggctctagac gctcgagttt agaaatgcct agatctctta atcaagatga agagcatcaa      60
gcaaattccg agcagcgctg ccaagaaagt caccaagagc aaagttcttc ccaatctcct    120
agcggccgca gaacctccac ctccgtcg                                        148

<210> SEQ ID NO 7
<211> LENGTH: 145
<212> TYPE: DNA
<213> ORGANISM: Artificial Sequence
<220> FEATURE:
<223> OTHER INFORMATION: Description of Artificial Sequence: synthetic,
      no natural origin

<400> SEQUENCE: 7
ggctctagac gctcgagttt aatcctctgc catgtagagt ctatacatga gagcaaccac      60
gagtgctgat atcgctggga tcacccaatt ggtccaccat gaagagttag actcaacagc    120
ggccgcagaa cctccacctc cgtcg                                           145

<210> SEQ ID NO 8
<211> LENGTH: 130
<212> TYPE: DNA
<213> ORGANISM: Artificial Sequence
<220> FEATURE:
<223> OTHER INFORMATION: Description of Artificial Sequence: synthetic,
      no natural origin

<400> SEQUENCE: 8
ggctctagac gctcgagttt aagtgaagaa ataaataaca ataacaacaa caataatagc      60
acaaatagca ccaagcataa tcatcatctt acaattcttc caagcggccg cagaacctcc    120
acctccgtcg                                                            130

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: synthetic,
      no natural origin

<400> SEQUENCE: 9
gttttcccag tcacgac                                                     17

<210> SEQ ID NO 10
<211> LENGTH: 35
<212> TYPE: DNA
<213> ORGANISM: Artificial Sequence
<220> FEATURE:
<223> OTHER INFORMATION: Description of Artificial Sequence: synthetic,
      no natural origin

<400> SEQUENCE: 10
ggctctagac gctcgagttt agaaatgcct agatc                                 35
```

```
<210> SEQ ID NO 11
<211> LENGTH: 51
<212> TYPE: DNA
<213> ORGANISM: Artificial Sequence
<220> FEATURE:
<223> OTHER INFORMATION: Description of Artificial Sequence: synthetic,
      no natural origin

<400> SEQUENCE: 11
ggctctagac gctcgagttt aagtgaagaa ataaataaca ataacaacaa c          51

<210> SEQ ID NO 12
<211> LENGTH: 900
<212> TYPE: DNA
<213> ORGANISM: Artificial Sequence
<220> FEATURE:
<223> OTHER INFORMATION: Description of Artificial Sequence: synthetic,
      no natural origin

<400> SEQUENCE: 12
gaattcacaa cacaaatcag atttatagag agatttataa aaaaaaaaaa acatatgcaa    60
attgttctca cccagtctcc agcaatcatg tctgcatctc caggggagaa ggtcaccatg   120
acctgcagtg ccagttcaag tgtaagtaaa atgcaatggt atcagcagaa gtcaggcacc   180
tcccccaaaa gatggattta tgacacatcc aaactggcct ctggagtccc tggtcgcttc   240
agtggcagtg gtctgggac ctcttactct ctcacaatca gcagcatgga ggctgaagat   300
gctgccactt attactgcca gcagtggagt agtaacccgc tcacgttcgg tgctgggacc   360
aagctggaga taaaggctc tactagtggt tccgggaaga gctctgaagg taaaggtgag   420
gtccagctgc agcagtctgg acctgagctg gtaaatcctg gggcttcagt gaagatgtcc   480
tgcaaggcct ctggatacac attcattacc tatgttatgc actgggtgaa gcagaagcct   540
gggcagggcc ttgagtggat tggatatatt aatcctaaca agacggtac aaagttcaat   600 gagaagttca aggcaaggc cacactgact tcagacaaat cctccaacac agcctacatg   660
gagctcagca gcctgacctc tgaggactct gcggtctatt actgtgcaag agactatgat   720
tacgactggt ttgcttactg gggccagggg actctggtca ctgtctctgc agtcgacgga   780
ggtggaggtt ctgcggccgc taagaagtat agggagtatt tcttgtggac tatttgtata   840
ctgattttgc tttattgcaa catctatgtg tattataggt tttaaactcg agcgtctaga   900

<210> SEQ ID NO 13
<211> LENGTH: 918
<212> TYPE: DNA
<213> ORGANISM: Artificial Sequence
<220> FEATURE:
<223> OTHER INFORMATION: Description of Artificial Sequence: synthetic,
      no natural origin

<400> SEQUENCE: 13
gaattcacaa cacaaatcag atttatagag agatttataa aaaaaaaaaa acatatgcaa    60
attgttctca cccagtctcc agcaatcatg tctgcatctc caggggagaa ggtcaccatg   120
acctgcagtg ccagttcaag tgtaagtaaa atgcaatggt atcagcagaa gtcaggcacc   180
tcccccaaaa gatggattta tgacacatcc aaactggcct ctggagtccc tggtcgcttc   240
agtggcagtg gtctgggac ctcttactct ctcacaatca gcagcatgga ggctgaagat   300
gctgccactt attactgcca gcagtggagt agtaacccgc tcacgttcgg tgctgggacc   360
aagctggaga taaaggctc tactagtggt tccgggaaga gctctgaagg taaaggtgag   420
gtccagctgc agcagtctgg acctgagctg gtaaatcctg gggcttcagt gaagatgtcc   480
```

```
tgcaaggcct ctggatacac attcattacc tatgttatgc actgggtgaa gcagaagcct      540
gggcagggcc ttgagtggat tggatatatt aatcctaaca agacggtac aaagttcaat       600 gagaagttca aggcaaggc cacactgact tcagacaaat cctccaacac agcctacatg        660
gagctcagca gcctgacctc tgaggactct gcggtctatt actgtgcaag agactatgat      720
tacgactggt ttgcttactg gggccagggg actctggtca ctgtctctgc agtcgacgga      780
ggtggaggtt ctgcggccgc taggagattg gaagaactt tgctcttggt gactttcttg      840
gcagcgctgc tcggaatttg cttgatgctc ttcatcttga ttaagagatc taggcatttc      900
taaactcgag cgtctaga                                                    918

<210> SEQ ID NO 14
<211> LENGTH: 915
<212> TYPE: DNA
<213> ORGANISM: Artificial Sequence
<220> FEATURE:
<223> OTHER INFORMATION: Description of Artificial Sequence: synthetic,
      no natural origin

<400> SEQUENCE: 14
gaattcacaa cacaaatcag atttatagag agatttataa aaaaaaaaaa acatatgcaa       60
attgttctca cccagtctcc agcaatcatg tctgcatctc caggggagaa ggtcaccatg       120
acctgcagtg ccagttcaag tgtaagtaaa atgcaatggt atcagcagaa gtcaggcacc      180
tcccccaaaa gatggattta tgacacatcc aaactggcct ctggagtccc tggtcgcttc      240
agtggcagtg ggtctgggac ctcttactct ctcacaatca gcagcatgga ggctgaagat      300
gctgccactt attactgcca gcagtggagt agtaacccgc tcacgttcgg tgctgggacc      360
aagctggaga taaaggctc tactagtggt tccgggaaga gctctgaagg taaaggtgag      420
gtccagctgc agcagtctgg acctgagctg gtaaatcctg gggcttcagt gaagatgtcc      480
tgcaaggcct ctggatacac attcattacc tatgttatgc actgggtgaa gcagaagcct      540
gggcagggcc ttgagtggat tggatatatt aatcctaaca agacggtac aaagttcaat       600 gagaagttca aggcaaggc cacactgact tcagacaaat cctccaacac agcctacatg        660
gagctcagca gcctgacctc tgaggactct gcggtctatt actgtgcaag agactatgat      720
tacgactggt ttgcttactg gggccagggg actctggtca ctgtctctgc agtcgacgga      780
ggtggaggtt ctgcggccgc tgttgagtct aactcttcat ggtggaccaa ttgggtgatc      840
ccagcgatat cagcactcgt ggttgctctc atgtatagac tctacatggc agaggattaa      900
actcgagcgt ctaga                                                       915

<210> SEQ ID NO 15
<211> LENGTH: 900
<212> TYPE: DNA
<213> ORGANISM: Artificial Sequence
<220> FEATURE:
<223> OTHER INFORMATION: Description of Artificial Sequence: synthetic,
      no natural origin

<400> SEQUENCE: 15
gaattcacaa cacaaatcag atttatagag agatttataa aaaaaaaaaa acatatgcaa       60
attgttctca cccagtctcc agcaatcatg tctgcatctc caggggagaa ggtcaccatg       120
acctgcagtg ccagttcaag tgtaagtaaa atgcaatggt atcagcagaa gtcaggcacc      180
tcccccaaaa gatggattta tgacacatcc aaactggcct ctggagtccc tggtcgcttc      240
```

```
agtggcagtg ggtctgggac ctcttactct ctcacaatca gcagcatgga ggctgaagat    300
gctgccactt attactgcca gcagtggagt agtaacccgc tcacgttcgg tgctgggacc    360
aagctggaga taaaaggctc tactagtggt tccgggaaga gctctgaagg taaaggtgag    420
gtccagctgc agcagtctgg acctgagctg gtaaatcctg gggcttcagt gaagatgtcc    480
tgcaaggcct ctggatacac attcattacc tatgttatgc actgggtgaa gcagaagcct    540
gggcagggcc ttgagtggat tggatatatt aatcctaaca agacggtac aaagttcaat    600 gagaagttca aggcaaggc cacactgact tcagacaaat cctccaacac agcctacatg    660
gagctcagca gcctgacctc tgaggactct gcggtctatt actgtgcaag agactatgat    720
tacgactggt ttgcttactg gggccagggg actctggtca ctgtctctgc agtcgacgga    780
ggtggaggtt ctgcggccgc ttggaagaat tgtaagatga tgattatgct tggtgctatt    840
tgtgctatta ttgttgttgt tattgttatt tatttcttca cttaaactcg agcgtctaga    900
```

<210> SEQ ID NO 16
<211> LENGTH: 45
<212> TYPE: DNA
<213> ORGANISM: Artificial Sequence
<220> FEATURE:
<223> OTHER INFORMATION: Description of Artificial Sequence: synthetic,
      no natural origin

<400> SEQUENCE: 16

```
gcggaattcg acgtcgccat ggccttcctc ggcgacggcg gcgac                     45
```

<210> SEQ ID NO 17
<211> LENGTH: 37
<212> TYPE: DNA
<213> ORGANISM: Artificial Sequence
<220> FEATURE:
<223> OTHER INFORMATION: Description of Artificial Sequence: synthetic,
      no natural origin

<400> SEQUENCE: 17

```
gcgaagcttg tcgaccggcg gtttgccggg ctggctg                              37
```

<210> SEQ ID NO 18
<211> LENGTH: 1604
<212> TYPE: DNA
<213> ORGANISM: Artificial Sequence
<220> FEATURE:
<223> OTHER INFORMATION: Description of Artificial Sequence: synthetic,
      no natural origin

<400> SEQUENCE: 18

```
gaattcacac acaatcagat ttatagagag atttataaaa aaaaaaaaac atatggattt     60
tcaagtgcag atttttcagct tcctgctaat cagtgcctca gtcataatat ctagaggaca    120
aattgttctc acccagtctc cagcaatcat gtctgcatct ccaggggaga aggtcaccat    180
gacctgcagt gccagttcaa gtgtaagtaa aatgcaatgg tatcagcaga gtcaggcac    240 ctcccccaaa agatggattt atgacacatc caaactggcc tctggagtcc ctggtcgctt    300
cagtggcagt gggtctggga cctcttactc tctcacaatc agcagcatgg aggctgaaga    360
tgctgccact tattactgcc agcagtggag tagtaaccccg ctcacgttcg gtgctgggac    420
caagctggag ataaaaggct ctactagtgg ttccgggaag agctctgaag gtaaaggtga    480
ggtccagctg cagcagtctg gacctgagct ggtaaatcct ggggcttcag tgaagatgtc    540
ctgcaaggcc tctggataca cattcattac ctatgttatg cactgggtga agcagaagcc    600
```

```
tgggcagggc cttgagtgga ttggatatat aatcctaac aaagacggta caaagttcaa      660
tgagaagttc aaaggcaagg ccacactgac ttcagacaaa tcctccaaca cagcctacat      720
ggagctcagc agcctgacct ctgaggactc tgcggtctat tactgtgcaa gagactatga      780
ttacgactgg tttgcttact ggggccaggg gactctggtc actgtctctg caatcgatcc      840
cgggggtaac cgcggtaccg ccactacccg tcgtccggct accaccactg gctcgagtcc      900
agggcccacc cagtctcata gcgacgtcag cttcagcacc cgcggcacgc agaactggac      960
ggtggagcgg ctgctccagg cgcaccgcca actggaggag cgcggctatg tgttcgtcgg     1020
ctaccacggc accttcctcg aagcggcgca agcatcgtc ttcggcgggg tgcgcgcgcg     1080
cagccaggac ctcgacgcga tctggcgcgg tttctatatc gccggcgatc cggcgctggc     1140
ctacggctac gcccaggacc aggaacccga cgcacgcggc cggatccgca acggtgccct     1200
gctgcgggtc tatgtgccgc gctcgagcct gccgggcttc taccgcacca gcctgaccct     1260
ggccgcgccg gaggcggcgg gcgaggtcga acggctgatc ggccatccgc tgccgctgcg     1320
cctggacgcc atcaccggcc cgaggagga aggcgggcgc ctggagacca ttctcggctg     1380
gccgctggcc gagcgcaccg tggtgattcc ctcggcgatc cccaccgacc gcgcaacgt     1440 cggcggcgac ctcgacccgt ccagcatccc cgacaaggaa caggcgatca gcgccctgcc     1500
ggactacgcc agccagcccg gcaaaccgcc ggtcgacgga ggtggaggtt ctaagcacat     1560
caaggactgg gagcacctcg aagagttcta aactcgagtc taga                     1604

<210> SEQ ID NO 19
<211> LENGTH: 1050
<212> TYPE: PRT
<213> ORGANISM: Artificial Sequence
<220> FEATURE:
<223> OTHER INFORMATION: Description of Artificial Sequence: synthetic,
      no natural origin

<400> SEQUENCE: 19

Met Gln Ile Val Leu Thr Gln Ser Pro Ala Ile Met Ser Ala Ser Pro
  1               5                  10                  15

Gly Glu Lys Val Thr Met Thr Cys Ser Ala Ser Ser Val Ser Lys
             20                  25                  30

Met Gln Trp Tyr Gln Gln Lys Ser Gly Thr Ser Pro Lys Arg Trp Ile
         35                  40                  45

Tyr Asp Thr Ser Lys Leu Ala Ser Gly Val Pro Gly Arg Phe Ser Gly
     50                  55                  60

Ser Gly Ser Gly Thr Ser Tyr Ser Leu Thr Ile Ser Ser Met Glu Ala
 65                  70                  75                  80

Glu Asp Ala Ala Thr Tyr Tyr Cys Gln Gln Gly Thr Lys Leu Glu Ile
                 85                  90                  95

Lys Gly Ser Thr Ser Gly Ser Gly Lys Ser Ser Glu Gly Lys Gly Glu
            100                 105                 110

Val Gln Leu Gln Gln Ser Gly Pro Glu Leu Val Asn Pro Gly Ala Ser
        115                 120                 125

Val Lys Met Ser Cys Lys Ala Ser Gly Tyr Thr Phe Ile Thr Tyr Val
    130                 135                 140

Met His Trp Val Lys Gln Lys Pro Gly Gln Gly Leu Glu Trp Ile Gly
145                 150                 155                 160

Tyr Ile Asn Pro Asn Lys Asp Gly Thr Lys Phe Asn Glu Lys Phe Lys
                165                 170                 175

Gly Lys Ala Thr Leu Thr Ser Asp Lys Ser Ser Asn Thr Ala Tyr Met
```

-continued

```
            180                 185                 190
Glu Leu Ser Ser Leu Thr Ser Glu Asp Ser Ala Val Tyr Tyr Cys Ala
            195                 200                 205
Arg Asp Tyr Asp Tyr Asp Trp Phe Ala Tyr Trp Gly Gln Gly Thr Leu
            210                 215                 220
Val Thr Val Ser Ala Val Asp Gly Gly Gly Ser Met Lys Arg Met Leu
225                 230                 235                 240
Ile Asn Ala Thr Gln Gln Glu Glu Leu Arg Val Ala Leu Val Asp Gly
                245                 250                 255
Gln Arg Leu Tyr Asp Leu Asp Ile Glu Ser Pro Gly His Glu Gln Lys
            260                 265                 270
Lys Ala Asn Ile Tyr Lys Gly Lys Ile Thr Arg Ile Glu Pro Ser Leu
            275                 280                 285
Glu Ala Ala Phe Val Asp Tyr Gly Ala Glu Arg His Gly Phe Leu Pro
            290                 295                 300
Leu Lys Glu Ile Ala Arg Glu Tyr Phe Pro Ala Asn Tyr Ser Ala His
305                 310                 315                 320
Gly Arg Pro Asn Ile Lys Asp Val Leu Arg Glu Gly Gln Glu Val Ile
                325                 330                 335
Val Gln Ile Asp Lys Glu Glu Arg Gly Asn Lys Gly Ala Ala Leu Thr
            340                 345                 350
Thr Phe Ile Ser Leu Ala Gly Ser Tyr Leu Val Leu Met Pro Asn Asn
            355                 360                 365
Pro Arg Ala Gly Gly Ile Ser Arg Arg Ile Glu Gly Asp Asp Arg Thr
            370                 375                 380
Glu Leu Lys Glu Ala Leu Ala Ser Leu Glu Leu Pro Glu Gly Met Gly
385                 390                 395                 400
Leu Ile Val Arg Thr Ala Gly Val Gly Lys Ser Ala Glu Ala Leu Gln
                405                 410                 415
Trp Asp Leu Ser Phe Arg Leu Lys His Trp Glu Ala Ile Lys Lys Ala
            420                 425                 430
Ala Glu Ser Arg Pro Ala Pro Phe Leu Ile His Gln Glu Ser Asn Val
            435                 440                 445
Ile Val Arg Ala Phe Arg Asp Tyr Leu Arg Gln Asp Ile Gly Glu Ile
            450                 455                 460
Leu Ile Asp Asn Pro Lys Val Leu Glu Leu Ala Arg Gln His Ile Ala
465                 470                 475                 480
Ala Leu Gly Arg Pro Asp Phe Ser Ser Lys Ile Lys Leu Tyr Thr Gly
                485                 490                 495
Glu Ile Pro Leu Phe Ser His Tyr Gln Ile Glu Ser Gln Ile Glu Ser
            500                 505                 510
Ala Phe Gln Arg Glu Val Arg Leu Pro Ser Gly Gly Ser Ile Val Ile
            515                 520                 525
Asp Ser Thr Glu Ala Leu Thr Ala Ile Asp Ile Asn Ser Ala Arg Ala
            530                 535                 540
Thr Arg Gly Gly Asp Ile Glu Glu Thr Ala Phe Asn Thr Asn Leu Glu
545                 550                 555                 560
Ala Ala Asp Glu Ile Ala Arg Gln Leu Arg Leu Arg Asp Leu Gly Gly
                565                 570                 575
Leu Ile Val Ile Asp Phe Ile Asp Met Thr Pro Val Arg His Gln Arg
            580                 585                 590
Ala Val Glu Asn Arg Leu Arg Glu Ala Val Arg Gln Asp Arg Ala Arg
            595                 600                 605
```

```
Ile Gln Ile Ser His Ile Ser Arg Phe Gly Leu Leu Glu Met Ser Arg
    610                 615                 620
His Arg Leu Ser Pro Ser Leu Gly Glu Ser Ser His His Val Cys Pro
625                 630                 635                 640
Arg Cys Ser Gly Thr Gly Thr Val Arg Asp Asn Glu Ser Leu Ser Leu
                645                 650                 655
Ser Ile Leu Arg Leu Ile Glu Glu Ala Leu Lys Glu Asn Thr Gln
        660                 665                 670
Glu Val His Ala Ile Val Pro Val Pro Ile Ala Ser Tyr Leu Leu Asn
            675                 680                 685
Glu Lys Arg Ser Ala Val Asn Ala Ile Glu Thr Arg Gln Asp Gly Val
    690                 695                 700
Arg Cys Val Ile Val Pro Asn Asp Gln Met Glu Thr Pro His Tyr His
705                 710                 715                 720
Val Val Arg Val Arg Lys Gly Glu Glu Thr Pro Thr Leu Ser Tyr Met
                725                 730                 735
Leu Pro Lys Leu His Glu Glu Ala Met Ala Leu Pro Ser Glu Glu Glu
            740                 745                 750
Phe Ala Glu Arg Lys Arg Pro Glu Gln Pro Ala Leu Ala Thr Phe Ala
    755                 760                 765
Met Pro Asp Val Pro Pro Ala Pro Thr Pro Ala Glu Pro Ala Ala Pro
770                 775                 780
Val Val Ala Pro Ala Pro Lys Ala Ala Pro Ala Thr Pro Ala Ala Pro
785                 790                 795                 800
Ala Gln Pro Gly Leu Leu Ser Arg Phe Phe Gly Ala Leu Lys Ala Leu
                805                 810                 815
Phe Ser Gly Gly Glu Thr Lys Pro Thr Glu Gln Pro Ala Pro Lys
            820                 825                 830
Ala Glu Ala Lys Pro Glu Arg Gln Gln Asp Arg Arg Lys Pro Arg Gln
    835                 840                 845
Asn Asn Arg Arg Asp Arg Asn Glu Arg Arg Asp Thr Arg Ser Glu Arg
850                 855                 860
Thr Glu Gly Ser Asp Asn Arg Glu Glu Asn Arg Arg Asn Arg Arg Gln
865                 870                 875                 880
Ala Gln Gln Gln Thr Ala Glu Thr Arg Glu Ser Arg Gln Ala Glu
                885                 890                 895
Val Thr Glu Lys Ala Arg Thr Ala Asp Glu Gln Gln Ala Pro Arg Arg
            900                 905                 910
Glu Arg Ser Arg Arg Arg Asn Asp Asp Lys Arg Gln Ala Gln Gln Glu
    915                 920                 925
Ala Lys Ala Leu Asn Val Glu Glu Gln Ser Val Gln Glu Thr Glu Gln
930                 935                 940
Glu Glu Arg Val Arg Pro Val Gln Pro Arg Arg Lys Gln Arg Gln Leu
945                 950                 955                 960
Asn Gln Lys Val Arg Tyr Glu Gln Ser Val Ala Glu Glu Ala Val Val
                965                 970                 975
Ala Pro Val Val Glu Glu Thr Val Ala Ala Glu Pro Ile Val Gln Glu
            980                 985                 990
Ala Pro Ala Pro Arg Thr Glu Leu Val Lys Val Pro Leu Pro Val Val
    995                 1000                1005
Ala Gln Thr Ala Pro Glu Gln Gln Glu Glu Asn Asn Ala Asp Asn Arg
1010                1015                1020
```

Asp Asn Gly Gly Met Pro Ser Phe Ser Pro Leu Ala Ser Ser Pro Ala
1025                1030                1035                1040

Arg Lys Trp Ser Ala Ser Ser Ser Leu Ser
            1045                1050

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence: synthetic,
      no natural origin

<400> SEQUENCE: 20
actgcgccat ggcttacagt atcact                                          26

<210> SEQ ID NO 21
<211> LENGTH: 72
<212> TYPE: DNA
<213> ORGANISM: Artificial Sequence
<220> FEATURE:
<223> OTHER INFORMATION: Description of Artificial Sequence: synthetic,
      no natural origin

<400> SEQUENCE: 21
ccgtcagacg tcagaacctc cacctccact tccgccgcct ccagttgcag gaccagaggt     60
ccaaaccaaa cc                                                         72

<210> SEQ ID NO 22
<211> LENGTH: 71
<212> TYPE: DNA
<213> ORGANISM: Artificial Sequence
<220> FEATURE:
<223> OTHER INFORMATION: Description of Artificial Sequence: synthetic,
      no natural origin

<400> SEQUENCE: 22
ctacccctcg agtttagtga tggtgatggt gatgagcggc cgcgtcgact gcagagacag     60
tgaccagagt c                                                          71

<210> SEQ ID NO 23
<211> LENGTH: 88
<212> TYPE: DNA
<213> ORGANISM: Artificial Sequence
<220> FEATURE:
<223> OTHER INFORMATION: Description of Artificial Sequence: synthetic,
      no natural origin

<400> SEQUENCE: 23
ccctcactcg agtttagagc tcatctttct cagatccacg agcggccgca gaacctccac     60
ctccgtcgac tgcagagaca gtgaccag                                        88

<210> SEQ ID NO 24
<211> LENGTH: 1561
<212> TYPE: DNA
<213> ORGANISM: Artificial Sequence
<220> FEATURE:
<223> OTHER INFORMATION: Description of Artificial Sequence: synthetic,
      no natural origin

<400> SEQUENCE: 24
gaattcgtat ttttacaaca attaccaaca acaacaacaa caacaacatt acaattacta     60
tttacaagga ccatggctta cagtatcact actccatctc agttcgtgtt cttgtcatca    120

| gcgtgggccg acccaataga gttaattaat ttatgtacta atgccttagg aaatcagttt | 180 |
| caaacacaac aagctcgaac tgtcgttcaa agacaattca gtgaggtgtg gaaaccttca | 240 |
| ccacaagtaa ctgttaggtt ccctgacagt gactttaagg tgtacaggta caatgcggta | 300 |
| ttagacccgc tagtcacagc actgttaggt gcattcgaca ctagaaatag aataatagaa | 360 |
| gttgaaaatc aggcgaaccc cacgactgcc gaaacgttag atgctactcg tagagtagac | 420 |
| gacgcaacgg tggccataag gagcgcgata aataatttaa tagtagaatt gatcagagga | 480 |
| accggatctt ataatcggag ctctttcgag agctcttctg gtttggtttg gacctctggt | 540 |
| cctgcaactg gaggcggcgg aagtggaggt ggaggttctg acgtcgtgct gacccagtct | 600 |
| ccagcaatca tgtctgcatc tccaggggag aaggtcacca tgacctgcag tgccagttca | 660 |
| agtgtaagta aaatgcaatg gtatcagcag aagtcaggca cctcccccaa aagatggatt | 720 |
| tatgacacat ccaaactggc ctctggagtc cctggtcgct tcagtggcag tgggtctggg | 780 |
| acctcttact ctctcacaat cagcagcatg gaggctgaag atgctgccac ttattactgc | 840 |
| cagcagtgga gtagtaaccc gctcacgttc ggtgctggga ccaagctgga gataaaaggc | 900 |
| tctactagtg gttccgggaa gagctctgaa ggtaaaggtg aggtccagct gcagcagtct | 960 |
| ggacctgagc tggtaaatcc tggggcttca gtgaagatgt cctgcaaggc tctggatac | 1020 |
| acattcatta cctatgttat gcactgggtg aagcagaagc ctgggcaggg ccttgagtgg | 1080 |
| attggatata ttaatcctaa caaagacggt acaaagttca tgagaagtt caaaggcaag | 1140 |
| gccacactga cttcagacaa atcctccaac acagcctaca tggagctcag cagcctgacc | 1200 |
| tctgaggact ctgcggtcta ttactgtgca agagactatg attacgactg gtttgcttac | 1260 |
| tggggccagg ggactctggt cactgtctct gcagtcgacg cggccgctca tcaccatcac | 1320 |
| catcactaaa ctcgagggt agtcaagatg cataataaat aacggattgt gtccgtaatc | 1380 |
| acacgtggtg cgtacgataa cgcatagtgt ttttccctcc acttaaatcg aagggttgtg | 1440 |
| tcttggatcg cgcgggtcaa atgtatatgg ttcatataca tccgcaggca cgtaataaag | 1500 |
| cgagggttc gaatcccccc gttaccccg gtaggggccc aggtaccggc gcgcctctag | 1560 |
| a | 1561 |

<210> SEQ ID NO 25
<211> LENGTH: 1582
<212> TYPE: DNA
<213> ORGANISM: Artificial Sequence
<220> FEATURE:
<223> OTHER INFORMATION: Description of Artificial Sequence: synthetic,
      no natural origin

<400> SEQUENCE: 25

| gaattcgtat ttttacaaca attaccaaca acaacaacaa caacaacatt acaattacta | 60 |
| tttacaagga ccatggctta cagtatcact actccatctc agttcgtgtt cttgtcatca | 120 |
| gcgtgggccg acccaataga gttaattaat ttatgtacta atgccttagg aaatcagttt | 180 |
| caaacacaac aagctcgaac tgtcgttcaa agacaattca gtgaggtgtg gaaaccttca | 240 |
| ccacaagtaa ctgttaggtt ccctgacagt gactttaagg tgtacaggta caatgcggta | 300 |
| ttagacccgc tagtcacagc actgttaggt gcattcgaca ctagaaatag aataatagaa | 360 |
| gttgaaaatc aggcgaaccc cacgactgcc gaaacgttag atgctactcg tagagtagac | 420 |
| gacgcaacgg tggccataag gagcgcgata aataatttaa tagtagaatt gatcagagga | 480 |
| accggatctt ataatcggag ctctttcgag agctcttctg gtttggtttg gacctctggt | 540 |

```
cctgcaactg gaggcggcgg aagtggaggt ggaggttctg acgtcgtgct gacccagtct    600
ccagcaatca tgtctgcatc tccaggggag aaggtcacca tgacctgcag tgccagttca    660
agtgtaagta aaatgcaatg gtatcagcag aagtcaggca cctcccccaa agatggatt     720 tatgacacat ccaaactggc ctctggagtc cctggtcgct tcagtggcag tgggtctggg    780
acctcttact ctctcacaat cagcagcatg gaggctgaag atgctgccac ttattactgc    840
cagcagtgga gtagtaaccc gctcacgttc ggtgctggga ccaagctgga gataaaaggc    900
tctactagtg gttccgggaa gagctctgaa ggtaaaggtg aggtccagct gcagcagtct    960
ggacctgagc tggtaaatcc tggggcttca gtgaagatgt cctgcaaggc tctggatac    1020 acattcatta cctatgttat gcactgggtg aagcagaagc ctgggcaggg ccttgagtgg    1080
attggatata ttaatcctaa caagacggt acaaagttca atgagaagtt caaaggcaag    1140
gccacactga cttcagacaa atcctccaac acagcctaca tggagctcag cagcctgacc    1200
tctgaggact ctgcggtcta ttactgtgca agagactatg attacgactg gtttgcttac    1260
tggggccagg ggactctggt cactgtctct gcagtcgacg aggtggagg ttctgcggcc    1320 gctcgtggat ctgagaaaga tgagctctaa actcgagggg tagtcaagat gcataataaa    1380
taacggattg tgtccgtaat cacacgtggt gcgtacgata acgcatagtg ttttttccctc   1440 cacttaaatc gaagggttgt gtcttggatc gcgcgggtca aatgtatatg gttcatatac    1500
atccgcaggc acgtaataaa gcgaggggtt cgaatccccc cgttaccccc ggtaggggcc    1560
caggtaccgg cgcgcctcta ga                                             1582

<210> SEQ ID NO 26
<211> LENGTH: 1059
<212> TYPE: DNA
<213> ORGANISM: Artificial Sequence
<220> FEATURE:
<223> OTHER INFORMATION: Description of Artificial Sequence: synthetic,
      no natural origin

<400> SEQUENCE: 26
gaattcgtat ttttacaaca attaccaaca acaacaacaa caacaacatt acaattacta     60
tttacaagga ccatggccca aattgttctc acccagtctc agcaatcat gtctgcatct    120 ccaggggaga aggtcaccat gacctgcagt gccagttcaa gtgtaagtaa aatgcaatgg    180
tatcagcaga agtcaggcac ctcccccaaa agatggattt atgacacatc caaactggcc    240
tctggagtcc ctggtcgctt cagtggcagt gggtctggga cctcttactc tctcacaatc    300
agcagcatgg aggctgaaga tgctgccact tattactgcc agcagtggag tagtaacccg    360
ctcacgttcg gtgctgggac caagctggag ataaaaggct ctactagtgg ttccgggaag    420
agctctgaag gtaaaggtga ggtccagctg cagcagtctg gacctgagct ggtaaatcct    480
ggggcttcag tgaagatgtc ctgcaaggcc tctggataca cattcattac ctatgttatg    540
cactgggtga agcagaagcc tgggcagggc cttgagtgga ttggatatat taatcctaac    600
aaagacggta caaagttcaa tgagaagttc aaaggcaagg ccacactgac ttcagacaaa    660
tcctccaaca cagcctacat ggagctcagc agcctgacct ctgaggactc tgcggtctat    720
tactgtgcaa gagactatga ttacgactgg tttgcttact ggggccaggg gactctggtc    780
actgtctctg cagtcgacgc ggccgctcat caccatcacc atcactagct cgaggggtag    840
tcaagatgca taaataaa cggattgtgt ccgtaatcac acgtggtgcg tacgataacg    900
catagtgttt tccctccac ttaaatcgaa gggttgtgtc ttggatcgcg cgggtcaaat    960
```

```
gtatatggtt catatacatc cgcaggcacg taataaagcg aggggttcga atcccccgt      1020 tacccccggt aggggcccag gtaccggcgc gcctctaga                           1059

<210> SEQ ID NO 27
<211> LENGTH: 1077
<212> TYPE: DNA
<213> ORGANISM: Artificial Sequence
<220> FEATURE:
<223> OTHER INFORMATION: Description of Artificial Sequence: synthetic,
      no natural origin

<400> SEQUENCE: 27
gaattcgtat ttttacaaca attaccaaca acaacaacaa caacaacatt acaattacta      60
tttacaagga ccatggaaat tgttctcacc cagtctccag caatcatgtc tgcatctcca    120
ggggagaagg tcaccatgac ctgcagtgcc agttcaagtg taagtaaaat gcaatggtat    180
cagcagaagt caggcacctc ccccaaaaga tggatttatg acacatccaa actggcctct    240
ggagtccctg gtcgcttcag tggcagtggg tctgggacct cttactctct cacaatcagc    300
agcatggagg ctgaagatgc tgccacttat tactgccagc agtggagtag taacccgctc    360
acgttcggtg ctgggaccaa gctggagata aaaggctcta ctagtggttc cgggaagagc    420
tctgaaggta aggtgaggt ccagctgcag cagtctggac ctgagctggt aaatcctggg    480
gcttcagtga agatgtcctg caaggcctct ggatacacat tcattaccta tgttatgcac    540
tgggtgaagc agaagcctgg gcagggcctt gagtggattg gatatattaa tcctaacaaa    600
gacggtacaa agttcaatga aagttcaaa ggcaaggcca cactgacttc agacaaatcc    660
tccaacacag cctacatgga gctcagcagc ctgacctctg aggactctgc ggtctattac    720
tgtgcaagag actatgatta cgactggttt gcttactggg gccagggac tctggtcact    780 gtctctgcag tcgacggagg tggaggttct gcggccgctc gtggatctga aagatgag    840 ctctagctcg aggggtagtc aagatgcata ataaataacg gattgtgtcc gtaatcacac    900
gtggtgcgta cgataacgca tagtgttttt ccctccactt aaatcgaagg gttgtgtctt    960
ggatcgcgcg ggtcaaatgt atatggttca tatacatccg caggcacgta ataaagcgag   1020
gggttcgaat ccccccgtta ccccccggtag gggcccaggt accggcgcgc ctctaga     1077

<210> SEQ ID NO 28
<211> LENGTH: 1654
<212> TYPE: DNA
<213> ORGANISM: Artificial Sequence
<220> FEATURE:
<223> OTHER INFORMATION: Description of Artificial Sequence: synthetic,
      no natural origin

<400> SEQUENCE: 28
gaattcgtat ttttacaaca attaccaaca acaacaacaa caacaacatt acaattacta      60
tttacaagga ccattatgga ctttcaagtg cagattttca gcttcctcct catcagcgcc    120
tcagttatca tctctagggg atccatggct tacagtatca ctactccatc tcagttcgtg    180
ttcttgtcat cagcgtgggc cgacccaata gagttaatta atttatgtac taatgcctta    240
ggaaatcagt ttcaaacaca acaagctcga actgtcgttc aaagacaatt cagtgaggtg    300 tggaaaccctt caccacaagt aactgttagg ttccctgaca gtgactttaa ggtgtacagg    360
tacaatgcgg tattagaccc gctagtcaca gcactgttag gtgcattcga cactagaaat    420 agaataaatag aagttgaaaa tcaggcgaac cccacgactg ccgaaacgtt agatgctact    480
cgtagagtag acgacgcaac ggtggccata aggagcgcga taaataattt aatagtagaa    540
```

```
ttgatcagag gaaccggatc ttataatcgg agctctttcg agagctcttc tggtttggtt      600
tggacctctg gtcctgcaac tggaggcggc ggaagtggag gtggaggttc tgacgtcgtg      660
ctgacccagt ctccagcaat catgtctgca tctccagggg agaaggtcac catgacctgc      720
agtgccagtt caagtgtaag taaaatgcaa tggtatcagc agaagtcagg cacctccccc      780
aaaagatgga tttatgacac atccaaactg gcctctggag tccctggtcg cttcagtggc      840
agtgggtctg ggacctctta ctctctcaca atcagcagca tggaggctga agatgctgcc      900
acttattact gccagcagtg gagtagtaac ccgctcacgt tcggtgctgg gaccaagctg      960
gagataaaag gctctactag tggttccggg aagagctctg aaggtaaagg tgaggtccag     1020
ctgcagcagt ctggacctga gctggtaaat cctggggctt cagtgaagat gtcctgcaag     1080
gcctctggat acacattcat tacctatgtt atgcactggg tgaagcagaa gcctgggcag     1140
ggccttgagt ggattggata tattaatcct aacaaagacg gtacaaagtt caatgagaag     1200
ttcaaaggca aggccacact gacttcagac aaatcctcca acacagccta catggagctc     1260
agcagcctga cctctgagga ctctgcggtc tattactgtg caagagacta tgattacgac     1320
tggtttgctt actggggcca ggggactctg gtcactgtct ctgcagtcga cggaggtgga     1380
ggttctgcgg ccgctcgtgg atctgagaaa atgagctct aaactcgagg ggtagtcaag     1440
atgcataata aataacggat tgtgtccgta atcacacgtg gtgcgtacga taacgcatag     1500 tgttttccc tccacttaaa tcgaagggtt gtgtcttgga tcgcgcgggt caaatgtata     1560
tggttcatat acatccgcag gcacgtaata aagcgagggg ttcgaatccc cccgttaccc     1620
ccggtagggg cccaggtacc ggcgcgcctc taga                                 1654
```

<210> SEQ ID NO 29
<211> LENGTH: 259
<212> TYPE: PRT
<213> ORGANISM: Artificial Sequence
<220> FEATURE:
<223> OTHER INFORMATION: Description of Artificial Sequence: synthetic,
      no natural origin

<400> SEQUENCE: 29

```
Glu Val His Cys Lys Gln Ser Gly Ala Glu Leu Val Lys Pro Gly Ala
 1               5                  10                  15

Ser Val Lys Leu Ser Cys Arg Ala Ser Asp Tyr Thr Phe Thr Ser Tyr
            20                  25                  30

Tyr Met Tyr Trp Val Lys Gln Arg Pro Gly Gln Gly Leu Glu Trp Ile
        35                  40                  45

Gly Glu Ile Lys Pro Ser Gly Asn Gly Thr Asn Phe Asn Glu Lys Phe
    50                  55                  60

Lys Ser Lys Ala Thr Leu Thr Ser Asp Tyr Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Arg Ser Gly Asn Ala Met Asp Tyr Trp Gly Gln Gly Thr Thr Val
            100                 105                 110

Thr Val Ser Ser Gly Gly Gly Ser Gly Gly Gly Ser Gly Gly
            115                 120                 125

Gly Gly Ser Asp Ile Val Leu Thr Leu Ser Pro Ala Thr Leu Ser Val
        130                 135                 140

Thr Pro Gly Asp Arg Val Ser Leu Ser Cys Arg Ala Ser Gln Ser Ile
145                 150                 155                 160
```

```
Ser Asn Phe Leu His Trp Tyr Gln Gln Lys Ser His Glu Ser Pro Arg
            165                 170                 175

Leu Leu Ile Lys Tyr Thr Ser Gln Ser Ile Ser Gly Ile Pro Ser Thr
            180                 185                 190

Phe Ser Gly Ser Gly Ser Gly Thr Asp Phe Thr Leu Ser Ile Asn Ser
            195                 200                 205

Val Asp Thr Glu Asp Phe Gly Met Tyr Phe Cys Gln Gln Ser Asn Ser
            210                 215                 220

Trp Pro His Arg Phe Gly Ser Gly Ile Lys Leu Glu Leu Lys Ser Ala
225                 230                 235                 240

Val Asp Ala Ala Ala Glu Gln Lys Leu Ile Ser Glu Glu Asp Leu Asn
            245                 250                 255

Gly Ala Ala

<210> SEQ ID NO 30
<211> LENGTH: 267
<212> TYPE: PRT
<213> ORGANISM: Artificial Sequence
<220> FEATURE:
<223> OTHER INFORMATION: Description of Artificial Sequence: synthetic,
      no natural origin

<400> SEQUENCE: 30

Glu Val Lys Leu Gln Gln Ser Gly Ala Glu Leu Val Lys Pro Gly Ala
  1               5                  10                  15

Ser Val Lys Ile Ser Cys Lys Ala Ser Asp Tyr Ser Phe Thr Gly Tyr
             20                  25                  30

Asn Met Asn Trp Val Lys Gln Ser His Gly Lys Ser Leu Glu Trp Ile
         35                  40                  45

Gly Asn Ile Asn Pro Tyr Tyr Gly Ser Thr Ser Tyr Asn Gln Lys Phe
     50                  55                  60

Lys Gly Lys Ala Thr Leu Thr Val Asp Lys Ser Ser Ser Thr Ala Tyr
 65                  70                  75                  80

Met Gln Leu Asn Ser Leu Thr Ser Glu Asp Ser Ala Val Tyr Tyr Cys
                 85                  90                  95

Ala Val Gly Gly Asn Tyr Val Asp Trp Phe Ala Tyr Trp Gly Gln Gly
            100                 105                 110

Thr Leu Val Thr Val Ser Ser Gly Gly Gly Ser Gly Gly Gly Gly
            115                 120                 125

Ser Gly Gly Gly Gly Ser Asp Ile Leu Leu Thr Gln Ser Pro Leu Ser
            130                 135                 140

Leu Pro Val Ser Leu Gly Asp His Ala Ser Ile Ser Cys Arg Ser Ser
145                 150                 155                 160

Gln Ser Leu Val His Ser Asn Gly Asn Thr Tyr Leu His Trp Tyr Leu
            165                 170                 175

Gln Asn Pro Gly Gln Ser Pro Lys Leu Leu Ile Tyr Lys Val Ser Asn
            180                 185                 190

Arg Phe Ser Gly Ile Pro Asp Arg Phe Ser Gly Ser Gly Ser Gly Thr
            195                 200                 205

Asp Phe Thr Leu Lys Ile Ser Arg Val Glu Ala Glu Asp Leu Gly Val
            210                 215                 220

Tyr Phe Cys Ser Gln Ser Thr His Val Pro Tyr Thr Phe Gly Gly Gly
225                 230                 235                 240

Thr Lys Leu Glu Leu Lys Arg Ala Val Asp Ala Ala Ala Glu Gln Lys
            245                 250                 255
```

Leu Ile Ser Glu Glu Asp Leu Asn Gly Ala Ala
          260                 265

<210> SEQ ID NO 31
<211> LENGTH: 58
<212> TYPE: DNA
<213> ORGANISM: Artificial Sequence Sequence
<220> FEATURE:
<223> OTHER INFORMATION: Description of Artificial Sequence: synthetic,
      no natural

<400> SEQUENCE: 31
catgccatga ctcgcggccc agccggccat ggccgakgtr cagcttcagg agtcrgga          58

<210> SEQ ID NO 32
<211> LENGTH: 57
<212> TYPE: DNA
<213> ORGANISM: Artificial Sequence
<220> FEATURE:
<223> OTHER INFORMATION: Description of Artificial Sequence: synthetic,
      no natural origin

<400> SEQUENCE: 32
catgccatga ctcgcggccc agccggccat ggcccaggtg magctgawgg artctgg          57

<210> SEQ ID NO 33
<211> LENGTH: 60
<212> TYPE: DNA
<213> ORGANISM: Artificial Sequence
<220> FEATURE:
<223> OTHER INFORMATION: Description of Artificial Sequence: synthetic,
      no natural origin

<400> SEQUENCE: 33
catgccatga ctcgcggccc agccggccat ggccgaggtc cagctrcarc artctggacc          60

<210> SEQ ID NO 34
<211> LENGTH: 56
<212> TYPE: DNA
<213> ORGANISM: Artificial Sequence
<220> FEATURE:
<223> OTHER INFORMATION: Description of Artificial Sequence: synthetic,
      no natural origin

<400> SEQUENCE: 34
catgccatga ctcgcggccc agccggccat ggcccaggtw cagctscagc agtctg          56

<210> SEQ ID NO 35
<211> LENGTH: 58
<212> TYPE: DNA
<213> ORGANISM: Artificial Sequence
<220> FEATURE:
<223> OTHER INFORMATION: Description of Artificial Sequence: synthetic,
      no natural

<400> SEQUENCE: 35
catgccatga ctcgcggccc agccggccat ggccsaggtc carctgcags aryctggr          58

<210> SEQ ID NO 36
<211> LENGTH: 58
<212> TYPE: DNA
<213> ORGANISM: Artificial Sequence
<220> FEATURE:
<223> OTHER INFORMATION: Description of Artificial Sequence: synthetic,
      no natural

<400> SEQUENCE: 36

```
catgccatga ctcgcggccc agccggccat ggccgaggtt cagctgcagc agtctggg        58

<210> SEQ ID NO 37
<211> LENGTH: 58
<212> TYPE: DNA
<213> ORGANISM: Artificial Sequence
<220> FEATURE:
<223> OTHER INFORMATION: Description of Artificial Sequence: synthetic,
      no natural

<400> SEQUENCE: 37
catgccatga ctcgcggccc agccggccat ggccgargtg aagctggtgg artctggr       58

<210> SEQ ID NO 38
<211> LENGTH: 58
<212> TYPE: DNA
<213> ORGANISM: Artificial Sequence
<220> FEATURE:
<223> OTHER INFORMATION: Description of Artificial Sequence: synthetic,
      no natural

<400> SEQUENCE: 38
catgccatga ctcgcggccc agccggccat ggccgaggtg aagstymtcg agtctgga       58

<210> SEQ ID NO 39
<211> LENGTH: 57
<212> TYPE: DNA
<213> ORGANISM: Artificial Sequence
<220> FEATURE:
<223> OTHER INFORMATION: Description of Artificial Sequence: synthetic,
      no natural

<400> SEQUENCE: 39
catgccatga ctcgcggccc agccggccat ggccgargtg aagctkgakg agwctgr        57

<210> SEQ ID NO 40
<211> LENGTH: 58
<212> TYPE: DNA
<213> ORGANISM: Artificial Sequence
<220> FEATURE:
<223> OTHER INFORMATION: Description of Artificial Sequence: synthetic,
      no natural

<400> SEQUENCE: 40
catgccatga ctcgcggccc agccggccat ggccgavgtg mwgctkgtgg agtctggk       58

<210> SEQ ID NO 41
<211> LENGTH: 59
<212> TYPE: DNA
<213> ORGANISM: Artificial Sequence
<220> FEATURE:
<223> OTHER INFORMATION: Description of Artificial Sequence: synthetic,
      no natural

<400> SEQUENCE: 41
catgccatga ctcgcggccc agccggccat ggccgaggtg carctkgttg agtctggtg      59

<210> SEQ ID NO 42
<211> LENGTH: 58
<212> TYPE: DNA
<213> ORGANISM: Artificial Sequence
<220> FEATURE:
<223> OTHER INFORMATION: Description of Artificial Sequence: synthetic,
      no natural

<400> SEQUENCE: 42
```
catgccatga ctcgcggccc agccggccat ggccsaggty cagctkcagc agtctgga        58

<210> SEQ ID NO 43
<211> LENGTH: 58
<212> TYPE: DNA
<213> ORGANISM: Artificial Sequence
<220> FEATURE:
<223> OTHER INFORMATION: Description of Artificial Sequence: synthetic,
      no natural

<400> SEQUENCE: 43
catgccatga ctcgcggccc agccggccat ggcccagatc cagttggtgc agtctgga        58

<210> SEQ ID NO 44
<211> LENGTH: 58
<212> TYPE: DNA
<213> ORGANISM: Artificial Sequence
<220> FEATURE:
<223> OTHER INFORMATION: Description of Artificial Sequence: synthetic,
      no natural

<400> SEQUENCE: 44
catgccatga ctcgcggccc agccggccat ggcccaggts cacstgrwgs agtctggg        58

<210> SEQ ID NO 45
<211> LENGTH: 49
<212> TYPE: DNA
<213> ORGANISM: Artificial Sequence
<220> FEATURE:
<223> OTHER INFORMATION: Description of Artificial Sequence: synthetic,
      no natural

<400> SEQUENCE: 45
caggtscacs tgrwgsagtc tgggcaggtt actctraaag wgtstggcc                  49

<210> SEQ ID NO 46
<211> LENGTH: 57
<212> TYPE: DNA
<213> ORGANISM: Artificial Sequence
<220> FEATURE:
<223> OTHER INFORMATION: Description of Artificial Sequence: synthetic,
      no natural

<400> SEQUENCE: 46
catgccatga ctcgcggccc agccggccat ggccgatgtg aacttggaag tgtctgg         57

<210> SEQ ID NO 47
<211> LENGTH: 48
<212> TYPE: DNA
<213> ORGANISM: Artificial Sequence
<220> FEATURE:
<223> OTHER INFORMATION: Description of Artificial Sequence: synthetic,
      no natural

<400> SEQUENCE: 47
catgccatga ctcgcggcgc gcctgacatt gtgmtgwchc agtctcca                   48

<210> SEQ ID NO 48
<211> LENGTH: 47
<212> TYPE: DNA
<213> ORGANISM: Artificial Sequence
<220> FEATURE:
<223> OTHER INFORMATION: Description of Artificial Sequence: synthetic,
      no natural

<400> SEQUENCE: 48
catgccatga ctcgcggcgc gcctgacatt cagatgattc agtctcc                    47

<210> SEQ ID NO 49
<211> LENGTH: 47
<212> TYPE: DNA
<213> ORGANISM: Artificial Sequence
<220> FEATURE:
<223> OTHER INFORMATION: Description of Artificial Sequence: synthetic, no natural

<400> SEQUENCE: 49
catgccatga ctcgcggcgc gcctgacatt gttctcwhcc agtctcc                47

<210> SEQ ID NO 50
<211> LENGTH: 48
<212> TYPE: DNA
<213> ORGANISM: Artificial Sequence
<220> FEATURE:
<223> OTHER INFORMATION: Description of Artificial Sequence: synthetic, no natural

<400> SEQUENCE: 50
catgccatga ctcgcggcgc gcctgacatt gtgmtgwchc agtctcaa               48

<210> SEQ ID NO 51
<211> LENGTH: 48
<212> TYPE: DNA
<213> ORGANISM: Artificial Sequence
<220> FEATURE:
<223> OTHER INFORMATION: Description of Artificial Sequence: synthetic, no natural

<400> SEQUENCE: 51
catgccatga ctcgcggcgc gcctgatrtt ktgatgaccc arrckgca               48

<210> SEQ ID NO 52
<211> LENGTH: 48
<212> TYPE: DNA
<213> ORGANISM: Artificial Sequence
<220> FEATURE:
<223> OTHER INFORMATION: Description of Artificial Sequence: synthetic, no natural

<400> SEQUENCE: 52
catgccatga ctcgcggcgc gcctgatrtt ktgatgaccc arrckcca               48

<210> SEQ ID NO 53
<211> LENGTH: 46
<212> TYPE: DNA
<213> ORGANISM: Artificial Sequence
<220> FEATURE:
<223> OTHER INFORMATION: Description of Artificial Sequence: synthetic, no natural

<400> SEQUENCE: 53
catgccatga ctcgcggcgc gcctgacatt gtgatgaccc arbhtg                 46

<210> SEQ ID NO 54
<211> LENGTH: 47
<212> TYPE: DNA
<213> ORGANISM: Artificial Sequence
<220> FEATURE:
<223> OTHER INFORMATION: Description of Artificial Sequence: synthetic, no natural

<400> SEQUENCE: 54
catgccatga ctcgcggcgc gcctgatatt ktgatgaccc araytcc                47

```
<210> SEQ ID NO 55
<211> LENGTH: 48
<212> TYPE: DNA
<213> ORGANISM: Artificial Sequence
<220> FEATURE:
<223> OTHER INFORMATION: Description of Artificial Sequence: synthetic,
      no natural

<400> SEQUENCE: 55
catgccatga ctcgcggcgc gcctramatt gtgmtgaccc aatytccw                    48

<210> SEQ ID NO 56
<211> LENGTH: 48
<212> TYPE: DNA
<213> ORGANISM: Artificial Sequence
<220> FEATURE:
<223> OTHER INFORMATION: Description of Artificial Sequence: synthetic,
      no natural

<400> SEQUENCE: 56
catgccatga ctcgcggcgc gcctsaaawt gtkctsaccc agtctcca                    48

<210> SEQ ID NO 57
<211> LENGTH: 47
<212> TYPE: DNA
<213> ORGANISM: Artificial Sequence
<220> FEATURE:
<223> OTHER INFORMATION: Description of Artificial Sequence: synthetic,
      no natural

<400> SEQUENCE: 57
catgccatga ctcgcggcgc gcctgayaty cagatgacmc agwctac                     47

<210> SEQ ID NO 58
<211> LENGTH: 47
<212> TYPE: DNA
<213> ORGANISM: Artificial Sequence
<220> FEATURE:
<223> OTHER INFORMATION: Description of Artificial Sequence: synthetic,
      no natural

<400> SEQUENCE: 58
catgccatga ctcgcggcgc gcctgayaty cagatgachc agwctcc                     47

<210> SEQ ID NO 59
<211> LENGTH: 47
<212> TYPE: DNA
<213> ORGANISM: Artificial Sequence
<220> FEATURE:
<223> OTHER INFORMATION: Description of Artificial Sequence: synthetic,
      no natural

<400> SEQUENCE: 59
catgccatga ctcgcggcgc gcctgacatt gtgatgactc aggctac                     47

<210> SEQ ID NO 60
<211> LENGTH: 46
<212> TYPE: DNA
<213> ORGANISM: Artificial Sequence
<220> FEATURE:
<223> OTHER INFORMATION: Description of Artificial Sequence: synthetic,
      no natural

<400> SEQUENCE: 60
catgccatga ctcgcggcgc gcctcarsyt gtkstsactc agkaat                      46
```

```
<210> SEQ ID NO 61
<211> LENGTH: 46
<212> TYPE: DNA
<213> ORGANISM: Artificial Sequence
<220> FEATURE:
<223> OTHER INFORMATION: Description of Artificial Sequence: synthetic,
      no natural

<400> SEQUENCE: 61
catgccatga ctcgcggcgc gcctcarsyt gtkstsactc agkcat                      46

<210> SEQ ID NO 62
<211> LENGTH: 47
<212> TYPE: DNA
<213> ORGANISM: Artificial Sequence
<220> FEATURE:
<223> OTHER INFORMATION: Description of Artificial Sequence: synthetic,
      no natural

<400> SEQUENCE: 62
ctagtggtac tccacggccg gccccctgmrg agacdgtgas mgtrgtc                    47

<210> SEQ ID NO 63
<211> LENGTH: 47
<212> TYPE: DNA
<213> ORGANISM: Artificial Sequence
<220> FEATURE:
<223> OTHER INFORMATION: Description of Artificial Sequence: synthetic,
      no natural

<400> SEQUENCE: 63
ctagtggtac tccacggccg gccccctgmrg agacdgtgas rgtrgtg                    47

<210> SEQ ID NO 64
<211> LENGTH: 47
<212> TYPE: DNA
<213> ORGANISM: Artificial Sequence
<220> FEATURE:
<223> OTHER INFORMATION: Description of Artificial Sequence: synthetic,
      no natural

<400> SEQUENCE: 64
ctagtggtac tccacggccg gccccctgmrg agacdgtgas cagrgtc                    47

<210> SEQ ID NO 65
<211> LENGTH: 47
<212> TYPE: DNA
<213> ORGANISM: Artificial Sequence
<220> FEATURE:
<223> OTHER INFORMATION: Description of Artificial Sequence: synthetic,
      no natural

<400> SEQUENCE: 65
ctagtggtac tccacggccg gccccctgmrg agacdgtgas tgaggtt                    47

<210> SEQ ID NO 66
<211> LENGTH: 47
<212> TYPE: DNA
<213> ORGANISM: Artificial Sequence
<220> FEATURE:
<223> OTHER INFORMATION: Description of Artificial Sequence: synthetic,
      no natural

<400> SEQUENCE: 66
ctagtggtac tccacggccg gccccctgmrg agacdgtgas tgarattt                   47

<210> SEQ ID NO 67
<211> LENGTH: 50
```

```
<212> TYPE: DNA
<213> ORGANISM: Artificial Sequence
<220> FEATURE:
<223> OTHER INFORMATION: Description of Artificial Sequence: synthetic,
      no natural

<400> SEQUENCE: 67
ctagtggtac tccacgcggc cgcgtcgaca gcmcgtttca gytccarytt         50

<210> SEQ ID NO 68
<211> LENGTH: 50
<212> TYPE: DNA
<213> ORGANISM: Artificial Sequence
<220> FEATURE:
<223> OTHER INFORMATION: Description of Artificial Sequence: synthetic,
      no natural

<400> SEQUENCE: 68
ctagtggtac tccacgcggc cgcgtcgaca gcmcgtttka tytccarytt         50

<210> SEQ ID NO 69
<211> LENGTH: 53
<212> TYPE: DNA
<213> ORGANISM: Artificial Sequence
<220> FEATURE:
<223> OTHER INFORMATION: Description of Artificial Sequence: synthetic,
      no natural

<400> SEQUENCE: 69
ctagtggtac tccacgcggc cgcgtcgaca gcmcgtttba kytctatctt tgt     53

<210> SEQ ID NO 70
<211> LENGTH: 56
<212> TYPE: DNA
<213> ORGANISM: Artificial Sequence
<220> FEATURE:
<223> OTHER INFORMATION: Description of Artificial Sequence: synthetic,
      no natural

<400> SEQUENCE: 70
ctagtggtac tccacgcggc cgcgtcgaca gcmcgagcmc gttttatttc caamkt  56

<210> SEQ ID NO 71
<211> LENGTH: 53
<212> TYPE: DNA
<213> ORGANISM: Artificial Sequence
<220> FEATURE:
<223> OTHER INFORMATION: Description of Artificial Sequence: synthetic,
      no natural

<400> SEQUENCE: 71
ctagtggtac tccacgcggc cgcgtcgacc tgrcctagga cagtsasytt ggt     53

<210> SEQ ID NO 72
<220> FEATURE:
<223> OTHER INFORMATION: Description of Artificial Sequence: synthetic,
      no natural origin
<211> LENGTH:
<212> TYPE:
<213> ORGANISM:

<400> SEQUENCE: 72

000

<210> SEQ ID NO 73
<220> FEATURE:
<223> OTHER INFORMATION: Description of Artificial Sequence: synthetic,
```

```
        no natural origin
<211> LENGTH:
<212> TYPE:
<213> ORGANISM:

<400> SEQUENCE: 73

000

<210> SEQ ID NO 74
<220> FEATURE:
<223> OTHER INFORMATION: Description of Artificial Sequence: synthetic,
      no natural origin
<211> LENGTH:
<212> TYPE:
<213> ORGANISM:

<400> SEQUENCE: 74

000

<210> SEQ ID NO 75
<220> FEATURE:
<223> OTHER INFORMATION: Description of Artificial Sequence: synthetic,
      no natural origin
<211> LENGTH:
<212> TYPE:
<213> ORGANISM:

<400> SEQUENCE: 75

000

<210> SEQ ID NO 76
<220> FEATURE:
<223> OTHER INFORMATION: Description of Artificial Sequence: synthetic,
      no natural origin
<211> LENGTH:
<212> TYPE:
<213> ORGANISM:

<400> SEQUENCE: 76

000

<210> SEQ ID NO 77
<220> FEATURE:
<223> OTHER INFORMATION: Description of Artificial Sequence: synthetic,
      no natural origin
<211> LENGTH:
<212> TYPE:
<213> ORGANISM:

<400> SEQUENCE: 77

000

<210> SEQ ID NO 78
<220> FEATURE:
<223> OTHER INFORMATION: Description of Artificial Sequence: synthetic,
      no natural origin
<211> LENGTH:
<212> TYPE:
<213> ORGANISM:

<400> SEQUENCE: 78

000

<210> SEQ ID NO 79
<220> FEATURE:
<223> OTHER INFORMATION: Description of Artificial Sequence: synthetic,
      no natural origin
```

```
<211> LENGTH:
<212> TYPE:
<213> ORGANISM:

<400> SEQUENCE: 79

000

<210> SEQ ID NO 80
<220> FEATURE:
<223> OTHER INFORMATION: Description of Artificial Sequence: synthetic,
      no natural origin
<211> LENGTH:
<212> TYPE:
<213> ORGANISM:

<400> SEQUENCE: 80

000

<210> SEQ ID NO 81
<220> FEATURE:
<223> OTHER INFORMATION: Description of Artificial Sequence: synthetic,
      no natural origin
<211> LENGTH:
<212> TYPE:
<213> ORGANISM:

<400> SEQUENCE: 81

000

<210> SEQ ID NO 82
<220> FEATURE:
<223> OTHER INFORMATION: Description of Artificial Sequence: synthetic,
      no natural origin
<211> LENGTH:
<212> TYPE:
<213> ORGANISM:

<400> SEQUENCE: 82

000

<210> SEQ ID NO 83
<220> FEATURE:
<223> OTHER INFORMATION: Description of Artificial Sequence: synthetic,
      no natural origin
<211> LENGTH:
<212> TYPE:
<213> ORGANISM:

<400> SEQUENCE: 83

000

<210> SEQ ID NO 84
<220> FEATURE:
<223> OTHER INFORMATION: Description of Artificial Sequence: synthetic,
      no natural origin
<211> LENGTH:
<212> TYPE:
<213> ORGANISM:

<400> SEQUENCE: 84

000

<210> SEQ ID NO 85
<220> FEATURE:
<223> OTHER INFORMATION: Description of Artificial Sequence: synthetic,
      no natural origin
<211> LENGTH:
```

```
<212> TYPE:
<213> ORGANISM:

<400> SEQUENCE: 85

000

<210> SEQ ID NO 86
<220> FEATURE:
<223> OTHER INFORMATION: Description of Artificial Sequence: synthetic,
      no natural origin
<211> LENGTH:
<212> TYPE:
<213> ORGANISM:

<400> SEQUENCE: 86

000

<210> SEQ ID NO 87
<220> FEATURE:
<223> OTHER INFORMATION: Description of Artificial Sequence: synthetic,
      no natural origin
<211> LENGTH:
<212> TYPE:
<213> ORGANISM:

<400> SEQUENCE: 87

000

<210> SEQ ID NO 88
<220> FEATURE:
<223> OTHER INFORMATION: Description of Artificial Sequence: synthetic,
      no natural origin
<211> LENGTH:
<212> TYPE:
<213> ORGANISM:

<400> SEQUENCE: 88

000

<210> SEQ ID NO 89
<220> FEATURE:
<223> OTHER INFORMATION: Description of Artificial Sequence: synthetic,
      no natural origin
<211> LENGTH:
<212> TYPE:
<213> ORGANISM:

<400> SEQUENCE: 89

000

<210> SEQ ID NO 90
<220> FEATURE:
<223> OTHER INFORMATION: Description of Artificial Sequence: synthetic,
      no natural origin
<211> LENGTH:
<212> TYPE:
<213> ORGANISM:

<400> SEQUENCE: 90

000

<210> SEQ ID NO 91
<220> FEATURE:
<223> OTHER INFORMATION: Description of Artificial Sequence: synthetic,
      no natural origin
<211> LENGTH:
<212> TYPE:
```

-continued

```
<213> ORGANISM:

<400> SEQUENCE: 91

000

<210> SEQ ID NO 92
<220> FEATURE:
<223> OTHER INFORMATION: Description of Artificial Sequence: synthetic,
      no natural origin
<211> LENGTH:
<212> TYPE:
<213> ORGANISM:

<400> SEQUENCE: 92

000

<210> SEQ ID NO 93
<220> FEATURE:
<223> OTHER INFORMATION: Description of Artificial Sequence: synthetic,
      no natural origin
<211> LENGTH:
<212> TYPE:
<213> ORGANISM:

<400> SEQUENCE: 93

000

<210> SEQ ID NO 94
<220> FEATURE:
<223> OTHER INFORMATION: Description of Artificial Sequence: synthetic,
      no natural origin
<211> LENGTH:
<212> TYPE:
<213> ORGANISM:

<400> SEQUENCE: 94

000

<210> SEQ ID NO 95
<220> FEATURE:
<223> OTHER INFORMATION: Description of Artificial Sequence: synthetic,
      no natural origin
<211> LENGTH:
<212> TYPE:
<213> ORGANISM:

<400> SEQUENCE: 95

000

<210> SEQ ID NO 96
<220> FEATURE:
<223> OTHER INFORMATION: Description of Artificial Sequence: synthetic,
      no natural origin
<211> LENGTH:
<212> TYPE:
<213> ORGANISM:

<400> SEQUENCE: 96

000

<210> SEQ ID NO 97
<220> FEATURE:
<223> OTHER INFORMATION: Description of Artificial Sequence: synthetic,
      no natural origin
<211> LENGTH:
<212> TYPE:
<213> ORGANISM:
```

-continued

```
<400> SEQUENCE: 97

000

<210> SEQ ID NO 98
<220> FEATURE:
<223> OTHER INFORMATION: Description of Artificial Sequence: synthetic,
      no natural origin
<211> LENGTH:
<212> TYPE:
<213> ORGANISM:

<400> SEQUENCE: 98

000

<210> SEQ ID NO 99
<220> FEATURE:
<223> OTHER INFORMATION: Description of Artificial Sequence: synthetic,
      no natural origin
<211> LENGTH:
<212> TYPE:
<213> ORGANISM:

<400> SEQUENCE: 99

000

<210> SEQ ID NO 100
<220> FEATURE:
<223> OTHER INFORMATION: Description of Artificial Sequence: synthetic,
      no natural origin
<211> LENGTH:
<212> TYPE:
<213> ORGANISM:

<400> SEQUENCE: 100

000

<210> SEQ ID NO 101
<220> FEATURE:
<223> OTHER INFORMATION: Description of Artificial Sequence: synthetic,
      no natural origin
<211> LENGTH:
<212> TYPE:
<213> ORGANISM:

<400> SEQUENCE: 101

000

<210> SEQ ID NO 102
<220> FEATURE:
<223> OTHER INFORMATION: Description of Artificial Sequence: synthetic,
      no natural origin
<211> LENGTH:
<212> TYPE:
<213> ORGANISM:

<400> SEQUENCE: 102

000

<210> SEQ ID NO 103
<220> FEATURE:
<223> OTHER INFORMATION: Description of Artificial Sequence: synthetic,
      no natural origin
<211> LENGTH:
<212> TYPE:
<213> ORGANISM:
```

```
<400> SEQUENCE: 103

000

<210> SEQ ID NO 104
<220> FEATURE:
<223> OTHER INFORMATION: Description of Artificial Sequence: synthetic,
      no natural origin
<211> LENGTH:
<212> TYPE:
<213> ORGANISM:

<400> SEQUENCE: 104

000

<210> SEQ ID NO 105
<220> FEATURE:
<223> OTHER INFORMATION: Description of Artificial Sequence: synthetic,
      no natural origin
<211> LENGTH:
<212> TYPE:
<213> ORGANISM:

<400> SEQUENCE: 105

000

<210> SEQ ID NO 106
<220> FEATURE:
<223> OTHER INFORMATION: Description of Artificial Sequence: synthetic,
      no natural origin
<211> LENGTH:
<212> TYPE:
<213> ORGANISM:

<400> SEQUENCE: 106

000

<210> SEQ ID NO 107
<220> FEATURE:
<223> OTHER INFORMATION: Description of Artificial Sequence: synthetic,
      no natural origin
<211> LENGTH:
<212> TYPE:
<213> ORGANISM:

<400> SEQUENCE: 107

000

<210> SEQ ID NO 108
<220> FEATURE:
<223> OTHER INFORMATION: Description of Artificial Sequence: synthetic,
      no natural origin
<211> LENGTH:
<212> TYPE:
<213> ORGANISM:

<400> SEQUENCE: 108

000

<210> SEQ ID NO 109
<220> FEATURE:
<223> OTHER INFORMATION: Description of Artificial Sequence: synthetic,
      no natural origin
<211> LENGTH:
<212> TYPE:
<213> ORGANISM:

<400> SEQUENCE: 109
```

000

<210> SEQ ID NO 110
<220> FEATURE:
<223> OTHER INFORMATION: Description of Artificial Sequence: synthetic,
      no natural origin
<211> LENGTH:
<212> TYPE:
<213> ORGANISM:

<400> SEQUENCE: 110

000

<210> SEQ ID NO 111
<220> FEATURE:
<223> OTHER INFORMATION: Description of Artificial Sequence: synthetic,
      no natural origin
<211> LENGTH:
<212> TYPE:
<213> ORGANISM:

<400> SEQUENCE: 111

000

<210> SEQ ID NO 112
<220> FEATURE:
<223> OTHER INFORMATION: Description of Artificial Sequence: synthetic,
      no natural origin
<211> LENGTH:
<212> TYPE:
<213> ORGANISM:

<400> SEQUENCE: 112

000

<210> SEQ ID NO 113
<211> LENGTH: 257
<212> TYPE: PRT
<213> ORGANISM: Artificial Sequence
<220> FEATURE:
<223> OTHER INFORMATION: Description of Artificial Sequence: synthetic,
      no natural origin

<400> SEQUENCE: 113

```
Met Ala Glu Val Gln Leu Gln Gln Ser Gly Ala Glu Leu Val Lys Pro
 1               5                  10                  15
Gly Ala Ser Val Lys Met Ser Cys Lys Ala Ser Gly Tyr Thr Phe Thr
            20                  25                  30
Asn Tyr Asn Met His Trp Val Lys Gln Thr Pro Gly Gln Gly Leu Glu
        35                  40                  45
Trp Ile Gly Ala Ile Tyr Pro Arg Asn Gly Asp Thr Ser Tyr Asn Gln
    50                  55                  60
Lys Phe Lys Gly Lys Ala Thr Leu Thr Ala Asp Lys Ser Ser Ser Thr
65                  70                  75                  80
Ala Tyr Met Gln Leu Ser Ser Leu Thr Ser Glu Asp Ser Ala Val Tyr
                85                  90                  95
Tyr Cys Ala Arg Pro Asp Val Trp Gly Ala Gly Thr Leu Leu Thr Val
            100                 105                 110
Ser Ala Gly Ala Gly Pro Thr Ser Gly Ser Gly Lys Pro Gly Pro Gly
        115                 120                 125
Glu Gly Ser Thr Lys Gly Ala Pro Asp Val Leu Met Thr Gln Ala Pro
    130                 135                 140
```

-continued

Leu Thr Leu Ser Val Thr Ile Gly Gln Pro Ala Ser Ile Ser Cys Lys
145                 150                 155                 160

Ser Ser Gln Ser Leu Leu Asp Gly Asp Gly Lys Thr Tyr Leu Asn Trp
                165                 170                 175

Leu Leu Gln Arg Pro Gly Gln Ser Pro Lys Arg Leu Ile Tyr Leu Val
            180                 185                 190

Ser Lys Leu Asp Ser Gly Val Pro Asp Arg Phe Thr Gly Ser Gly Ser
        195                 200                 205

Gly Thr Asp Phe Thr Leu Lys Ile Ser Arg Val Glu Ala Glu Asp Leu
    210                 215                 220

Gly Val Tyr Tyr Cys Trp Gln Gly Thr His Phe Pro His Thr Phe Gly
225                 230                 235                 240

Gly Gly Thr Lys Leu Glu Ile Lys Arg Ala Arg Ala Val Asp Ala Ala
                245                 250                 255

Ala

<210> SEQ ID NO 114
<211> LENGTH: 259
<212> TYPE: PRT
<213> ORGANISM: Artificial Sequence
<220> FEATURE:
<223> OTHER INFORMATION: Description of Artificial Sequence: synthetic,
      no natural origin

<400> SEQUENCE: 114

Met Ala Gln Val Thr Leu Lys Glu Ser Gly Pro Gly Ile Leu Lys Pro
1               5                   10                  15

Ser Gln Thr Leu Ser Leu Thr Cys Ser Phe Ser Gly Phe Ser Leu Ser
                20                  25                  30

Thr Ser Gly Met Gly Val Gly Trp Ile Arg Gln Pro Ser Gly Lys Gly
            35                  40                  45

Leu Glu Trp Leu Ala His Ile Trp Trp Asp Asp Lys Tyr Tyr Asn
        50                  55                  60

Pro Ser Leu Arg Ser Gln Leu Thr Ile Ser Lys Asp Thr Ser Arg Asn
65                  70                  75                  80

Gln Val Phe Leu Arg Ile Thr Asn Val Asp Thr Ala Asp Thr Ala Thr
                85                  90                  95

Tyr Tyr Cys Ala Arg Gly Tyr Tyr Gly Asn Asp Ser Pro Phe Ala Tyr
            100                 105                 110

Trp Gly Gln Gly Thr Leu Leu Thr Val Ser Ser Gly Ala Gly Pro Thr
        115                 120                 125

Ser Gly Ser Gly Lys Pro Gly Pro Gly Glu Gly Ser Thr Lys Gly Ala
    130                 135                 140

Pro Asp Ile Val Leu Ser Gln Ser Pro Lys Phe Met Ser Thr Ser Val
145                 150                 155                 160

Gly Asp Arg Val Ser Ile Thr Cys Lys Ala Ser Gln Ile Val Arg Thr
                165                 170                 175

Ala Val Ala Trp Phe Gln Gln Lys Pro Gly Gln Ser Pro Lys Ala Leu
            180                 185                 190

Ile Tyr Leu Ala Ser Asn Arg His Thr Gly Val Pro Asp Arg Phe Thr
        195                 200                 205

Gly Ser Gly Ser Gly Thr Asp Phe Thr Leu Thr Ile Ser Asn Val Gln
    210                 215                 220

Ser Glu Asp Leu Ala Asp Tyr Phe Cys Leu Gln His Trp Asn Tyr Pro
225                 230                 235                 240

```
Phe Thr Phe Gly Ser Gly Thr Lys Leu Glu Ile Lys Arg Ala Val Asp
            245                 250                 255

Ala Ala Ala
```

<210> SEQ ID NO 115
<211> LENGTH: 259
<212> TYPE: PRT
<213> ORGANISM: Artificial Sequence
<220> FEATURE:
<223> OTHER INFORMATION: Description of Artificial Sequence: synthetic, no natural origin

<400> SEQUENCE: 115

```
Met Ala Gln Ile Gln Leu Val Gln Ser Gly Pro Glu Leu Lys Lys Pro
 1               5                  10                  15

Gly Gln Thr Val Lys Ile Ser Cys Lys Ala Ser Ala Tyr Thr Phe Thr
            20                  25                  30

Asp Tyr Ser Met His Trp Val Lys Gln Ala Pro Gly Lys Gly Leu Lys
        35                  40                  45

Trp Met Gly Trp Ile Asn Thr Glu Thr Gly Glu Pro Thr Tyr Ala Asp
 50                  55                  60

Asp Phe Lys Gly Arg Phe Ala Phe Ser Leu Glu Thr Ser Ala Ser Thr
 65                  70                  75                  80

Ala Tyr Leu Gln Ile Asn Thr Leu Lys Asn Glu Asp Ser Ala Thr Tyr
                85                  90                  95

Phe Cys Ala Arg Gly Ser Gly Phe Asn Pro Tyr Trp Gly Gln Gly Thr
            100                 105                 110

Leu Val Thr Val Ser Ala Gly Ala Gly Pro Thr Ser Gly Ser Gly Lys
        115                 120                 125

Pro Gly Pro Gly Glu Gly Ser Thr Lys Gly Ala Pro Asp Ile Val Leu
130                 135                 140

Ser Gln Ser Pro Ser Ser Leu Ala Val Ser Val Gly Glu Lys Val Thr
145                 150                 155                 160

Met Ser Cys Lys Ser Ser Gln Ser Leu Leu Tyr Ser Ser Asn Gln Lys
                165                 170                 175

Asn Tyr Leu Ala Trp Tyr Gln Gln Lys Pro Gly Gln Ser Pro Lys Leu
            180                 185                 190

Leu Ile Tyr Trp Ala Ser Thr Arg Glu Ser Gly Val Pro Asp Arg Phe
        195                 200                 205

Thr Gly Ser Gly Ser Gly Thr Asp Phe Thr Leu Thr Ile Asn Ser Val
    210                 215                 220

Lys Ala Glu Asp Leu Ala Val Tyr Tyr Cys Gln Gln Tyr Tyr Ser Tyr
225                 230                 235                 240

Val Thr Phe Gly Ala Gly Thr Lys Leu Glu Ile Lys Arg Ala Val Asp
                245                 250                 255

Ala Ala Ala
```

<210> SEQ ID NO 116
<211> LENGTH: 12
<212> TYPE: PRT
<213> ORGANISM: Artificial Sequence
<220> FEATURE:
<223> OTHER INFORMATION: Description of Artificial Sequence: synthetic, no natural origin

<400> SEQUENCE: 116

Asn Leu Ile Val Glu Leu Ile Arg Gly Thr Gly Ser

```
                1               5               10

<210> SEQ ID NO 117
<211> LENGTH: 8
<212> TYPE: PRT
<213> ORGANISM: Artificial Sequence
<220> FEATURE:
<223> OTHER INFORMATION: Description of Artificial Sequence: synthetic,
      no natural origin
<220> FEATURE:
<221> NAME/KEY: misc
<222> LOCATION: (5)..(5)
<223> OTHER INFORMATION: X is Val or Cys

<400> SEQUENCE: 117

Lys Thr Asp Leu Xaa Arg Ala Thr
1               5

<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence: synthetic,
      no natural origin

<400> SEQUENCE: 118

Arg Ile Val Ile Cys Gly Arg Val Thr
1               5

<210> SEQ ID NO 119
<211> LENGTH: 8
<212> TYPE: PRT
<213> ORGANISM: Artificial Sequence
<220> FEATURE:
<223> OTHER INFORMATION: Description of Artificial Sequence: synthetic,
      no natural origin
<220> FEATURE:
<221> NAME/KEY: misc_feature
<222> LOCATION: (5)..(5)
<223> OTHER INFORMATION: Xaa is Pro or Ala

<400> SEQUENCE: 119

Arg Gly Thr Leu Xaa Arg Gly Thr
1               5

<210> SEQ ID NO 120
<211> LENGTH: 9
<212> TYPE: PRT
<213> ORGANISM: Artificial Sequence
<220> FEATURE:
<223> OTHER INFORMATION: Description of Artificial Sequence: synthetic,
      no natural origin

<400> SEQUENCE: 120

Val Gly Arg Gln Arg Asp Thr Gln Ser
1               5

<210> SEQ ID NO 121
<211> LENGTH: 9
<212> TYPE: PRT
<213> ORGANISM: Artificial Sequence
<220> FEATURE:
<223> OTHER INFORMATION: Description of Artificial Sequence: synthetic,
      no
      natural origin

<400> SEQUENCE: 121

Phe Leu Arg Val Asp Ala Arg Glu Thr
```

-continued

```
<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence: synthetic,
      no
      natural origin

<400> SEQUENCE: 122

Val Ala Gly Met Leu Gly Lys Gly Thr
 1               5

<210> SEQ ID NO 123
<211> LENGTH: 8
<212> TYPE: PRT
<213> ORGANISM: Artificial Sequence
<220> FEATURE:
<223> OTHER INFORMATION: Description of Artificial Sequence: synthetic,
      no natural origin
<220> FEATURE:
<221> NAME/KEY: misc_feature
<222> LOCATION: (5)..(5)
<223> OTHER INFORMATION: Xaa is Ala or Asn

<400> SEQUENCE: 123

Arg Trp Glu Leu Xaa Arg Ser Thr
 1               5

<210> SEQ ID NO 124
<211> LENGTH: 8
<212> TYPE: PRT
<213> ORGANISM: Artificial Sequence
<220> FEATURE:
<223> OTHER INFORMATION: Description of Artificial Sequence: synthetic,
      no natural origin
<220> FEATURE:
<221> NAME/KEY: misc_feature
<222> LOCATION: (5)..(5)
<223> OTHER INFORMATION: Xaa is Gly or Thr

<400> SEQUENCE: 124

Pro Ser Ala Leu Xaa Arg Glu Thr
 1               5

<210> SEQ ID NO 125
<211> LENGTH: 8
<212> TYPE: PRT
<213> ORGANISM: Artificial Sequence
<220> FEATURE:
<223> OTHER INFORMATION: Description of Artificial Sequence: synthetic,
      no natural origin
<220> FEATURE:
<221> NAME/KEY: misc_feature
<222> LOCATION: (5)..(5)
<223> OTHER INFORMATION: Xaa is Val or Ser

<400> SEQUENCE: 125

Lys Asn Asp Leu Xaa Arg Ala Thr
 1               5

<210> SEQ ID NO 126
<211> LENGTH: 9
<212> TYPE: PRT
<213> ORGANISM: Artificial Sequence
<220> FEATURE:
<223> OTHER INFORMATION: Description of Artificial Sequence: synthetic,
      no natural origin
```

```
<400> SEQUENCE: 126

Gln Ile Val Ser Ala Trp Arg Glu Thr
  1               5

<210> SEQ ID NO 127
<211> LENGTH: 10
<212> TYPE: PRT
<213> ORGANISM: Artificial Sequence
<220> FEATURE:
<223> OTHER INFORMATION: Description of Artificial Sequence: synthetic,
      no natural origin
<220> FEATURE:
<221> NAME/KEY: misc_feature
<222> LOCATION: (4)..(4)
<223> OTHER INFORMATION: Xaa is Pro or Ala

<400> SEQUENCE: 127

Cys Ala Leu Xaa Arg His Ile Gly Arg Cys
1               5                   10

<210> SEQ ID NO 128
<211> LENGTH: 10
<212> TYPE: PRT
<213> ORGANISM: Artificial Sequence
<220> FEATURE:
<223> OTHER INFORMATION: Description of Artificial Sequence: synthetic,
      no natural origin
<220> FEATURE:
<221> NAME/KEY: misc_feature
<222> LOCATION: (4)..(4)
<223> OTHER INFORMATION: Xaa is Pro or Ala

<400> SEQUENCE: 128

Cys Gln Leu Xaa Arg Ala Thr Ser Ser Cys
1               5                   10

<210> SEQ ID NO 129
<211> LENGTH: 11
<212> TYPE: PRT
<213> ORGANISM: Artificial Sequence
<220> FEATURE:
<223> OTHER INFORMATION: Description of Artificial Sequence: synthetic,
      no natural origin

<400> SEQUENCE: 129

Cys Ile Thr Ser Gln Arg Glu Thr Gly Trp Cys
1               5                   10

<210> SEQ ID NO 130
<211> LENGTH: 9
<212> TYPE: PRT
<213> ORGANISM: Artificial Sequence
<220> FEATURE:
<223> OTHER INFORMATION: Description of Artificial Sequence: synthetic,
      no natural origin

<400> SEQUENCE: 130

Cys Arg Arg Ser Thr Thr Gly Ile Cys
1               5

<210> SEQ ID NO 131
<211> LENGTH: 10
<212> TYPE: PRT
<213> ORGANISM: Artificial Sequence
<220> FEATURE:
<223> OTHER INFORMATION: Description of Artificial Sequence: synthetic,
      no natural origin
<220> FEATURE:
```

```
<221> NAME/KEY: misc_feature
<222> LOCATION: (6)..(6)
<223> OTHER INFORMATION: Xaa is Tyr or Lys

<400> SEQUENCE: 131

Cys Ser Thr Thr Leu Xaa Arg Gly Thr Cys
 1               5                  10

<210> SEQ ID NO 132
<211> LENGTH: 8
<212> TYPE: PRT
<213> ORGANISM: Artificial Sequence
<220> FEATURE:
<223> OTHER INFORMATION: Description of Artificial Sequence: synthetic,
      no natural origin
<220> FEATURE:
<221> NAME/KEY: misc_feature
<222> LOCATION: (5)..(5)
<223> OTHER INFORMATION: Xaa is Pro or Ala

<400> SEQUENCE: 132

Arg Val Asp Leu Xaa Arg Glu Thr
 1               5

<210> SEQ ID NO 133
<211> LENGTH: 12
<212> TYPE: PRT
<213> ORGANISM: Artificial Sequence
<220> FEATURE:
<223> OTHER INFORMATION: Description of Artificial Sequence: synthetic,
      no natural origin

<400> SEQUENCE: 133

Lys His Ile Lys Asp Trp Glu His Leu Glu Glu Phe
 1               5                  10

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: synthetic,
      no natural origin

<400> SEQUENCE: 134

Lys Arg Lys Asp Gly Glu His Trp Leu
 1               5

<210> SEQ ID NO 135
<211> LENGTH: 9
<212> TYPE: PRT
<213> ORGANISM: Artificial Sequence
<220> FEATURE:
<223> OTHER INFORMATION: Description of Artificial Sequence: synthetic,
      no natural origin

<400> SEQUENCE: 135

Arg Gln Ala Lys Ser Trp Ser Ser Leu
 1               5

<210> SEQ ID NO 136
<211> LENGTH: 9
<212> TYPE: PRT
<213> ORGANISM: Artificial Sequence
<220> FEATURE:
<223> OTHER INFORMATION: Description of Artificial Sequence: synthetic,
      no natural origin

<400> SEQUENCE: 136
```

Tyr Gln Ala Lys Glu Trp Ser Asn Leu
1               5

<210> SEQ ID NO 137
<211> LENGTH: 9
<212> TYPE: PRT
<213> ORGANISM: Artificial Sequence
<220> FEATURE:
<223> OTHER INFORMATION: Description of Artificial Sequence: synthetic,
      no natural origin

<400> SEQUENCE: 137

Lys Asp Trp Glu His Arg Val Pro Ser
1               5

<210> SEQ ID NO 138
<211> LENGTH: 6
<212> TYPE: PRT
<213> ORGANISM: Artificial Sequence
<220> FEATURE:
<223> OTHER INFORMATION: Description of Artificial Sequence: synthetic,
      no natural origin

<400> SEQUENCE: 138

Lys Asp Trp Glu His Leu
1               5

<210> SEQ ID NO 139
<211> LENGTH: 6
<212> TYPE: PRT
<213> ORGANISM: Artificial Sequence
<220> FEATURE:
<223> OTHER INFORMATION: Description of Artificial Sequence: synthetic,
      no natural origin

<400> SEQUENCE: 139

Lys Asp Trp Ser His Leu
1               5

<210> SEQ ID NO 140
<211> LENGTH: 12
<212> TYPE: PRT
<213> ORGANISM: Artificial Sequence
<220> FEATURE:
<223> OTHER INFORMATION: Description of Artificial Sequence: synthetic,
      no natural origin

<400> SEQUENCE: 140

Pro Lys Ser Asp Pro Gln Met Gly Lys Arg Arg Arg
1               5                   10

<210> SEQ ID NO 141
<211> LENGTH: 9
<212> TYPE: PRT
<213> ORGANISM: Artificial Sequence
<220> FEATURE:
<223> OTHER INFORMATION: Description of Artificial Sequence: synthetic,
      no natural origin

<400> SEQUENCE: 141

His Pro Arg Pro Gln Leu Ala Ser Leu
1               5

<210> SEQ ID NO 142
<211> LENGTH: 9
<212> TYPE: PRT
<213> ORGANISM: Artificial Sequence

```
<220> FEATURE:
<223> OTHER INFORMATION: Description of Artificial Sequence: synthetic,
      no natural origin

<400> SEQUENCE: 142

His Pro Asp Pro Gln Ser Ser His Ser
  1               5

<210> SEQ ID NO 143
<211> LENGTH: 9
<212> TYPE: PRT
<213> ORGANISM: Artificial Sequence
<220> FEATURE:
<223> OTHER INFORMATION: Description of Artificial Sequence: synthetic,
      no natural origin

<400> SEQUENCE: 143

Arg Phe Thr Asp Pro Gln Leu His Pro
  1               5

<210> SEQ ID NO 144
<211> LENGTH: 9
<212> TYPE: PRT
<213> ORGANISM: Artificial Sequence
<220> FEATURE:
<223> OTHER INFORMATION: Description of Artificial Sequence: synthetic,
      no natural origin

<400> SEQUENCE: 144

Lys Gln Asp Pro Gln Gln Gln Lys Gln
  1               5

<210> SEQ ID NO 145
<211> LENGTH: 9
<212> TYPE: PRT
<213> ORGANISM: Artificial Sequence
<220> FEATURE:
<223> OTHER INFORMATION: Description of Artificial Sequence: synthetic,
      no natural origin

<400> SEQUENCE: 145

Val Pro Asp Ser Gln Leu Glu Trp Pro
  1               5

<210> SEQ ID NO 146
<211> LENGTH: 9
<212> TYPE: PRT
<213> ORGANISM: Artificial Sequence
<220> FEATURE:
<223> OTHER INFORMATION: Description of Artificial Sequence: synthetic,
      no natural origin

<400> SEQUENCE: 146

His Cys Asp Pro Gln Leu Tyr Gln Glu
  1               5

<210> SEQ ID NO 147
<211> LENGTH: 9
<212> TYPE: PRT
<213> ORGANISM: Artificial Sequence
<220> FEATURE:
<223> OTHER INFORMATION: Description of Artificial Sequence: synthetic,
      no natural origin

<400> SEQUENCE: 147

Asp Pro Gln Met Phe Arg Arg His Cys
  1               5
```

```
<210> SEQ ID NO 148
<211> LENGTH: 9
<212> TYPE: PRT
<213> ORGANISM: Artificial Sequence
<220> FEATURE:
<223> OTHER INFORMATION: Description of Artificial Sequence: synthetic,
      no natural origin

<400> SEQUENCE: 148

Phe Lys Asp Gly Gln Leu Arg Pro Gln
 1               5

<210> SEQ ID NO 149
<211> LENGTH: 11
<212> TYPE: PRT
<213> ORGANISM: Artificial Sequence
<220> FEATURE:
<223> OTHER INFORMATION: Description of Artificial Sequence: synthetic,
      no natural origin

<400> SEQUENCE: 149

Cys Pro Asp Pro Gln Leu Arg Leu His Arg Cys
 1               5                  10

<210> SEQ ID NO 150
<211> LENGTH: 11
<212> TYPE: PRT
<213> ORGANISM: Artificial Sequence
<220> FEATURE:
<223> OTHER INFORMATION: Description of Artificial Sequence: synthetic,
      no natural origin

<400> SEQUENCE: 150

Cys Pro Asp Pro Gln Leu Asn Gly Thr Arg Cys
 1               5                  10

<210> SEQ ID NO 151
<211> LENGTH: 11
<212> TYPE: PRT
<213> ORGANISM: Artificial Sequence
<220> FEATURE:
<223> OTHER INFORMATION: Description of Artificial Sequence: synthetic,
      no natural origin

<400> SEQUENCE: 151

Cys Pro Asp Pro Gln Leu Ser Ser Leu Arg Cys
 1               5                  10

<210> SEQ ID NO 152
<211> LENGTH: 11
<212> TYPE: PRT
<213> ORGANISM: Artificial Sequence
<220> FEATURE:
<223> OTHER INFORMATION: Description of Artificial Sequence: synthetic,
      no natural origin

<400> SEQUENCE: 152

Cys Pro Asp Pro Gln Leu Arg Leu His Arg Cys
 1               5                  10

<210> SEQ ID NO 153
<211> LENGTH: 11
<212> TYPE: PRT
<213> ORGANISM: Artificial Sequence
<220> FEATURE:
<223> OTHER INFORMATION: Description of Artificial Sequence: synthetic,
      no natural origin
```

```
<400> SEQUENCE: 153

Cys Pro Asp Pro Gln Leu Thr Leu His Arg Cys
  1               5                  10

<210> SEQ ID NO 154
<211> LENGTH: 11
<212> TYPE: PRT
<213> ORGANISM: Artificial Sequence
<220> FEATURE:
<223> OTHER INFORMATION: Description of Artificial Sequence: synthetic,
      no natural origin

<400> SEQUENCE: 154

Cys Pro Asp Pro Gln Leu Ser Leu Gln Arg Cys
  1               5                  10

<210> SEQ ID NO 155
<211> LENGTH: 11
<212> TYPE: PRT
<213> ORGANISM: Artificial Sequence
<220> FEATURE:
<223> OTHER INFORMATION: Description of Artificial Sequence: synthetic,
      no
      natural origin

<400> SEQUENCE: 155

Cys Pro Asp Ala Gln Leu Ser Gly Thr Arg Cys
  1               5                  10

<210> SEQ ID NO 156
<211> LENGTH: 10
<212> TYPE: PRT
<213> ORGANISM: Artificial Sequence
<220> FEATURE:
<223> OTHER INFORMATION: Description of Artificial Sequence: synthetic,
      no natural origin

<400> SEQUENCE: 156

His Pro Asp Pro Gln Leu Ser Leu His Arg
  1               5                  10

<210> SEQ ID NO 157
<211> LENGTH: 42
<212> TYPE: DNA
<213> ORGANISM: Artificial Sequence
<220> FEATURE:
<223> OTHER INFORMATION: Description of Artificial Sequence: synthetic,
      no natural origin

<400> SEQUENCE: 157
gcggaattcg acgtcgccat gggctgggaa caactggagc ag                         42

<210> SEQ ID NO 158
<211> LENGTH: 37
<212> TYPE: DNA
<213> ORGANISM: Artificial Sequence
<220> FEATURE:
<223> OTHER INFORMATION: Description of Artificial Sequence: synthetic,
      no natural origin

<400> SEQUENCE: 158
gcgaagcttg tcgaccggcg gtttgccggg ctggctg                               37

<210> SEQ ID NO 159
<211> LENGTH: 45
<212> TYPE: DNA
<213> ORGANISM: Artificial Sequence
```

```
<220> FEATURE:
<223> OTHER INFORMATION: Description of Artificial Sequence: synthetic,
      no natural origin

<400> SEQUENCE: 159
gcggaattcg acgtcgccat ggccttcctc ggcgacggcg gcgac                        45

<210> SEQ ID NO 160
<211> LENGTH: 37
<212> TYPE: DNA
<213> ORGANISM: Artificial Sequence
<220> FEATURE:
<223> OTHER INFORMATION: Description of Artificial Sequence: synthetic,
      no natural origin

<400> SEQUENCE: 160
gcgaagcttg tcgaccggcg gtttgccggg ctggctg                                 37

<210> SEQ ID NO 161
<211> LENGTH: 1136
<212> TYPE: DNA
<213> ORGANISM: Artificial Sequence
<220> FEATURE:
<223> OTHER INFORMATION: Description of Artificial Sequence: synthetic,
      no natural origin

<400> SEQUENCE: 161
gaattcacac acaatcagat ttatagagag atttataaaa aaaaaaaaac atatggactt        60
tcaagtgcag attttcagct tcctcctcat cagcgcctca gttatcatct ctagggatc       120 catgggctgg gaacaactgg agcagtgcgg ctatccggtg cagcggctgg tcgccctcta      180
cctggcggcg cggctgtcgt ggaaccaggt cgaccaggtg atccgcaacg ccctggccag      240
ccccggcagc ggcggcgacc tgggcgaagc gatccgcgag cagccggagc aggcccgtct      300
ggccctgacc ctggccgccg ccgagagcga gcgcttcgtc cggcagggca ccggcaacga      360
cgaggccggc gcggccaacg gcccggcgga cagcggcgac gccctgctgg agcgcaacta      420
tcccactggc gcggagttcc tcggcgacgg cggcgacgtc agcttcagca cccgcggcac      480
gcagaactgg acggtggagc ggctgctcca ggcgcaccgc caactggagg agcgcggcta      540
tgtgttcgtc ggctaccacg gcaccttcct cgaagcggcg caaagcatcg tcttcggcgg      600
ggtgcgcgcg cgcagccagg acctcgacgc gatctggcgc ggtttctata tcgccggcga      660
tccggcgctg gcctacggct acgcccagga ccaggaaccc gacgcacgcg gccggatccg      720
caacggtgcc ctgctgcggg tctatgtgcc gcgctcgagc ctgccgggct tctaccgcac      780
cagcctgacc ctggccgcgc cggaggcggc gggcgaggtc gaacggctga tcggccatcc      840
gctgccgctg cgcctggacg ccatcaccgg ccccgaggag gaaggcgggc gcctggagac      900
cattctcggc tggccgctgg ccgagcgcac cgtggtgatt ccctcggcga tccccaccga      960
cccgcgcaac gtcggcggcg acctcgaccc gtccagcatc cccgacaagg aacaggcgat     1020
cagcgccctg ccggactacg ccagccagcc cggcaaaccg ccggtcgacg gaggtggagg     1080
ttctaacctc atcgttgaac ttatccgcgg taccggttct aaactcgag tctaga          1136

<210> SEQ ID NO 162
<211> LENGTH: 827
<212> TYPE: DNA
<213> ORGANISM: Artificial Sequence
<220> FEATURE:
<223> OTHER INFORMATION: Description of Artificial Sequence: synthetic,
      no natural origin
```

<400> SEQUENCE: 162

```
gaattcacac acaatcagat ttatagagag atttataaaa aaaaaaaaac atatggactt      60
tcaagtgcag attttcagct tcctcctcat cagcgcctca gttatcatct ctagggatc     120
catggccttc ctcggcgacg gcggcgacgt cagcttcagc acccgcggca cgcagaactg     180
gacggtggag cggctgctcc aggcgcaccg ccaactggag gagcgcggct atgtgttcgt     240
cggctaccac ggcaccttcc tcgaagcggg gcaaagcatc gtcttcggcg gggtgcgcgc     300
gcgcagccag gacctcgacg cgatctggcg cggtttctat atcgccggcg atccggcgct     360
ggcctacggc tacgcccagg accaggaacc cgacgcacgc ggccggatcc gcaacggtgc     420
cctgctgcgg gtctatgtgc cgcgctcgag cctgccgggc ttctaccgca ccagcctgac     480
cctggccgcg ccggaggcgg cgggcgaggt cgaacggctg atcggccatc cgctgccgct     540
gcgcctggac gccatcaccg gccccgagga ggaaggcggg cgcctggaga ccattctcgg     600
ctggccgctg gccgagcgca ccgtggtgat tccctcggcg atccccaccg acccgcgcaa     660
cgtcggcggc gacctcgacc cgtccagcat ccccgacaag gaacaggcga tcagcgccct     720
gccggactac gccagccagc ccggcaaacc gccggtcgac ggaggtggag gttctaacct     780
catcgttgaa cttatccgcg gtaccggttc ttaaactcga gtctaga                   827
```

<210> SEQ ID NO 163
<211> LENGTH: 1046
<212> TYPE: DNA
<213> ORGANISM: Artificial Sequence
<220> FEATURE:
<223> OTHER INFORMATION: Description of Artificial Sequence: synthetic, no natural origin

<400> SEQUENCE: 163

```
gaattcacac acaatcagat ttatagagag atttataaaa aaaaaaaaac atatggattt      60
tcaagtgcag attttcagct tcctgctaat cagtgcctca gtcataatat ctagaggaca     120
aattgttctc acccagtctc cagcaatcat gtctgcatct ccaggggaga aggtcaccat     180
gacctgcagt gccagttcaa gtgtaagtaa aatgcaatgg tatcagcaga agtcaggcac     240
ctcccccaaa agatggattt atgacacatc caaactggcc tctggagtcc ctggtcgctt     300
cagtggcagt gggtctggga cctcttactc tctcacaatc agcagcatgg aggctgaaga     360
tgctgccact tattactgcc agcagtggag tagtaacccg ctcacgttcg gtgctgggac     420
caagctggag ataaaaggct ctactagtgg ttccggaaag agctctgaag gtaaaggtga     480
ggtccagctg cagcagtctg gacctgagct ggtaaatcct ggggcttcag tgaagatgtc     540
ctgcaaggcc tctggataca cattcattac ctatgttatg cactgggtga agcagaagcc     600
tgggcagggc cttgagtgga ttggatatat taatcctaac aaagacggta caaagttcaa     660
tgagaagttc aaaggcaagg ccacactgac ttcagacaaa tcctccaaca cagcctacat     720
ggagctcagc agcctgacct ctgaggactc tgcggtctat tactgtgcaa gagactatga     780
ttacgactgg tttgcttact ggggccaggg gactctggtc actgtctctg cagtcgacga     840
acaaaaactc atctcagaag aggatctgaa tgctgtgggc caggacacgc aggaggtcat     900
cgtggtgcca cactccttgc cctttaaggt ggtggtgatc tcagccatcc tggccctggt     960
ggtgctcacc atcatctccc ttatcatcct catcatgctt ggcagaaga agccacgtta    1020
ggcggccgct cgagcatgca tctaga                                        1046
```

<210> SEQ ID NO 164

-continued

```
<211> LENGTH: 12
<212> TYPE: RNA
<213> ORGANISM: Artificial Sequence
<220> FEATURE:
<223> OTHER INFORMATION: Ribosome-inactivation is achieved in all cases
      through the cleavage of an N-glycosidic bond between ribose and
      the adenine at position 7 of this sequence which is located
      250-400nt from e 3' end of 23S/25S/28S rRNA

<400> SEQUENCE: 164
aguacgagag ga                                                          12

<210> SEQ ID NO 165
<211> LENGTH: 5
<212> TYPE: PRT
<213> ORGANISM: Artificial Sequence
<220> FEATURE:
<223> OTHER INFORMATION: Flexible linker

<400> SEQUENCE: 165

Gly Gly Gly Gly Ser
1               5

<210> SEQ ID NO 166
<211> LENGTH: 6
<212> TYPE: PRT
<213> ORGANISM: Artificial Sequence
<220> FEATURE:
<223> OTHER INFORMATION: Motif which functions to retain certain
      proteins in the ER

<400> SEQUENCE: 166

Leu Tyr Ser Leu Tyr Ser
1               5

<210> SEQ ID NO 167
<211> LENGTH: 4
<212> TYPE: PRT
<213> ORGANISM: Artificial Sequence
<220> FEATURE:
<223> OTHER INFORMATION: C-terminal recognition sequence which functions
      to retain certain proteins in the ER

<400> SEQUENCE: 167

Lys Asp Glu Leu
1

<210> SEQ ID NO 168
<211> LENGTH: 10
<212> TYPE: PRT
<213> ORGANISM: Artificial Sequence
<220> FEATURE:
<223> OTHER INFORMATION: Linker sequence

<400> SEQUENCE: 168

Gly Gly Gly Gly Ser Gly Gly Gly Gly Ser
1               5                   10
```

MOLECULAR PATHOGENICIDE MEDIATED PLANT DISEASE RESISTANCE

FIELD OF THE INVENTION

The present invention relates to gene constructs suitable for expressing agents to protect a plant against pathogens and the suitable proteins for such plant protection. These agents are named "molecular pathogenicides". This invention is related to the genetic engineering of plants and to means and methods for conferring pathogen resistance on a plant using a gene or genes encoding: a pathogen specific antibody and a pathogen specific antibody including a toxic activity which blocks stages of the pathogen life cycle, pathogen replication or pathogen movement within a plant or pathogen transmission from plant to plant. The means and methods are given for soluble expression of recombinant antibodies, antibody fusion proteins and antibody protein complexes in different plant cell compartments or the immobilisation of recombinant antibodies, antibody fusion proteins and antibody protein complexes in cellular membranes in different orientations and the display of recombinant proteins on the plant cell membrane. This invention also describes novel methods and protein binding partners for assembling protein complexes from individual polypeptide chains during expression of these proteins in vivo. Also given are the methods for activation of the molecular pathogenicides by in vivo proteolytic cleavage.

Several documents are cited throughout the text of this specification. Each of the documents cited herein (including any manufacturers specifications, instructions, etc.) are hereby incorporated by reference; however, there is no admission that any document cited is indeed prior art of the present invention.

BACKGROUND OF THE INVENTION

Plant disease constitutes a major and ongoing threat to human food stocks and animal feed. Most crop plants are regularly exposed to one or more pathogen(s) that can cause incredible damage resulting in substantial economical losses every year. Attack by pathogens, such as viruses, bacteria, fungi, nematodes and insects and is a severe economic problem, which impacts all economically important crops, for example rice, soybean, sweet potato, wheat, potato, grape, maize and ornamental plants. Current protective measures rely heavily on chemical control measures for pathogen vectors, which have undesirable environmental consequences.

A more effective approach to protecting plants from pathogen attack is to create plants that are endogenously resistant to pathogens. However, plant breeders have limited sources of resistance genes against plant diseases. This can now be achieved using genetic engineering techniques, by providing the plant with genetic information required for affecting the pathogens and for being resistant to the disease caused by the pathogen. For example, in the case of a viral pathogen, the host plant is resistant if it has the ability to inhibit or retard the replication of a virus, the symptoms of viral infection or the life cycle of the virus, including its transmission. "Resistant" is the opposite of "susceptible" and may be divided into three levels:

1) Full,
2) Medium,
3) Partial resistance,

A plant may be considered fully resistant when it shows no symptoms on infection and there is no evidence of pathogen replication or reproduction. The host plant may be resistant to the establishment of infection, pathogen reproduction and/or pathogen movement and transmission.

In recent years, the advances in plant molecular virology have enhanced the understanding of pathogen genome organisation and gene function. Moreover, genetic engineering of plants for virus resistance has recently provided new strategies for control of viral disease (Baulcombe, 1994), (Gadani et al., 1990), (Wilson, 1993). The following genes were expressed in transgenic plants in order to confer resistance: viral coat proteins, non-structural proteins of viral genomes, viral anti-sense transcripts, viral satellite RNAs, ribozymes and interferon genes (Baulcombe, 1994), (Gadani et al., 1990), (Wilson, 1993), (Harrison et al., 1987), (Namba et al., 1991), (Anderson et al., 1992). Although most of these approaches have been effective for attenuating infections, resistance was not complete and confined to a small spectrum of viral pathogens (Falk and Bruening, 1994), (Wilson, 1993) and bears significant risks (Palukaitis and Roossinck, 1996).

The major disadvantages of these methods are:

1) Host range is limited.
2) Pathogen range is limited.
3) Resistance is partial and though symptoms are delayed infection still results in the disease.
4) Resistance could be broken in case of coat protein mediated resistance and ribozyme mediated resistance.
5) Expression of viral proteins can lead to enhanced pathogen activity. For example, in the case of viral coat protein mediated resistance, cross encapsidation of mild non-pathogenic strains of virus by the expressed coat protein can occur which then leads to development of a more severe disease.

An alternative way to protect plants against pathogen infection is the generation and expression of recombinant antibodies (rAbs), which are often referred to as "Plantibodies". Pathogen-specific recombinant antibodies targeted to different compartments of plant cells or different plant organs overcome many of the problems mentioned before and confer a broader spectrum of resistance to disease (Baulcombe, 1994). To achieve this, recombinant antibodies (Plückthun, 1991), (Winter and Milstein, 1991) against the target proteins have to be generated by cloning the corresponding antibody heavy and light chain genes from hybridoma cells, synthetic, semi-synthetic and immunocompetent phage display or ribosome display libraries; or by the generation of fully synthetic designer antibodies. This is followed by subsequent modification and rAb expression in different compartments of heterologous hosts such as bacteria, yeast, algae, baculovirus infected insect cells, mammalian cells and plants. For example, antibodies and antibody-fusion proteins binding to conserved functional domains of viral coat proteins, movement proteins, replicases or transmission factors can be used to inactivate such targets inside or outside the plant cell through immunomodulation. The feasibility of expressing recombinant antibodies (Plückthun, 1991), (Winter and Milstein, 1991) for the generation of resistance has been shown recently for both animal (Chen et al., 1994), (Duan et al., 1994), (Marasco et al., 1993) and plant viruses (Tavladoraki et al., 1993), (Voss et al., 1995), (Zimmermann et al., 1998). Single chain antibody fragments derived from monoclonal antibodies (scFvs) (Bird et al., 1988) directed against Rev (Duan et al., 1994) and gp120 (Chen et al., 1994) (Marasco et al., 1993) of HIV, inhibited HIV-replication, virion assembly and syncytia formation when expressed intracellularly, or within the ER of human cells.

Interestingly, intracellular expression of an scFv specific for the artichoke mottled crinkle virus coat protein in transgenic Tobacco caused a reduction of infection and a delay in symptom development (Tavladoraki et al., 1993). Targeting of TMV-specific full-size antibodies to the intercellular space of Tobacco plants inhibited viral infections up to 70% (Voss et al., 1995). In the latter case, plant produced antibodies showed the same specificity and affinity for TMV (Fischer et al., 1998) as the parental murine antibody. Cytosolic expression of an engineered scFv derived from this anti-TMV antibody yielded fully resistant Tobacco plants, even under systemic infection conditions (Zimmermann et al., 1998). These studies demonstrate the potential of heterologously expressed recombinant antibodies to combat pathogens via intra- or extra-cellular modulation of pathogen proteins.

Plant cells can synthesise large amounts of antibodies that are functionally indistinguishable from the source monoclonal. For example, full-size antibodies (During et al., 1990), (Hiatt et al., 1989), (Voss et al., 1995), Fab-fragments (De Neve et al., 1993), scFvs (Owen et al., 1992; Zimmermann et al., 1998), (Tavladoraki et al., 1993), scFv fusion proteins (Spiegel et al., Plant Science 149 (1999), 63–71), bispecific scFv (Fischer et al., 1999) and dAbs (Benvenuto et al., 1991) have been successfully expressed in Tobacco, Potato (Schouten et al., 1997) or Arabidopsis, reaching expression levels as high as 6.8% of the total protein (Fiedler et al., 1997). Targeting of recombinant antibodies by exploiting known protein trafficking signal sequences now permits rAb expression in the cytoplasm (scFv fragments (Tavladoraki et al., 1993; Zimmermann et al., 1998)), the endoplasmic reticulum (Fiedler et al., 1997), chloroplasts (During et al., 1990) and the intercellular space (Benvenuto et al., 1991; De Neve et al., 1993; Voss et al., 1995; Zimmermann et al., 1998) (full-size, Fab fragments, scFvs and single domain Abs). These results demonstrate the flexibility of the plant system to express any recombinant antibody or recombinant antibody fragments in almost all plant compartments, using targeting sequences that also may be from plants or derived from other eukaryotes.

The advantage of targeted protein expression is that the rAbs can be expressed where the pathogen is most vulnerable and where they will have the maximal protective effect. In patent application WO 96/09398 the use of antibody-fusion proteins as agents for controlling crop disease caused by pathogens is proposed.

The antibody delivers a toxin which kills the pathogen in transgenic plants or when expressed or applied as an external immunotoxin. WO 96/09398 is focussed on recombinant Ab-fusion proteins—single polypeptides that are either genetically, chemically or "biochemically" linked to form an immunotoxin. However, WO 96/09398 does not provide proof of principle for antibody mediated pathogen resistance and it was doubtful whether any of the hypothetical examples in WO 96/09398 would work to the extent that a protection of plants against pathogen attack can be obtained sufficient to comply with the needs of the breeders and farmers. Thus, there is still a need of means and methods for conferring antipathogenic/predator characteristics to transgenic plants.

SUMMARY OF THE INVENTION

The objective of this current patent application is to provide means and methods for protecting plants, in particular monocotyledonous and dicotyledonous agricultural crops and ornamental plants, against pathogens in a more effective and environmentally sensitive manner.

Accordingly, the solution to the technical problem is achieved by providing the embodiments characterised in the claims.

As will be described hereinbelow, the above-mentioned objective is met according to the invention by any one of the following or any combination of the following inventions: i) the expression of pathogen specific recombinant antibodies and parts thereof, or ii) by fusing antibodies or parts thereof to toxins, proteins, or enzymes having activity against the pathogens or to the effective parts of these toxins or enzymes, and then expressing these fusion proteins, or iii) by assembling protein complexes composed of an antibody or fragment thereof in vivo using the novel binding proteins described here and or iv) including a specific protease sensitive sequence, that is cleaved (e.g. in the presence of the pathogen or in a specific plant cell compartment) to release and or activate the toxic activity of any of the recombinant proteins in i) to iii), and or v) targeting or integrating any of the recombinant proteins in i) to iv) to cell membranes in any orientation. These agents are also named "molecular pathogenicides". Thus, in one aspect the present invention relates to a fusion protein comprising (a) at least one binding domain specifically recognising an epitope of a plant pathogen; and
(b) at least one further domain comprising a protein or peptide sequence which is toxic to the pathogen or detrimental to its replication, transmission or life cycle.

Said domains can be linked by covalent or non-covalent bonds. In a preferred embodiment of the fusion protein of the invention said binding domain comprises an antibody, a T-cell receptor, a pathogen specific receptor, a peptide specific for an epitope of a pathogen, or at least the binding site of any one of those. In another aspect, the invention relates to membrane associated binding domains and further domains, respectively, as defined herein.

The fusion proteins composed of a pathogen specific antibody and toxin molecule can be made by fusing the respective parts by genetic or biochemical means. In addition, the chimeric protein can preferably be assembled in vivo from its parts by the plant or via expression in the organisms' endogenous protein machinery. In a particularly preferred and advantageous embodiment of the invention, these domains or parts thereof, fusion proteins or protein complexes can also be targeted to organelles and plant cell compartments or immobilised and membrane anchored by the addition of signal sequences and or membrane anchors. The recombinant molecular pathogenicide protein preferably contains specific protease cleavage sequences that are cleaved in vivo, by a plant and/or a pathogen specific protease(s), to release and or activate the toxic agent(s), or parts thereof, upon infection.

The fusion protein of the present invention can further comprise a carrier protein suitable for delivering the fusion protein or its domains into a host cell, preferably plant cell or a cellular compartment thereof. Furthermore, the fusion protein of the present invention can comprise a fluorophore such as green fluorescent protein fused to at least one of the above-described domains the fusion protein consists of. In a further aspect, the present invention relates to a pathogenicide comprising at least one binding and/or further domain as defined herein and a cellular targeting sequence and/or membrane localisation sequence and/or motif that leads to membrane anchoring. Preferably, the membrane localisation sequence is proteolytically sensitive.

Suitable membrane anchor sequences, enabling the integration of secretory recombinant antibody fusion proteins and parts thereof in the plasma membrane, include the human T cell receptor transmembrane domains (Gross and Eshhar, 1992), glyco-phosphatidyl inositol (GPI) anchors (Gerber et al., 1992), immunoglobulin superfamily membrane anchors, tetraspan family members (Tedder and Engel, 1994; Wright and Tomlinson, 1994) and any transmembrane sequence(s) from a known protein or synthesised sequences that have a similar function and can be included in the target protein by recombinant DNA technology. Fusion of a protein to these sequences would permit display of the recombinant protein on the lumenal face of organelles of the secretory or endocytic pathway or the plant cell membrane. This has the advantage that the recombinant protein can be targeted to the intracellular space where many pathogens are most vulnerable.

In addition, the antibodies or parts thereof, or the recombinant antibody fusion proteins, or parts thereof, may be targeted to cell membranes where they could face the cytosolic side of the membrane. Suitable targeting sequences for cytoplasmic display, include the transmembrane domains of: KAR1, for nuclear membrane integration (Rose and Fink, 1987), middle-T antigen (Kim et al., 1997), for plasma membrane integration and cytochrome b5, for ER membrane integration (Kim et al., 1997). C-terminal linkages to fatty acids using consensus amino acid sequences leading to post translational prenylation, farnesylation, palmitoylation, myristoylation or ankyrin sequence motifs can also be used. This cytoplasmic display method has the significant advantage that the recombinant proteins can be localised at the site of intracellular pathogen replication, where they will have the most potent effect. In addition, membrane localisation of proteins stabilises the protein and reduces the effect of C-terminal protein degradation in vivo. Preferably, the pathogenicide of the invention comprises the fusion protein described herein.

In a particularly preferred embodiment, the present invention relates to the described pathogenicides wherein said binding domain(s) and/or said further domain(s) are capable of self assembly in vivo.

In a further embodiment, the present invention relates to a polynucleotide encoding a fusion protein or pathogenicide of the invention. Thus, the invention relates to one or more gene constructs that encode a nucleotide sequence encoding an antibody or part thereof which is specific for a pathogen and in the case of fusion proteins, for a nucleotide sequence encoding a protein, enzyme or peptide which has detrimental effects on a pathogen and ideally is toxic to the pathogen. This invention includes antibodies specific for the pathogen and/or for host proteins utilised by the pathogen during its life cycle. This invention also relates to chimeric proteins that consist of an antibody, antibodies or parts thereof, which are specific for a pathogen, and a protein or peptide which has detrimental or ideally toxic effects on the pathogen and which has been constructed by biochemically linking the antibody or parts thereof to the toxin. Furthermore, the present invention relates to a vector comprising the polynucleotide of the invention. Said vector can comprise separate polynucleotides encoding at least one of said binding domain(s) and/or said further domain(s) of the above-described fusion protein. In addition, the present invention relates to a composition comprising vectors wherein each vector contains at least one polynucleotide encoding at least one binding domain and/or at least one further domain of the fusion protein or the pathogenicide of the invention; and wherein the expression of at least two of said polynucleotides results in the production of said fusion protein or said pathogenicide or assembly of the same in vivo.

In a preferred embodiment of the vector or the composition of the invention the polynucleotide is operatively linked to regulatory sequences allowing the expression of the fusion protein, pathogenicide or the domains thereof in a host cell. Said regulatory sequence can be a constitutive, chimeric, tissue specific or inducible promoter.

Furthermore, the present invention relates to a host cell comprising any one of the above-described polynucleotides, vectors or vectors of the compositions.

In another embodiment the present invention relates to a method for the production of a molecular pathogenicide comprising:
(a) culturing the host cell of the invention under conditions suitable for the expression of the polynucleotide; and
(b) recovering the fusion protein, pathogenicide or the domains thereof from the culture.

The present invention also relates to a molecular pathogenicide obtainable by the method of the invention or encodable by the polynucleotide of the invention.

This invention also relates to in vivo assembled protein complexes composed of one or more discrete polypeptide chains, encoded by separate nucleotide sequences on one or more constructs, that are assembled by the plant or expression organisms protein synthesis machinery into a protein complex.

Furthermore, the present invention relates to a method for the production of pathogen resistant transgenic plants, plant cells or plant tissue comprising the introduction of a polynucleotide or vector of the invention or the vectors of the composition of the invention into the genome of a plant, plant cell or plant tissue.

The present invention also relates to a transgenic plant cell which contains stably integrated into the genome a polynucleotide or vector of the invention or the vectors of the composition of the invention or obtainable according to the method of the invention.

In addition, the present invention relates to a transgenic plant or plant tissue comprising the above-described plant cells or obtainable by the method of the invention. Encompassed are also the transgenic plants wherein the fusion protein or pathogenicide are made functional against pathogens by in vivo assembly after co-transformation of at least two independent plant expression constructs or after sexual crossing to form hybrid offspring from two parental plants expressing one or more of the domains of the fusion protein or the pathogenicide, or any other form of genetic recombination. Preferably, the transgenic plant of the invention displays improved resistance against a pathogen that the wild type plant was susceptible to.

Furthermore, the present invention relates to harvestable parts and propagation material of a plant of the invention comprising plant cells of the invention.

In a still further embodiment, the present invention relates to a kit comprising any one of the described fusion proteins, pathogenicides, polynucleotides, compositions or molecular pathogenicides of the invention.

In another embodiment the present invention relates to the use of the described antibodies, fusion proteins, polynucleotides, vectors, compositions and molecular pathogenicides of the invention in agriculture for the protection of a plant against the action of a pathogen.

Some aspects of the present invention will be described herein below in more detail.

The term "binding domain" is used to denote polypeptide chain(s) which exhibit a strong monovalent, bivalent or polyvalent binding to a given epitope or epitopes. Preferably, said binding domain is an antibody or a binding site thereof. The antibodies may be generated by hybridoma technology, or ribosome display, or phage display, of natural naïve origin, or immunised origin, semi-synthetic or fully synthetic libraries. The term "antibody" is also used to denote designer antibodies. These antibody, polypeptides are encoded by an immunoglobulin gene or immunoglobulin genes, or fragments thereof which specifically bind the given epitope or epitopes. The recognised immunoglobulin genes include the kappa and lambda light chain genes, the mu, delta, gamma, alpha and epsilon constant regions as well as all immunoglobulin variable regions from vertebrate, camelid, avian and pisces species. The term antibody, as used herein, includes in particular those antibodies synthesised or constructed de novo using recombinant DNA methodology, such as recombinant full-size antibodies, dimeric secretory IgA antibodies, multimeric IgM antibodies, F(ab')$_2$-fragments, Fab-fragments, Fv-fragments, single chain Fv-fragments (scFvs), bispecific scFvs, diabodies, single domain antibodies (dAb), minibodies and molecular recognition units (MRUs). Antibody sequences may be derived from any vertebrate, camelid, avian or pisces species using recombinant DNA technology, or also by using synthetic, semi-synthetic and naive or immunocompetent phage and ribosome display libraries, gene shuffling libraries, and fully synthetic designer antibodies. In this invention, the antibodies are generated against specific pathogen or host plant epitopes that are involved in the pathogen replication, reproduction or life cycle.

The term "pathogen" is used to denote viral or virus like organisms, bacteria, mycoplasmas, fungi, insects or nematodes that affect the germination of seed, growth, development, reproduction, harvest, yield or utility of a plant. The term "toxic" refers to an activity, which may be peptide or polypeptide encoded, that affects the reproduction or replication of a pathogen and/or any stages of its life cycle. In the case of viral pathogens, this includes entry into the plant, viral uncoating and disassembly, viral replication, viral assembly, cell to cell and long distance movement and the development, spread, or life cycle of the virus. Suitable toxic activities include RNAse (Leland et al., 1998) and DNAse, ribosome inactivating proteins (Barbieri et al., 1993), (Girbes et al., 1996), (Hartley et al., 1996) and or toxins with antimicrobial activity (Dempsey et al., 1998). Antibodies or recombinant proteins in themselves are also considered toxic when they affect the pathogen by binding to pathogen and or host proteins that are utilised by a pathogen during its replication, reproduction, life cycle or transmission. For example, a fusion protein composed of a virus specific antibody and a viral coat protein will interfere with virus reproduction by both binding to the virus and by disrupting viral assembly or disassembly in the host cell.

The term "molecular pathogenicide" refers to the antibodies and proteins described in this application, which have toxic effects on pathogen(s) either as single fusion proteins, when expressed in combination with other proteins, or when expressed as part of protein complexes that are assembled in vivo.

Monoclonal antibodies (Köhler and Milstein, 1975) can be raised against almost any epitope or molecular structure of a pathogen or host protein using several techniques. The most common method is the hybridoma technique starting with immunocompetent B lymphocytes from the spleen or thymus which are obtained after immunisation with native antigen, recombinant antigen, antigen fusion proteins, antigen domains or by in vitro or genetic immunisation. In addition, recent advances in molecular biology techniques now permit the use of cloned recombinant antibody fragments and antibodies derived from mice and other organisms than the mouse. Suitable recombinant antibody fragment(s) include the complete recombinant full-size antibodies, dimeric secretory IgA antibodies, multimeric IgM antibodies, the F(ab')$_2$ fragment, the Fab-fragment, the Fv-fragment, single chain antibody fragments (scFvs), single binding domains (dAbs), a bivalent scFv (diabody) (Poljak, 1994), minibody (Carter and Merchant, 1997), bispecific scFv antibodies (Plückthun and Pack, 1997) where the antibody molecule recognises two different epitopes, (which may be from the pathogen or the host or both the pathogen and the host), triabodies and any other part of the antibody such as, molecular recognition units (MRUs), which show binding to the target epitopes. Genes encoding these suitable recombinant antibody fragment(s) may be derived from vertebrates, camelids, avian or pisces species.

Also, single chain antibodies that have affinities for pathogen or host structures and proteins can be identified using phage display libraries or ribosome display libraries, gene shuffled libraries, which can be constructed from synthetic, semi-synthetic or naïve and immunocompetent sources (Plückthun, 1991; Winter et al., 1994; Winter and Milstein, 1991). Phage display and suitable techniques can be used to specifically identify antibodies, or fragments thereof, with the desired binding properties. Using recombinant antibody technology it is possible to identify antibodies or fragments that are highly specific for a single pathogen, or which recognise a consensus epitope conserved between several pathogens, where the antibodies will have a broad specificity against pathogens. The durability and effect of antibody mediated resistance can be improved by i) recombinant antibody affinity maturation, ii) CDR randomisation and selection, iii) stabilisation by framework optimisation of a selected pathogen specific antibody, iv) bi-specific antibody expression, v) the generation of antibody fusion proteins, or vi) the expression of antibodies in combinations with others that may potentiate their individual effects. For example, surface plasmon resonance as employed in the BIAcore system can be used to increase the efficiency of phage displayed antibodies selections, yielding a high increment of affinity from a single library of phage antibodies which bind to an epitope of a pathogen (Schier, Human Antibodies Hybridomas 7 (1996), 97–105; Malmborg, J. Immunol. Methods 183 (1995), 7–13). The recombinant antibodies can be identified and utilised according to methods that are familiar to anyone of ordinary skill in the art.

Antibodies

This invention describes antibodies or fragments thereof which recognise structures of the pathogen or host plant and directly or indirectly lead to resistance or partial resistance when expressed alone or when expressed as chimeric fusion protein coupled to a toxic activity or when expressed and assembled in viva with a toxic activity to form an in vivo assembled molecular pathogenicide protein complex. Antibodies can be generated that recognise pathogen-specific epitopes or host plant-specific epitopes which have a role in the life cycle of a pathogen. Suitable antibodies for engineering viral resistance include, but are not limited to, those binding to conserved functional domains of viral coat proteins, movement proteins, or replicases and are an approach to obtain broad-spectrum resistance and reduce the environmental risks by inactivating the targets inside and/or outside the plant cell through immunomodulation. The feasibility of this approach has been recently shown for both animal (Chen et al., 1994), (Duan et al., 1994), (Marasco et al., 1993) and plant viral resistance (Tavladoraki et al., 1993), (Voss et al., 1995), (Zimmermann et al., 1998). These antibodies or fragments thereof may be inactivating in themselves or in combination with one or more other antibodies, or a toxin, or in combination with a carrier, transmembrane domain or signal peptide. Importantly, plant pathogen resistance can be enhanced by the co-expression of multiple antibodies.

In a particular preferred embodiment, the present invention relates to one of the above-described antibodies wherein the antibody or a derivative thereof is capable of binding to the functional domain of a viral movement and/or replicase protein. As could be surprisingly demonstrated in Examples 5 and 6, antibodies directed against a viral movement and replicase, respectively, can be used to engineer enhanced resistance against the virus the movement and replicase gene are derived from. The advantage of using the movement or replicase protein as a target for the antibody or a functional equivalent binding protein is that the functional domains within the movement protein and the replicase can be expected to be highly conserved among different viruses. Thus, the expression of an antibody directed against such a conserved epitope of, for example, the movement protein of TMV can also be expected to be effective against related viruses. Furthermore, due to the conservation of the functional domains in these two viral proteins, a further advantage is that the heterogeneity within one single virus group should not be as high as for, e.g., the coat protein. Thus, the finding of the present invention that the movement and replicase protein of a virus are accessible to antibody targeting within a plant cell, a novel concept for the generation of virus resistant plants became feasible. It is therefore, that in one separate aspect the present invention relates to such antibodies for engineering virus resistance in plants. Viruses that can be the target of this approach are any that use movement proteins during infection as well as all viruses that encode a replicase gene. This can be expected to be effective because viral movement is a common feature of many viral infections (McLean et al., Trends Microbiol. 1, (1993), 105–9) and replicases are essential for viral pathogenesis. The importance of approaches targeting these proteins is underscored by the fact that expressing wild type or defective versions of movement or replicase proteins often results in resistance (Beachy, (1997), Curr. Opin. Biotechnol. 8:215–220). Transgenic plants expressing defective mutant TMV movement protein are resistant to multiple viruses, presumably because of disruptions in intercellular viral movement (Cooper et al., (1995), Virology 206, 307–313) and replicase expression is an effective resistance strategy (Anderson et al., (1992), Proc. Natl. Acad. Sci. USA 89:8759–8763; Baulcombe, (1994), Trends Microbiol. 2:60–63; Brederode et al., (1995), Virology 207:467–474; Nguyen et al., (1996), Proc. Natl. Acad. Sci. USA 93:12643–12467; Rubino and Russo, (1995), Virology 212:240–243).

A disadvantage of the current antibody mediated resistance approaches may be the choice of viral coat proteins as target. Plant viral coat proteins have a broad structural diversity and this can restrict the effect of the expressed antibodies to a small range of viruses and under selective stress, the viral coat protein sequence can alter without loss of function. Generation of recombinant antibodies directed against conserved functional domains of viral replicases and movement proteins may provide a better route for obtaining pathogen resistant plants with a broad-spectrum resistance against viruses. The antigen for producing any one of the above-described antibodies can be derived from naturally occurring movement or replicase proteins or fragments thereof or can be recombinantly produced, chemically synthesized and/or derivatized by methods well known to the person skilled in the art some of which are also further discussed herein. In view of the above, the invention also relates to polynucleotides encoding the above-described antibodies, vectors comprising the same and host cells transformed therewith. Suitable vectors, host cells and strategies for the expression of recombinant antibodies in plants are described herein and can be easily adapted from any one of the other embodiments described herein.

Toxins

Toxins include all proteins and peptides that have a detrimental or toxic effect on a pathogen during its life cycle and/or an effect on the pathogen during plant infection or pathogen replication, spread or transmission. This includes toxins that specifically kill an infected host cell and so limit the spread and development of a disease.

Suitable toxins include the following:

toxic peptide(s) which are specific for the pathogen and mediates toxicity e.g. by membrane permeabilisation based on alteration of membrane potential (Ham et al., 1994; Sangster, 1997).

blocking peptides which bind to structural or non structural pathogen proteins, or nucleic acid motifs, and inhibit pathogen function, growth, development or toxicity to the host (Hayakawa, 1991; Silburn et al., 1998).

peptide mimics that bind to pathogen or host protein motifs and that modulate or block the pathogen's replication, e.g. peptide derivatives of proteinase inhibitors that play a physiological role as inhibitors of viral replication and can be used as antiviral agents (Bjorck et al., 1990), (Bjorck et al., 1989).

binding domains, such as antibodies defined above specifically recognising an epitope of a plant pathogen.

peptide mimics that bind to pathogen or host protein motifs and that modulate or block the pathogen's movement within the host plant. As an example, the BC peptide, which mimics the nuclear localisation signal region of HIV-1, reduces HIV-1 production by 75% when expressed in infected dividing cultured human T-cells (Friedler et al., 1998).

toxins which kill the host cell where the pathogen is replicating and has penetrated the cytosol (Barbieri et al., 1993; Hartley et al., 1996; Madshus and Stenmark, 1992), for example (Ribosome inactivating proteins) RIPs which enter the cytosol and are among the most potent cytotoxins known. Ribosome-inactivation is achieved in all cases through the cleavage of an N-glycosidic bond between ribose and a specific adenine residue in the universally conserved sequence 5'-AGUACGA*GAGGA-3' (where A* indicates the target adenine) (SEQ ID NO: 164) located 250–400 nt from the 3' end of 23S/25S/28S rRNAs (Endo and Tsurugi, 1987), (Hartley et al., 1996). Ribosomes depurinated in this manner are unable to bind the EF-2/GTP complex and protein synthesis is blocked at the translocation step (Montanaro et al., 1975). A single RIP molecule is able to depurinate 1000–2000 mammalian cell ribosomes per min under physiological conditions (Eiklid et al., 1980; Endo and Tsurugi, 1988).

proteins and enzymes such as RNase A that are potent cytotoxins (Leland et. al., 1998). These cytotoxic ribonucleases degrade cellular RNA and cause cell death and can be used to kill infected cells and so prevent the proliferation and spread of a pathogen.

These are examples of proteins which will inhibit the replication of a pathogen at a RNA, DNA or protein level by either binding directly to a pathogen protein, replication intermediate or a host factor that is necessary for pathogen replication or movement or transmission and the pathogen life cycle. This strategy is particularly suitable for inactivating viral pathogens. In addition, toxins, such as RIPs or RNase A are described that are suitable for causing cell death on pathogen entry and so halting the spread of infection or proliferation of a pathogen.

In principle all antibodies, proteins, peptides and enzymes that have an activity, that may or may not be enzymatic, which are able to interfere with pathogen life cycles are suitable as part of the present constructs.

In a preferred embodiment of the present invention said enzyme is chitinase or glucanase, glucose oxidase, superoxide dismutase, DNAse or RNAse or RIP or active fragments thereof either singly or in any combination(s).

Constructs

Gene constructs may comprise the following or any combination of the follow and may be encoded on one or more plasmids: Gene constructs may comprise a nucleotide sequence or nucleotide sequences encoding complete recombinant full-size antibodies, dimeric secretory IgA antibodies, multimeric IgM antibodies, the F(ab')$_2$ fragment, the Fab-fragment, the Fv-fragment, single chain antibody fragments (scFvs), single binding domains (dAbs), a bivalent scFv (diabody) (Poljak, 1994), minibody (Carter and Merchant, 1997), bispecific scFv antibodies (Plückthun and Pack, 1997; Fischer et al. *Eur. J. Biochem.* 262, 810–816 (1999)) where the antibody molecule recognises two different epitopes that may come from the pathogen or the host or both, triabodies and any other part of the antibody (molecular recognition units (MRUs)) which shows binding to the target epitopes. Genes encoding these suitable recombinant antibody fragment(s) may be derived from vertebrates, camelids, avian or pisces species.

In the constructs according to the invention, the antibody is preferably fused to a complete sequence of a toxic agent or a part thereof which still has activity, or which is still functionally active. Also, the chimeric protein may be encoded by nucleotide sequences on one or more constructs and may be assembled in vivo by the plant or expression organisms protein assembly and translation machinery. The chimeric protein can also be obtained by biochemical assembly or in vitro or in vivo assembly of the chimeric immunotoxin subunits using the cells endogenous protein assembly machinery. The antibody, antibodies or fragments thereof are fused directly to the toxic agent or linked by a flexible spacer which does not interfere with the structure or function of the two proteins. Such flexible linkers include copies of the (Glycine-Glycine-Glycine-Glycine-Serine)$_n$ linker (SEQ ID NO: 165—also referred to as Gly$_4$Ser), where n is 1 to 4 or more copies of the linker unit, the Genex 212 and 218 linker and the flexible linker peptide of *Trichoderma reesi* cellobiohydrolase I (CBHI) (Turner et al., 1997), (Tang et al., 1996).

Constructs for Cellular Targeting and Membrane Locallsation

In this invention, this targeting approach has the advantage that the molecular pathogenicide or antibody or fragment thereof can be expressed where the pathogen is most vulnerable to the action of the molecular pathogenicide and/or antibody or fragment thereof.

The desired cellular location of the molecular pathogenicide, or any components thereof, can be achieved by using the appropriate cellular targeting signals, these include but are not limited to signal peptides, targeting sequences, retention signals, membrane anchors, post translational modifications and/or membrane transmembrane domains that target the protein to the desired organelle, desired membrane (plasma membrane, ER, Golgi, nucleus, chloroplast or vacuole) or desired membrane orientation (cytoplasmic or lumenal or plant cell membrane display) (Kim et al., 1997; Rose and Fink, 1987). Localisation sequences can be targeting sequences which are described, for example in chapter 35 (protein targeting) of L. Stryer *Biochemistry* 4$^{th}$ edition, W.H. Freeman, 1995. Proteins synthesised without a functional signal peptide are not co-translationally inserted into the secretory pathway and remain in the cytosol. Proteins that carry a signal peptide that directs them to the secretory pathway, which may include a transmembrane sequence or membrane anchor, will be targeted for secretion by default or reside in their target membrane organelles. Targeting signals can direct proteins to the ER, retain them in the ER (LYSLYS motif (SEQ ID NO: 166) and KDEL (SEQ ID NO: 167)), TGN 38, or will target proteins to cell organelles such as the chloroplasts, vacuole, nucleus, nuclear membrane, peroxisomes and mitochondria. Examples for signal sequences and targeting peptides are described in (von Heijne, 1985) (Bennett and Osteryoung, 1991) (Florack et al., 1994). In addition, the targeting signals may be cryptic and encoded by a host plant cell or heterologous eukaryotic cell proteins or animal proteins where the localisation is known and where the protein can be cloned. By constructing a fusion protein with this protein, a molecular pathogenicide can be targeted to the localisation of the protein without the need for identification of the cryptic targeting signal. Suitable cryptic signals are those encoded by the resident Golgi enzymes.

The molecular pathogenicidds described in this invention can be targeted to cellular membranes by incorporating heterologous sequences into the recombinant protein which permit its synthesis as a membrane protein or as a membrane associated protein or its post translational modification to associate it with cellular membranes. Suitable membrane anchor Sequences, enabling the integration of recombinant antibody fusion proteins and tarts thereof in the plasma membrane, include the human T cell receptor transmembrane domains (Gross and Eshhar, 1992), glycophosphatidyl inositol (GPI) anchors (Gerber et al., 1992), immunoglobulin superfamily membrane anchors, tetraspan family members (Tedder and Engel, 1994; Wright and Tomlinson, 1994) and any transmembrane sequence(s) from a known protein or synthesised sequences that have a-similar function and can be included in the target protein by recombinant DNA technology.

In addition, the antibodies or parts thereof, or the recombinant antibody fusion proteins, or parts thereof, may be targeted to cell membranes where they could face the cytosolic side of the membrane. Suitable targeting sequences for cytoplasmic display, include the transmembrane domains of: KAR1, for nuclear membrane integration (Rose and Fink, 1987), middle-T antigen (Kim et al., 1997), for plasma membrane integration and cytochrome b5, for ER membrane integration (Kim et al., 1997). C-terminal linkages to fatty acids using consensus amino acid sequences leading to post translational prenylation, farnesylation, palmitoylation, myristoylation or ankyrin sequence motifs can also be used.

Constructs for Antibody Stabilisation by Membrane Display

Pathogen-specific recombinant antibodies can be fused to different transmembrane anchors to improve the expression levels and stability of these molecules inside the plant cell, by targeting the expressed recombinant protein to cell membranes in various orientations. This can be accomplished by adding:

a) C-terminal localisation sequences to target and integrate recombinant cytosolic proteins with N-terminal leader peptides into the bilayer of cellular membranes, thus facing to the plant apoplast. Suitable membrane, localisation sequences include the human T cell receptor β chain transmembrane domain and the human platelet derived growth factor receptor (PDGFR) transmembrane domain, glyco-phosphatidyl inositol (GPI) anchors, immunoglobulin superfamily membrane anchors and any transmembrane sequence(s) from a known protein or synthesised sequences that have a similar function and can be included in the target protein by recombinant DNA technology.

b) Amino terminal transmembrane proteins with either dual or tetrameric plasma membrane spanning domains to expose both the N- and C-termini of secretory recombinant proteins to the cytosol. This can be achieved by using suitable members of the tetraspan family including CD9, CD20, CD81 and the In-Hc-lc dualspan typeII–IV hybrid of the MHC invariant chain and H-$2^d$ hybrid protein. This method enables the orientation of a secreted and membrane anchored antibody construct with its N- and C-terminus into the cytosol. Alternatively fusions to SNAP-25 can be used for the same orientation.

c) C-terminal anchor sequences to target and integrate recombinant cytosolic proteins without N-terminal leader peptides into the bilayer of endomembranes posttranslationally. Suitable targeting sequences include transmembrane domains of KAR1 for nuclear membrane integration (Rose and Fink, 1987), middle-T antigen for plasma membrane integration (Kim et al., 1997) and cytochrome b5 for ER membrane integration (Kim et al., 1997).

d) Addition of consensus motifs to the protein that permit C-terminal linkages to fatty acids by prenylation, farnesylation, palmitoylation, myristoylation in the cytosol which then lead to membrane integration.

e) Addition of ankyrin sequence motifs (Lambert and Bennett, 1993; Peters and Lux, 1993).

Constructs for In Vivo Protein Complex Assembly

In addition, the antibody or fragment thereof can be encoded by a separate nucleotide sequence to that of the toxin and the antibody and toxin, either of which may encode membrane localisation or cellular targeting sequences, can be encoded by one or more vectors, e.g., plasmids. The constructs contain nucleotide sequences encoding complimentary binding proteins so that when the antibody, or fragment thereof, is genetically fused to one binding partner and the toxin, or fragment thereof, is genetically fused to the second binding partner, these two independent proteins will bear mutually recognising binding activities. When these two independent proteins are expressed in the same plant compartment, the binding domains will bind to form a molecular pathogenicide with two subunits and similar properties to an antibody-toxin fusion protein. Suitable binding domains/partners include:

A single chain antibody and its corresponding epitope, where the single chain binds to the epitope and thereby enables binding between two independent proteins, leucine zippers (Carter et al., 1995), Antibody heavy and light chains, where one protein is fused to the heavy chain and assembly of heavy and light chain takes place in the ER, other homo- or hetero-binding domains.

Anyone of ordinary skill in the art will recognise that the component antibody, antibodies or fragments thereof or component pathogen binding peptides, as described, and component toxin or fragments thereof can each bear a binding partner. When expressed in the same compartment of a plant, or when encountering each other, these binding domains can then permit the assembly of a molecular pathogenicide with all the properties required from the components. Anyone skilled in the art will recognise that this can be achieved by other means than those described above which are intended as examples to better illustrate the principle of in vivo assembly and are not intended to be taken as a limiting or a comprehensive description.

Carrier Proteins

Anyone skilled in the art will also recognise that the various components of the present invention can be expressed in such a way that they are on the surface of a third carrier protein, suitable carriers include glutathione S-transferase (GST) encoded by *Schistosoma japonicum* (Smith and Johnson, 1988), TMV coat protein, maltose-binding protein and thioredoxin (LaVallie et al., 1993) or other proteins. In addition, any of the components of the present invention may be tagged with a genetically encoded fluorophore, suitable fluorophores include, but are not limited to, the green fluorescent protein (GFP) from *Aequonria victoria*. This approach would be especially useful for monitoring the localisation of a pathogen or molecular pathogenicide during infection.

If the fusion protein or proteins are expressed in a heterologous organism for production of the protein or proteins, it may be necessary to modify the gene construct in order to match the codon preference of the organism and to remove mRNA motifs that reduce the stability of the transcript.

All of the components of the molecular pathogenicides described in this invention can be separately transformed into plant lines which can then be sexually crossed to give offspring that product the molecular pathogenicides in a functional form.

Anyone skilled in the art will recognise that the antibodies, peptides and toxins can be combined in several forms and encoded on different plasmids to produce proteins that have the desired effect on the pathogen. Anyone skilled in the art will also recognise that assembling the molecular pathogenicides from individually genetically encoded subunits can be achieved by several methods.

Target Pathogens

Viruses, bacteria, mycoplasmas, fungi, nematodes, insects and other pathogens.

Vectors

The present invention also relates to vectors, particularly plasmids, cosmids, viruses, bacteriophages and other vectors used conventionally in genetic engineering that contain a polynucleotide according to the invention or any one of the above-described gene constructs. Methods which are well known to those skilled in the art can be used to construct various plasmids and vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1989), (1994). Alternatively, the polynucleotides and vectors of the invention can be reconstituted into liposomes for delivery to target cells.

In a preferred embodiment, the polynucleotide present in the vector is linked to regulatory elements which allow the expression of the polynucleotide in prokaryotic and/or eukaryotic cells. Expression comprises transcription of the nucleic acid molecule preferably into a translatable mRNA. Regulatory elements ensuring expression in prokaryotic and/or eukaryotic cells are well known to those skilled in the art. In the case of eukaryotic cells they comprise normally promoters ensuring initiation of transcription and optionally poly-A signals ensuring termination of transcription and stabilisation of the transcript, for example, those of the 35S RNA from Cauliflower Mosaic Virus (CaMV). In this respect, the person skilled in the art will readily appreciate that the polynucleotides encoding at least one of the above-described domains of the fusion proteins or pathogenicide of the invention may encode all of the domains or only one. Likewise, said polynucleotides may be under the control of the same promoter or may be separately controlled for expression. Other promoters commonly used are the Figwort Mosaic virus promoter, the polyubiquitin promoter, and the actin promoter for ubiquitous expression. The termination signals usually employed are from the Nopaline Synthase or CaMV 35S gene. A plant translational enhancer often used is the TMV omega sequences, the inclusion of an intron (Intron-1 from the Shrunken gene of maize, for example) has been shown to increase expression levels by up to 100-fold. (Maiti et al., Transgenic Research 6 (1997), 143–156; Ni et al., Plant Journal 7 (1995), 661–676). Additional regulatory elements may include transcriptional as well as translational enhancers.

Possible regulatory elements permitting expression in prokaryotic host cells comprise, e.g., the $P_L$, lac, trp or tac promoter in *E. coli*, and examples for regulatory elements permitting expression in eukaryotic host cells are the AOX1 or GAL1 promoter in yeast or the CMV-, SV40- , RSV-promoter (Rous sarcoma virus), CMV-enhancer, SV40-enhancer or a globin intron in mammalian and other animal cells. In this context, suitable expression vectors are known in the art such as Okayama-Berg cDNA expression vector pcDV1 (Pharmacia), pCDM8, pRc/CMV, pcDNA1, pcDNA3 (In-vitrogene), pSPORT1 (GIBCO BRL). Advantageously, the above-described vectors of the invention comprises a selectable and/or scorable marker. Selectable marker genes useful for the selection of transformed hosts, for example plant cells, callus, plant tissue and plants are well known to those skilled in the art and comprise, for example, antimetabolite resistance as the basis of selection for dhfr, which confers resistance to methotrexate (Reiss, Plant Physiol. (Life Sci. Adv.) 13 (1994), 143–149); npt, which confers resistance to the aminoglycosides neomycin, kanamycin and paromycin (Herrera-Estrella, EMBO J. 2 (1983), 987–995) and hygro, which confers resistance to hygromycin (Marsh, Gene 32 (1984), 481–485). Additional selectable genes have been described, namely trpB, which allows cells to utilise indole in place of tryptophan; hisD, which allows cells to utilise histinol in place of histidine (Hartman, Proc. Natl. Acad. Sci. USA 85 (1988), 8047); mannose-6-phosphate isomerase which allows cells to utilise mannose (WO 94/20627) and ODC (ornithine decarboxylase) which confers resistance to the ornithine decarboxylase inhibitor, 2-(difluoromethyl)-DL-ornithine, DFMO (McConlogue, 1987, In: Current Communications in Molecular Biology, Cold Spring Harbor Laboratory ed.) or deaminase from Aspergillus terreus which confers resistance to Blasticidin S (Tamura, Biosci. Biotechnol. Biochem. 59 (1995), 2336–2338).

Useful scorable markers are also known to those skilled in the art and are commercially available. Advantageously, said marker is a gene encoding luciferase (Giacomin, PI. Sci. 116 (1996), 59–72; Scikantha, J. Bact. 178 (1996), 121), green fluorescent protein (Gerdes, FEBS Lett. 389 (1996), 44–47) or β-glucuronidase (Jefferson, EMBO J. 6 (1987), 3901–3907). This embodiment is particularly useful for simple and rapid screening of cells, tissues and organisms containing a vector of the invention.

Host Cells and Expression of Fusion Proteins and Pathogenicides

The present invention furthermore relates to host cells comprising a vector as described above or a polynucleotide according to the invention. The vector or polynucleotide according to the invention which is present in the host cell may either be integrated into the genome of the host cell or it may be maintained in some form extrachromosomally.

The host cell can be any prokaryotic or eukaryotic cell, such as bacterial, insect, fungal, plant or animal cells. Preferred fungal cells are, for example, those of the genus Saccharomyces, in particular those of the species *S. cerevisiae*.

Another subject of the invention is a method for the preparation of the above-described fusion proteins and pathogenicides which comprises the cultivation of host cells according to the invention which, due to the presence of a vector or a polynucleotide according to the invention, are able to express such a protein, under conditions which allow expression and optionally assembly of the fusion protein or pathogenicide and recovering of the so-produced protein from the culture. Depending on the specific constructs and conditions used, the protein may be recovered from the cells, from the culture medium or from both. For the person skilled in the art it is well known that it is not only possible to express a native protein but also to express the protein as fusion polypeptides or to add signal sequences directing the protein to specific compartments of the host cell, e.g., ensuring secretion of the peptide into the culture medium, etc. Furthermore, such a protein and fragments thereof can be chemically synthesised and/or modified according to standard methods described, for example herein.

The present invention furthermore relates to molecular pathogenicides encoded by the polynucleotides according to the invention or produced by the above-described method. In this context, it is also understood that the fusion proteins and pathogenicides according to the invention may be further modified by conventional methods known in the art.

Plant Promoters and Expression Control Elements

The fusion constructs are expressed in plants either stably in transgenic plants or transiently under the control of any type of promoter that is active in plants. For long-term resistance in host plants, high yield production of recombinant proteins, stable expression is preferred.

In general, such regulatory elements comprise a promoter active in plant cells. To obtain expression in all tissues of a transgenic plant, preferably constitutive promoters are used, such as the 35 S promoter of CaMV (Odell, Nature 313 (1985), 810–812) or promoters of the polyubiquitin genes of maize (Christensen, Plant Mol. Biol. 18 (1982), 675–689). In order to achieve expression in specific tissues of a transgenic plant it is possible to use tissue specific promoters (see, e.g., Stockhaus, EMBO J. 8 (1989), 2245–2251). Further examples are:
a) Expression control elements (e.g. promoters listed below in b to f, enhancer sequences, transcriptional and translational enhancers, transcription terminators, polyadenylation sites etc.) and a selectable marker if necessary.

b) Constitutive promoters such as the CaMV-35S (Benfey et al., 1989) and the nos promoter (Mitra and Gynheung, 1989).
c) Viral subgenomic promoters.
d) Tissue specific promoters and chimeric promoters (Ni et al., 1995), (Comai et al., 1990).
e) Inducible promoters (Caddick et al., 1998).
f) Transient expression systems (Kapila et al., 1997).

Known are also promoters which are specifically active in tubers of potatoes or in seeds of different plants species, such as maize, Vicia, wheat, barley etc. Inducible promoters may be used in order to be able to exactly control expression. An example for inducible promoters are the promoters of genes encoding heat shock proteins. Also microspore-specific regulatory elements and their uses have been described (WO96/16182). Furthermore, the chemically inducible Tet-system may be employed (Gatz, Mol. Gen. Genet. 227 (1991); 229–237). Further suitable promoters are known to the person skilled in the art and are described, e.g., in Ward (Plant Mol. Biol. 22 (1993), 361–366). The regulatory elements may further comprise transcriptional and/or translational enhancers functional in plants cells. Furthermore, the regulatory elements may include transcription termination signals, such as a poly-A signal, which lead to the addition of a poly A tail to the transcript which may improve its stability.

Furthermore, it is in principle possible to modify the coding sequence in such a way that the protein is located in any desired compartment of the plant cell. These include the endoplasmatic reticulum, the vacuole, the mitochondria, the plastids, the apoplast, the cytoplasm etc. Methods how to carry out this modifications and signal sequences ensuring localisation in a desired compartment are well known to the person skilled in the art.

Transformation

Methods for the introduction of foreign DNA into plants are also well known in the art. These include, for example, the transformation of plant cells or tissues with T-DNA using Agrobacterium tumefaciens or Agrobacterium rhizogenes, the fusion of protoplasts, direct gene transfer (see, e.g., EP-A 164 575), injection, electroporation, biolistic methods like particle bombardment and other methods known in the art. The vectors used in the method of the invention may contain further functional elements, for example "left border"- and "right border"-sequences of the T-DNA of Agrobacterium which allow for stably integration into the plant genome. Furthermore, methods and vectors are known to the person skilled in the art which permit the generation of marker free transgenic plants, i.e. the selectable or scorable marker gene is lost at a certain stage of plant development or plant breeding. This can be achieved by, for example cotransformation (Lyznik, Plant Mol. Biol. 13 (1989), 151–161; Peng, Plant Mol. Biol. 27 (1995), 91–104) and/or by using systems which utilise enzymes capable of promoting homologous recombination in plants (see, e.g., WO097/08331; Bayley, Plant Mol. Biol. 18 (1992), 353–361; Lloyd, Mol. Gen. Genet. 242 (1994), 653–657; Maeser, Mol. Gen. Genet. 230 (1991), 170–176; Onouchi, Nucl. Acids Res. 19 (1991), 6373–6378). Methods for the preparation of appropriate vectors are described by, e.g., Sambrook (Molecular Cloning; A Laboratory Manual, 2nd Edition (1989), Cold Spring Harbor Laboratory Press, Cold Spring Harbor, N.Y.). Suitable strains of *Agrobacterium tumefaciens* and vectors as well as transformation of Agrobacteria and appropriate growth and selection media are well known to those skilled in the art and are described in the prior art (GV3101 (pMK90RK), Koncz, Mol. Gen. Genet. 204 (1986), 383–396; C58C1 (pGV 3850kan), Deblaere, Nucl. Acid Res. 13 (1985), 4777; Bevan, Nucleic. Acid Res. 12(1984), 8711; Koncz, Proc. Natl. Acad. Sci. USA 86 (1989), 8467–8471; Koncz, Plant Mol. Biol. 20 (1992), 963–976; Koncz, Specialised vectors for gene tagging and expression studies. In: Plant Molecular Biology Manual Vol 2, Gelvin and Schilperoort (Eds.), Dordrecht, The Netherlands: Kluwer Academic Publ. (1994), 1–22; EP-A-120 516; Hoekema: The Binary Plant Vector System, Offsetdrukkerij Kanters B. V., Alblasserdam (1985), Chapter V, Fraley, Crit. Rev. Plant. Sci., 4, 1–46; An, EMBO J. 4 (1985), 277–287). Although the use of *Agrobacterium tumefaciens* is preferred in the method of the invention, other Agrobacterium strains, such as *Agrobacterium rhizogenes*, may be used, for example if a phenotype conferred by said strain is desired.

Methods for the transformation using biolistic methods are well known to the person skilled in the art; see, e.g., Wan, Plant Physiol. 104 (1994), 37–48; Vasil, Bio/Technology 11 (1993), 1553–1558 and Christou (1996) Trends in Plant Science 1, 423–431. Microinjection can be performed as described in Potrykus and Spangenberg (eds.), Gene Transfer To Plants. Springer Verlag, Berlin, N.Y. (1995).

The transformation of most dicotyledonous plants is possible with the methods described above. But also for the transformation of monocotyledonous plants several successful transformation techniques have been developed. These include the transformation using biolistic methods as, e.g., described above as well as protoplast transformation, electroporation of partially permeabilized cells, introduction of DNA using glass fibers, etc.

Transformation can be done using any method that leads to expression of construct or constructs in a plant and these methods can be used for stable transformation where the gene of interest is incorporated in the host plant DNA or where the construct is transiently expressed. Examples of transformation technology include:

a) *Agrobactetum tumefaciens* or *Agrobacterium rhizogenes* mediated transformation (Turpen et al., 1993; White, 1992): based on the insertion of a foreign DNA sequence into the plant genome carried on a plasmid DNA within the agrobacteria. The foreign gene is inserted into the plant genome together with bacterial plasmid sequences.
b) Particle bombardment (Sanford et al., 1990), (Klein and Fitzpatrick-McElligott, 1993) or biolistic process (Furth, 1997): Particle bombardment uses particles coated with the DNA that penetrate the plant cell at high velocity and the DNA is incorporated into the host genome by host recombination processes. Besides particle bombardment biolistic processes also include injection methods.
c) Tissue electroporation (Chowrira et al., 1995; D'Halluin et al., 1992): under the influence of an electric field, DNA enters pores in the plant cell membrane and is incorporated into the plant genome by recombination.
d) Use of liposomes or methods which increase the uptake of free DNA (Spörlein and Koop, 1991; White, 1992).
e) Any method for integration of foreign DNA in a plant cell resulting in transiently or stably transformed plants.

Target Plants

The present invention relates to transgenic plant cells which contain a polynucleotide, vector or composition of vectors of the invention. Preferably, said polynucleotide or vector is stably integrated into the genome.

As is immediately evident to the person skilled in the art, the vectors of the present invention can carry nucleic acid molecules encoding the domains of the antibody, fusion protein or pathogenicide of the invention either alone or in combination. The same applies to the above described plant cells, plant tissue and plants transformed therewith. Likewise, said nucleic acid molecules may be under the control of the same regulatory elements or may be separately controlled for expression. In this respect, the person skilled in the art will readily appreciate that the nucleic acid molecules encoding the domains of the fusion protein or pathogenicide can be expressed in the form of a single mRNA as transcriptional and optionally translational fusions. This means that domains are produced as separate polypeptides or in the latter option as a fusion polypeptide that is further processed into the individual proteins, for example via a cleavage site for proteinases that has been incorporated between the amino acid sequences of both proteins. The resultant protein domains can then self-assemble in vivo. Of course, the domains may also be expressed as a bi- or multifunctional polypeptide, preferably disposed by a peptide linker which advantageously allows for sufficient flexibility of both proteins. Preferably said peptide linker comprises plural, hydrophilic, peptide-bonded amino acids of a length sufficient to span the distance between the C-terminal end of one of said proteins and the N-terminal end of the other of said proteins when said polypeptide assumes a conformation suitable for biological activity of both proteins when disposed in aqueous solution in the plant cell. Examples of the above-described expression strategies can be found in the literature, e.g., for dicistronic mRNA (Reinitiation) in Hefferon, J. Gen. Virol. 78 (1997), 3051–3059, fusion proteins are described in Brinck-Peterson, Plant Mol. Biol. 32 (1996), 611–620 and Hotze, FEBS Lett. 374 (1995), 345–350; bifunctional proteins are discussed in Lamp, Biochem. Biophys. Res. Corn. 244 (1998), 110–114 and Dumas, FEBS Lett. 408 (1997), 156–160 and for linker peptide and protease it is referred to Doskeland, Biochem. J. 313 (1996), 409–414.

In a preferred embodiment of the invention, the transgenic plant cell comprises a selectable marker. As described above, various selectable markers can be employed in accordance with the present invention. Advantageously, selectable markers may be used that are suitable for direct selection of transformed plants, for example, the phophinothricin-N-acetyltransferase gene the gene product of which detoxifies the herbicide L-phosphinothricin (glufosinate or BASTA); see, e.g., De Block, EMBO J. 6 (1987), 2513–2518 and Dröge, Planta 187 (1992), 142–151.

The presence and expression of the polynucleotides or vectors in the transgenic plant cells leads to the synthesis of a fusion protein, antibody or pathogenicide of the invention or assembly of the same which has an influence on pathogen resistance in plants containing such cells.

Thus, the present invention also relates to transgenic plants and plant tissue comprising transgenic plant cells according to the invention. Due to the expression of a fusion protein, the antibody against the viral movement and/or replicase protein or pathogenicide of the invention or their domains, e.g., in cellular compartments and/or plant tissue these transgenic plants may show various physiological, developmental and/or morphological modifications in comparison to wild-type plants. Advantageously, these transgenic plants display a resistance against a pathogen that the corresponding wild type plant was susceptible to.

In general, the plants which can be modified according to the invention can be derived from any desired plant species. They can be monocotyledonous plants or dicotyledonous plants, preferably they belong to plant species of interest in agriculture, wood culture or horticulture, such as crop plants (e.g. maize, rice, barley, wheat, rye, oats etc.), potatoes, oil producing plants (e.g. oilseed rape, sunflower, pea nut, soy bean, etc.), cotton, sugar beet, sugar cane, leguminous plants (e.g. beans, peas etc.), wood producing plants, preferably trees, etc.

In yet another aspect, the invention also relates to harvestable parts and to propagation material of the transgenic plants according to the invention. Harvestable parts can be in principle any useful parts of a plant, for example, leaves, stems, fruit, flowers, seeds, roots etc. Propagation material includes, for example, seeds, fruits, cuttings, seedlings, tubers, rootstocks etc.

Kits

In addition, the present invention relates to a kit comprising the above-described antibodies, fusion protein, pathogenicide, polynucleotide or vectors. The kit of the invention may contain further ingredients such as selection markers and components for selective media suitable for the generation of transgenic plant cells, plant tissue or plants. The kit of the invention may advantageously be used for carrying out the method of the invention and could be, inter alia, employed in a variety of applications, e.g., in the diagnostic field or as research tool. The parts of the kit of the invention can be packaged individually in vials or in combination in containers or multicontainer units. Manufacture of the kit follows preferably standard procedures which are known to the person skilled in the art. The kit or its ingredients according to the invention can be used in plant cell and plant tissue culture, for example in agriculture. The kit of the invention and its ingredients are expected to be very useful in breeding new varieties of, for example, plants which display improved properties such as those described herein.

It is also immediately evident to the person skilled in the art that the polynucleotides and vectors of the present invention can be employed to produce transgenic plants with a further desired trait due to genetic engineering (see for review TIPTEC Plant Product & Crop Biotechnology 13 (1995), 312–397). This can be, for example, an acquired resistance to other pathogens or quality improvements of the plants comprising (i) herbicide tolerance (DE-A-3701623; Stalker, Science 242 (1988), 419), (ii) insect resistance (Vaek, Plant Cell 5 (1987), 159–169), (iii) virus resistance (Powell, Science 232 (1986), 738–743; Pappu, World Journal of Microbiology & Biotechnology 11 (1995), 426–437; Lawson, Phytopathology 86 (1996), 56 suppl.), (vi) ozone resistance (Van Camp, BioTech. 12 (1994), 165–168), (v) improving the preserving of fruits (Oeller, Science 254 (1991), 437–439), (vi) improvement of starch composition and/or production (Stark, Science 242 (1992), 419; Visser, Mol. Gen. Genet. 225 (1991), 289–296), (vii) altering lipid composition (Voelker, Science 257 (1992), 72–74), (viii) production of (bio)polymers (Poirer, Science 256 (1992), 520–523), (ix) alteration of the flower colour, e.g. by manipulating the anthocyanin and flavonoid biosynthetic pathway (Meyer, Nature 330 (1987), 667–678, WO90/12084), (x) resistance to bacteria, insects and fungi (Duering, Molecular Breeding 2 (1996), 297–305; Strittmatter, Bio/Technology 13 (1995), 1085–1089; Estruch, Nature Biotechnology 15 (1997), 137–141), (xi) inducing and maintaining male and/or female sterility (EP-A1 0 412 006; EP-A1 0 223 399; WO93/25695) and (xii) remediation of contaminated soils (Cunningham, TIBTECH 13 (1995), 393–397).

These and other embodiments are disclosed and encompassed by the description and examples of the present invention. Further literature concerning any one of the methods, uses and compounds to be employed in accordance with the present invention may be retrieved from public libraries, using for example electronic devices. For example the public data base "Medline" may be utilised which is available on the Internet, for example at the following World Wide Web domain site address "ncbl.nlm.nih.gov/PubMed/medline.html". Further databases and addresses such as those found at the World Wide Web domain site addresses "ncbi.nlm.nih.gov", "infoblogen.fr", "fmi.ch/biology/research_tools.html", and "tigr.org" are known to the person skilled in the art and can also be obtained using search engines such as "lycos.com". An overview of patent information in biotechnology and a survey of relevant sources of patent information useful for retrospective searching and for current awareness if given in Berks, TIBTECH 12 (1994) 352–364.

DESCRIPTION OF THE FIGURES

FIG. 1 shows a description of various orientations for molecular pathogenicide display on cellular membranes. Recombinant molecular pathogenicides can be targeted by cellular signals and expressed in several orientations on cellular membranes, for example: A: where the recombinant protein faces the cytosol or extracellular space after fusion to a transmembrane domain or after post translational lipid modification and B: where the recombinant protein is fused to a protein with 4 transmembrane domains. In C and D possible orientations of toxins are displayed. In addition, the toxin and or recombinant antibody fragment can be fused to the c terminal of any of the example protein structures.

N: protein amino terminal; C: protein carboxy terminal; tm: transmembrane domain; rAb: recombinant antibody fragment or binding domain.

Figure 2:
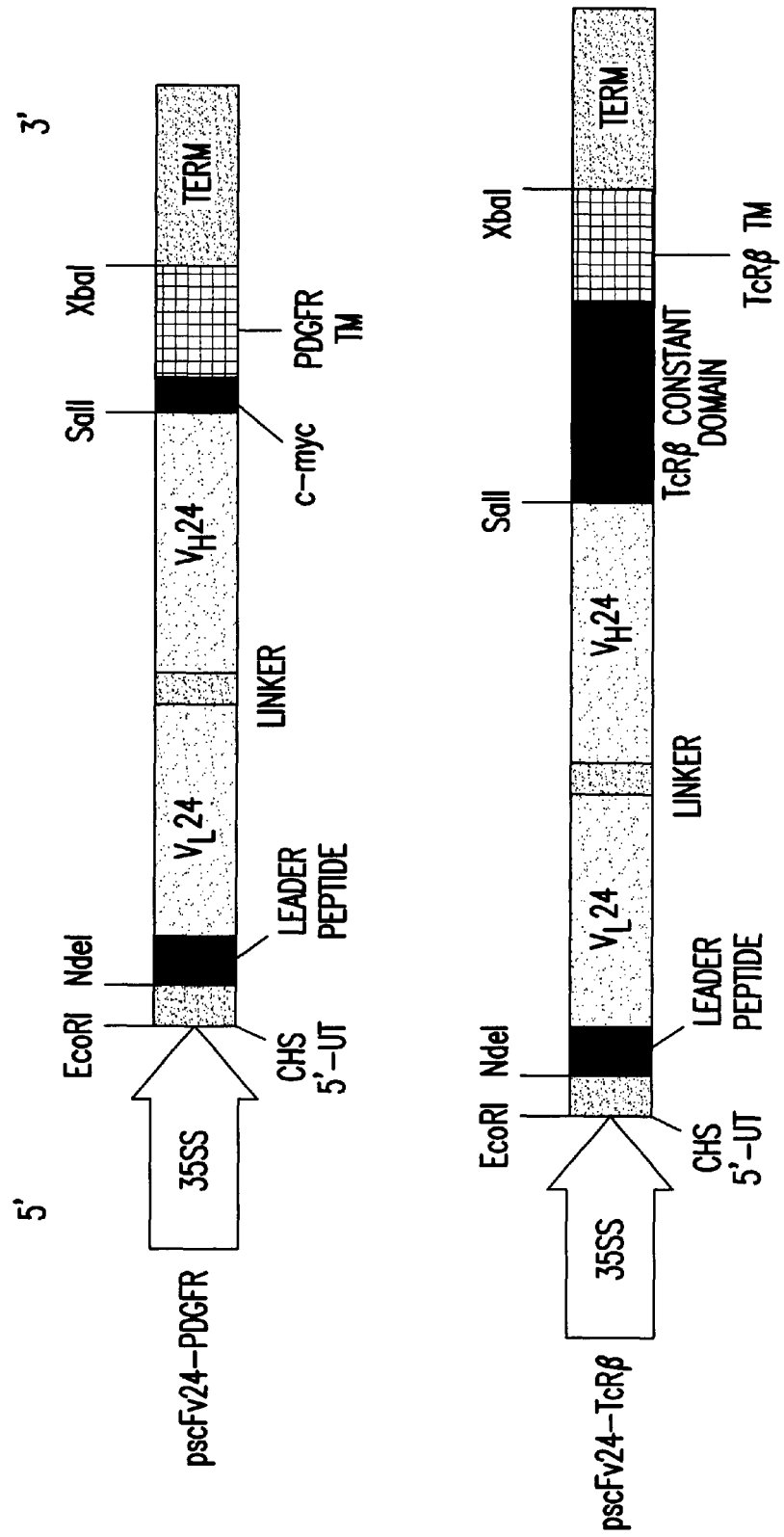

FIG. 2 shows example constructs for membrane anchoring of scFv24 in the plant cell plasma membrane (see example 1). 35SS: 35S promoter from Cauliflower Mosaic Virus with duplicated enhancer; CHS 5'-UT: chalcone synthase 5' untranslated region; Leader peptide: original murine leader sequence from the parental monoclonal antibody 24 light chain; $V_L$: Variable domain of the parental monoclonal antibody 24 light chain; $V_H$: Variable domain of the parental monoclonal antibody 24 heavy chain; Linker: 14 amino acid linker sequence; c-myc: c-myc epitope tag sequence; TcRβ: Human T cell receptor β chain; PDGFRTM: Platelet derived growth factor receptor transmembrane domain; Term: termination sequence from Cauliflower mosaic virus.

Figure 3:
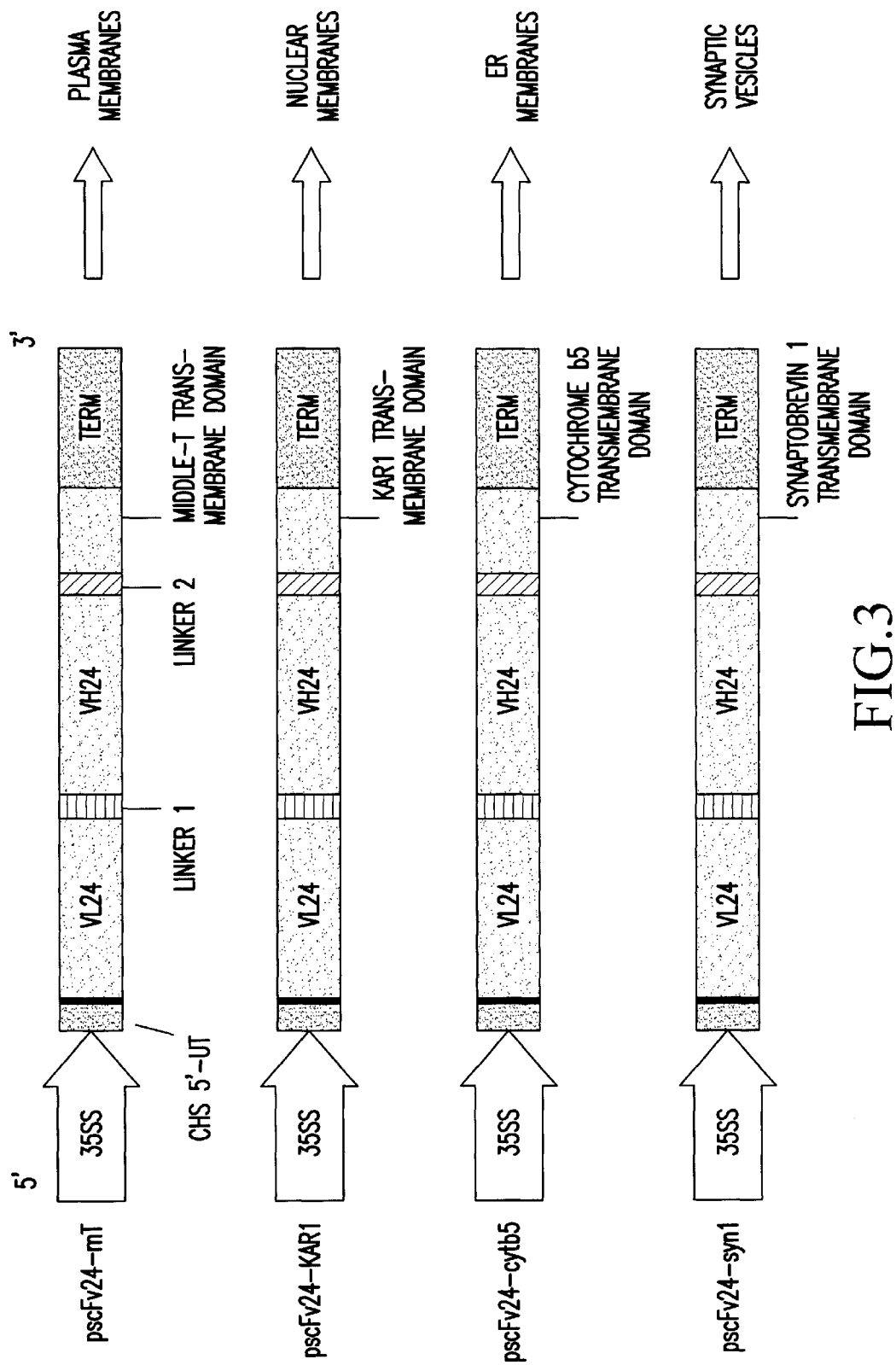

FIG. 3 shows example constructs for molecular pathogenicide display facing the cell cytoplasm. 35SS: 35S promoter from Cauliflower Mosaic Virus with duplicated enhancer; CHS 5'-UT: chalcone synthase 5' untranslated region; VL: Variable domain of the parental monoclonal antibody 24 light chain; VH: Variable domain of the parental monoclonal antibody 24 heavy chain; Linker 1: 14 amino acid linker (Genex 212) sequence; Linker 2: 10 amino acid linker (Gly4Ser)2 sequence (SEQ ID NO: 168); Term: termination sequence from Cauliflower mosaic virus.

Figure 4:
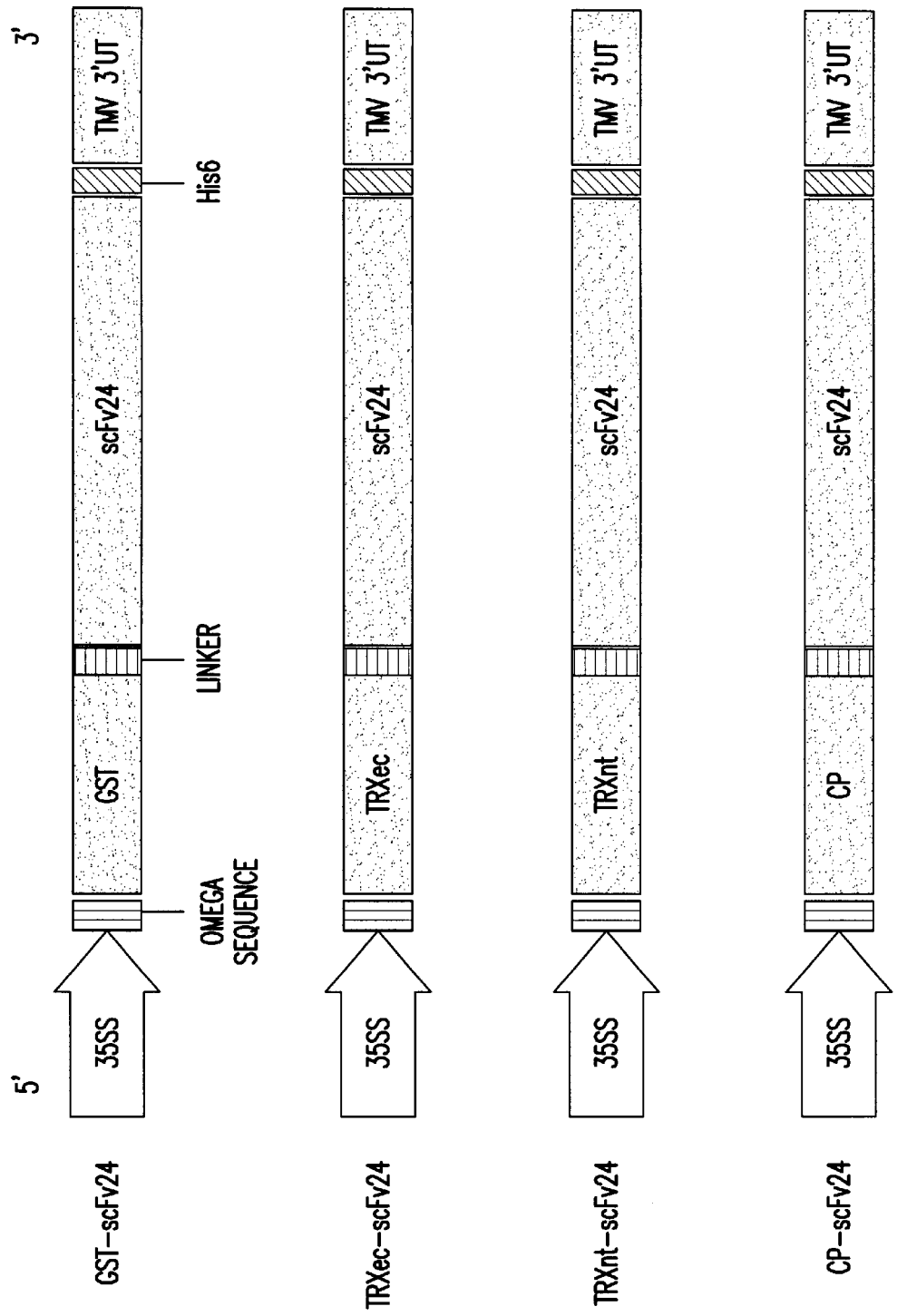

FIG. 4 shows example constructs for viral coat protein antibody fusion proteins and various potential carrier antibody-protein fusion proteins. scFv24: single chain antibody derived from parental monoclonal mAb24 recognising a neotope on the surface of intact TMV virions; GST: Glutathione S-transferase from *Schistosoma japonicum*; Omega sequence: Tobacco Mosaic virus 5' untranslated region; linker: 10 Amino acid (Gly$_4$Ser)$_2$ linker sequence; His6: 6 histidine residue epitope tag sequence; 35SS: 35S promoter from Cauliflower Mosaic Virus with duplicated enhancer; TRXec: Thioredoxin from *Escherichia coli*; TRXnt: Thioredoxin from *Nicotiana tabacum*; CP: coat protein monomer from Tobacco mosaic virus; TMV 3' UT: Tobacco Mosaic virus 3' untranslated region.

FIG. 5 shows the strategy and example constructs for in vivo molecular pathogenicide assembly using an antibody: antigen interaction as the binding partners for in vivo assembly. The two binding partners are an epitope tag and a high affinity antibody which specifically recognises this epitope tag. To assemble a molecular pathogenicide protein complex, the epitope specific antibody is genetically fused to a pathogen specific antibody and the epitope tag is genetically fused to the toxin sequence. Both of these recombinant proteins are then expressed in the same cell compartment. The epitope specific antibody binds the epitope expressed on the surface of the toxin. This high affinity interaction then gives a molecular pathogenicide protein complex, which specifically recognises the pathogen and bears a toxic activity. Linker 4 can encode specific protease cleavage sites. The epitope and pathogen specific antibodies can also be included in the constructs in the same orientation but where the epitope specific antibody precedes the pathogen specific antibody in the 5' to 3' direction.

A: schematic of molecular pathogenicide protein complex assembly in a cell compartment; B: Example constructs showing two possible arrangements (Ab1 and Ab2) of the individual $V_L$ and $V_H$ domains of both the pathogen specific and epitope specific antibody fragments; C: two possible arrangements (Tox 1 and Tox2) for epitope toxin fusion proteins.

Figure 6A:
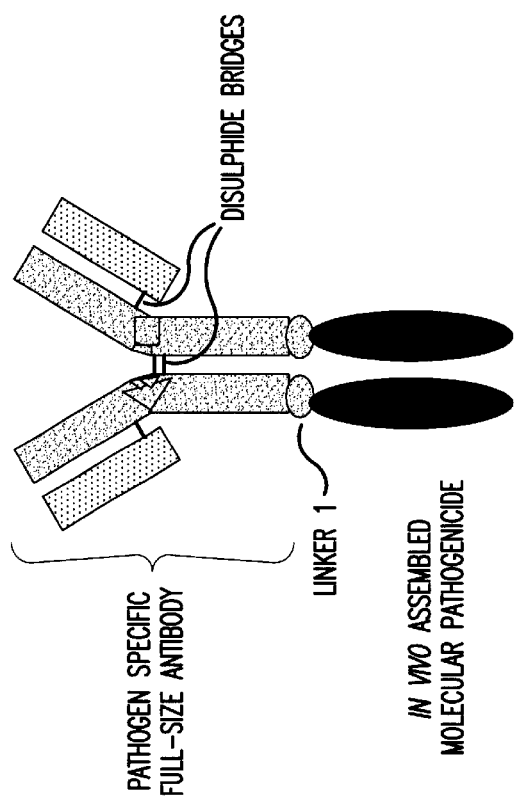
Figure 6B:
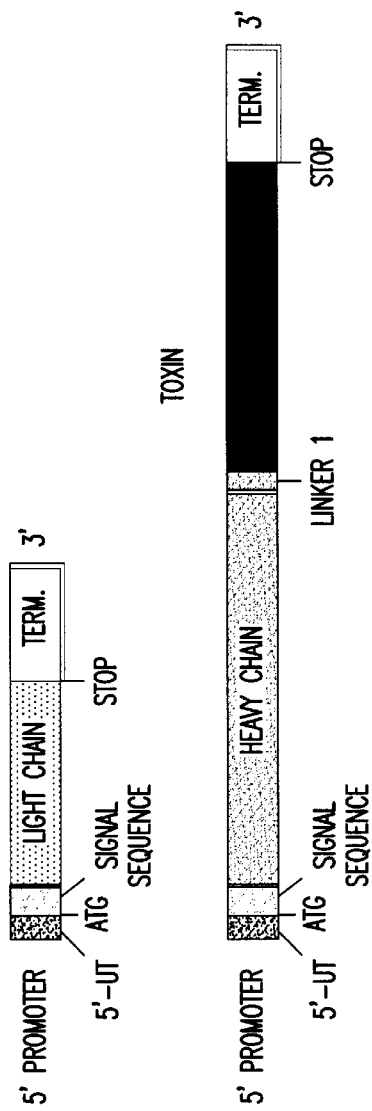

FIG. 6 shows the strategy and example constructs for in vivo molecular pathogenicide assembly using an antibody heavy chain: antibody light chain interaction as the binding partners for in vivo assembly. The two binding partners are an antibody heavy chain and an antibody light chain which specifically recognises this epitope tag. To assemble a molecular pathogenicide protein complex, the epitope specific antibody is genetically fused to a pathogen specific antibody heavy chain C-terminus. Both of these recombinant antibody heavy chain and light chains are then expressed in the same cell compartment, where they assemble via disulphide bridges to give a molecular pathogenicide protein complex, which specifically recognises the pathogen and bears a toxic activity. Linker 1 can encode specific protease cleavage sites or the epitope specific antibody that recognizes an epitope tagged toxin. Also, the toxin can fused to the N-terminus of the antibody heavy chain using linker 1, or the N or C terminus of the light chain. A: schematic of the final assembled molecular pathogenicide. B: example constructs.

Figure 7:
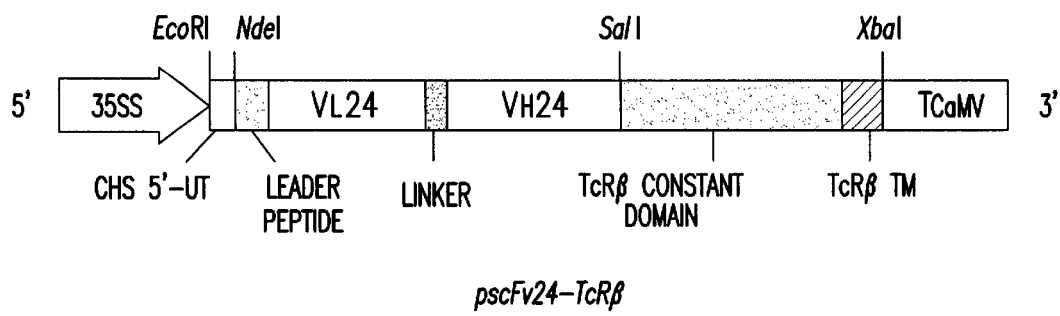

FIG. 7 shows a cDNA construct for targeting and expression of scFv24 on plant cell membranes. CDNAs of mAb24 variable light ($V_L$) and heavy chain ($V_H$) domains connected by a 14 amino acid linker were fused to the human TcRβ transmembrane domain and cloned into EcoRI and XbaI restriction sites of the plant expression vector pSS (33). The DNA sequence of the EcoRI/XbaI fragment from pscFv24-TcRβ is depicted in SEQ ID NO:3. 35SS=double enhanced CaMV-35S promoter; CHS-5'-UT=5' untranslated region of the chalchone synthase; LP=signal sequence of the murine mAb24 light chain; TM=transmembrane domain; TcaMV=CaMV termination sequence.

Figure 8:
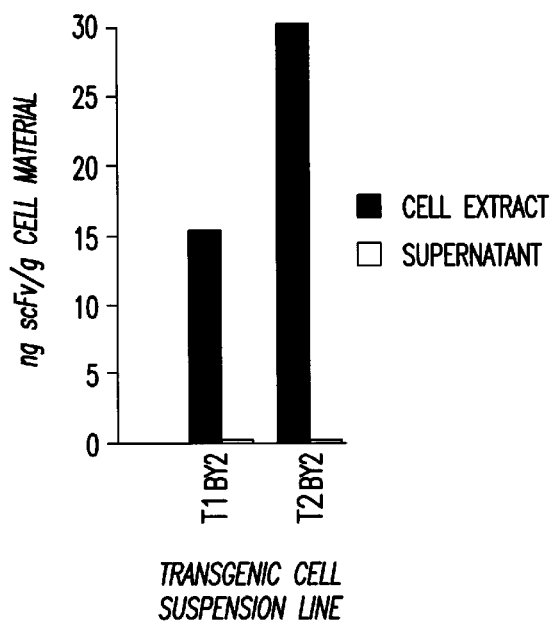

FIG. 8 shows the levels of functional scFv24-TcRβ in transgenic *N. tabacum* cv. BY-2 suspension cell lines. scFv24 production levels in tobacco BY-2 cell extracts and the culture supernatant were analyzed by ELISA using the anti-mAb24 antisera and are indicated as ng scFv24 per g cell material. T1$_{BY-2}$–T2$_{By-2}$=transgenic BY-2 supension cell lines producing scFv24-TcRβ.

Figure 9:
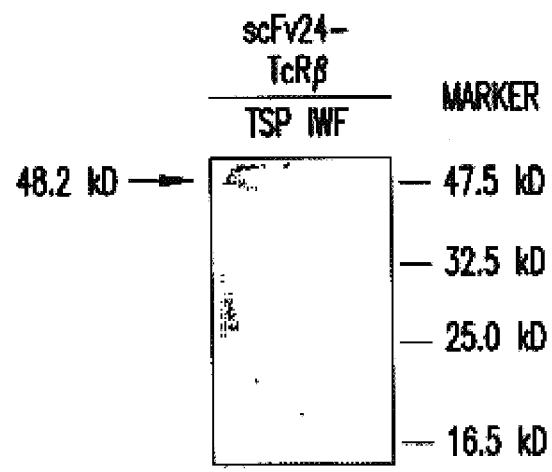

FIG. 9 shows Western blot analysis of a T$_1$ tobacco plant producing scFv24-TcRβ. Equivalent amounts of protein from intercellular washing fluids and total soluble proteins from one T$_1$ plant producing scFv24-TcRβ (lane 1 and 2) were separated on a 12% (w/v) reducing SDS-PAGE gel and transferred to nitrocellulose. Recombinant protein was detected by using a rabbit anti-mAb24 antisera as primary antibody and goat-anti rabbit antibody conjugated to alkaline phosphatase as a secondary antibody and followed by NBT/BCIP staining. Estimated molecular weights of recombinant proteins are indicated (Marker). IWF=intercellular washing fluid; TSP=total soluble protein.

FIG. 10 shows the subcellular localization of membrane anchored scFv24-TcRβ in transgenic N. tabacum cv. BY-2 protoplasts by indirect immunofluorescence. Fixed protoplasts from non-transgenic BY-2 cells (A) and line T2$_{BY-2}$ producing scFv24-TcRβ (B, C, D) were labeled either using anti-mAb24 antisera as a primary antibody followed by a FITC conjugated goat-anti rabbit secondary antibody (A, B, D) or using anti-human TcRβ antibody as a primary antibody, followed by an FITC conjugated goat-anti mouse secondary antibody (C). Magnification=×400.

FIG. 11 shows immunogold localization of scFv24- in transgenic *N. tabacum* cv. Petite Havana SR1 leaves. Ultrathin-sections from plant line $T4_{SR1}$ producing scFv24-TcRβ were probed with rabbit anti-mAb24 antisera primary antibody and 12 nm gold particle conjugated goat-anti rabbit secondary antibody. Arrowheads indicate immunogold labelling of membrane anchored scFv24-TcRβ plant cell plasma and nuclear membrane.

FIG. 12 shows cDNA constructs for targeting and expression of cytosolic scFv24 to plant cell membranes. scFv24 cDNA, comprising variable light chain ($V_L$) and heavy chain ($V_H$) domains connected by a 14 amino acid 212 linker (linker 2), were fused to the C-terminal transmembrane domains using the $Gly_4Ser$ linker (linker 1) and subcloned into the plant expression vector pSS. A) Cytoplasmic targeting vectors containing a C-terminal transmembrane domain. B) Cytoplasmic targeting control vector lacking a transmembrane domain (construction of this vector is described in: Zimmermann et al., 1998). 35SS=enhanced CaMV-35S promoter; CHS 5'UT=5' untranslated region of chalcone synthase; KAR1=transmembrane domain of KAR1 for nuclear membrane integration; mT=transmembrane domain of middleT antigen plasma membrane integration; cytb5=transmembrane domain of cytochrome b5 for ER membrane integration; syn1=transmembrane domain of synaprobrevin1 for membrane integration; His6=histidine 6-tag; c-myc=c-myc-epitope tag; TCaMV=CaMV termination sequence. The DNA sequence of the EcoRI/XbaI fragment from pscFv24-kar1 is depicted in SEQ ID NO: 12. Codon usage of the yeast KAR1 transmembrane domain was adapted to tobacco, wheat and pea; except the TGT (Cys) and CTT (Leu) codons which are rare codons for wheat. The IIe codon ATA (in the transmembrane domain) is also a rare codon for wheat and the Leu codon CTG (in the transmembrane domain) is a rare codon for pea and tobacco, but both codons were necessary to introduce a BsI 107 restriction site. The DNA sequence of the EcoRI/XbaI fragment from pscFv24-mT is shown in SEQ ID NO: 13. Codon usage of the transmembrane domain of murine polymovirus middle-T antigen was adapted to tobacco, wheat and pea. The Ala codon GCG and the Leu codon CTG (both in the transmembrane domain) are rare codons for tobacco and pea, but both were neccessary to introduce a Eco47-3 restriction site. The DNA sequence of the EcoRI/XbaI fragment from pscFv24-cytb5 is shown in SEQ ID NO: 14. Codon usage of rat liver cytochrome b5 transmembrane domain was adapted to tobacco, wheat and pea; except the very C-terminal codon (Asp) which is a rare codon for wheat. The Ala codon GCG (in the transmembrane domain) is also a rare codon for pea and tobacco and the Ile codon ATA (in the transmembrane domain) is a rare codon for wheat, but both codons are necessary to introduce a EcoRV retriction site. The DNA sequence of the EcoRI/XbaI fragment from pscFv24-syn1 is depicted in SEQ ID NO: 15. Codon usage of human synaptobrevin transmembrane domain was adapted to tobacco, wheat and pea; except the last codon (Asp) which is a rare codon for wheat.

FIG. 13 shows a cDNA construct for targeting and expression of scFv24-PE400. scFv24 cDNA, comprising variable light chain ($V_L$) and heavy chain ($V_H$) domains connected by a 14 amino acid 212 linker (linker 2), were fused to the C-terminal Pseudomonas exotoxin domain III using a cellobiohydrolase I (CBH) linker of *Trichoderma reesi* and subcloned into the plant expression vector pSS. 35SS=enhanced CaMV-35S promoter; CHS 5'UT=5' untranslated region of chalcone synthase; LP=signal sequence of the murine mAb24 light chain; linker 1=$Gly_4Ser$ linker; tag54=epitope tag; TCaMV=CaMV termination sequence. The DNA sequence of the EcoRI/XbaI fragment from pscFv24-PE400 is shown in SEQ ID NO: 18.

FIG. 14 (SEQ ID NO: 19) Molecular pathogenocide based on a single chain (scFv24) fusion to *E. coli* RNAse. The two domains of the pathogenocide were connected by a short Gly-Gly-Gly-Ser (SEQ ID NO: 165) linker peptide. This set up can be modified in multiple ways by using different scFv antibodies binding to structural and nonstructural viral target proteins, other RNAase genes or domains thereof fused to either the N- or C-terminus of any selected scFv cDNA.

FIG. 15 shows constructs for expression of scFv24 fusion proteins in the cytoplasm and ER of plant cells. scFv24 cDNA, comprising variable light chain ($V_L$) and heavy chain ($V_H$) domains connected by a 14 amino acid 212 linker (linker 2), were fused to CP using the $(Gly_4Ser)_2$ linker (linker 1) and subcloned into the plant expression vector pSS. A) Cytoplasmic targeting vectors containing a C-terminal His6 or KDEL sequence. B) Cytoplasmic targeting control, vectors lacking a fusion partner. C) ER retention vector. D) Apoplastic targeting vector (the fusion protein is secreted to the apoplast and will enter the cell by binding to invading TMV virions). 35SS=enhanced CaMV-35S promoter; •=5' untranslated region of TMV; LP=codon optimized original mouse leader peptide sequence from mAb24; CP=fusion partner TMV coat protein; His6=histidine 6-tag; KDEL=ER retention signal; Pw=TMV 3' untranslated region. The DNA sequence of the EcoRI/XbaI fragment from CP-scFv24H is shown in SEQ ID NO: 24. The DNA sequence of the EcoRI/XbaI fragment from CP-scFv24K is shown in SEQ ID NO: 25. The DNA sequence of the EcoRI/XbaI fragment from scFv24H is shown in SEQ ID NO: 26. The DNA sequence of the EcoRI/XbaI fragment from scFv24K is shown in SEQ ID NO: 27. The DNA sequence of the EcoRI/XbaI fragment from L-CP-scFv24K is shown in SEQ ID NO: 28.

FIG. 16 shows protein levels of ER retained scFv- fusion proteins. *N. tabacum* cv. Petite Havana SR1 leaves were transiently transformed with recombinant agrobacteria containing the construct L-CP-scFv24K and incubated for three days. Total soluble protein was isolated and levels of functional scFv24-fusion protein, was quantified in a TMV-specific ELISA and indicated as ng per gram leaf material. The column represents the mean value of four leaves. Standard deviations are indicated.

FIG. 17 shows Western blot analysis of ER retained fusion proteins. Affinity purified L-CP-scFv24K was separated by 12% SDS-PAGE and proteins were transferred to a nitrocellulose membrane. Blots were probed with CP-specific mAb29 primary antibody followed by alkaline phosphatase conjugated goat-anti rabbit and goat-anti mouse secondary antibody and NBT/BCIP staining. Lane 1: Prestained protein marker; lane 2: TMV-affinity purified L-CP-scFv24K.

FIG. 18 shows levels of cytoplasmic expressed fusion proteins. N. benthamiana leaves were transiently transformed with recombinant agrobacteria and incubated for three days. Total soluble protein was isolated and levels of functional scFv24, expressed as part of the fusion proteins, were quantitated in a TMV-specific ELISA and indicated as ng per gram leaf material. Each column represents the mean value of four leaves and demonstrates the protein levels of constructs CP-scFv24H and scFv24H containing a C-terminal His6 sequence and protein levels of constructs CP-scFv24K and scFv24K containing a C-terminal KDEL sequence. Standard deviations are indicated with bars.

Figure 19:
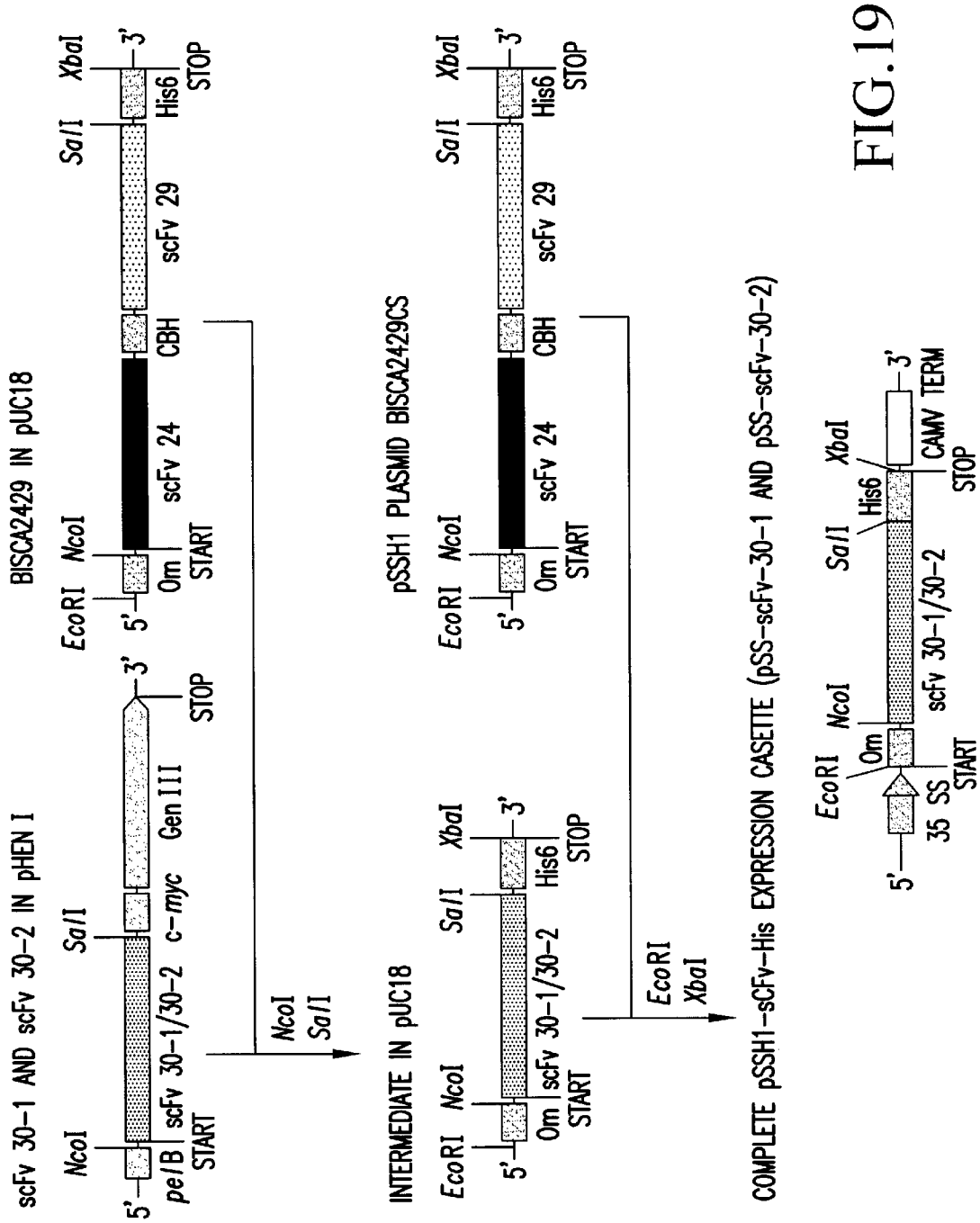

FIG. 19 shows the cloning of TMV 30K movement protein specific antibodies into the plant expression vector pSSH1. Single chain fragments obtained by phage display were subcloned into the BISCA2429 expression cassette (Fischer et al., (1999) Eur. J. Biochem. 262, 810–816) using NcoI/ SalI restriction sites. Resulting temporary constructs (5'-UTR of TMV omega sequence, scFv, His6 tag) were subcloned into the plant expression vector pSSH1 using EcoRI/ XbaI subcloning assembling the final vector for plant transformation and expression (35 SS promoter, 5'-UTR of TMV omega sequence, scFv, His6 tag, 3'-UTR and Terminator of CaMV) of the anti 30K scFv.

FIG. 20 shows the reactivity in ELISA of 10 different 30K-specific scFv antibodies against GST-30K (biotinylated and non biotinylated) and GST (A) and Reactivity in ELISA of the same 10 scFv fragments against five different Domains of the 30K movement protein expressed as GST-fusion proteins (B). The 30K-specific scFvs were selected from a phage library derived from GST-30K immunized mice.

FIG. 21 shows the amino acid residues of two selected scFv binding to the 30K movement protein of TMV obtained by phage display using GST-30K immunized mice for PCR-based amplification of $V_H$- and $V_L$-fragments. ScFv 30-1 (SEQ ID NO: 29)=30K specific scFv No.1, scFv 30-2 (SEQ ID NO:30) specific scFv No. 2. Amino acid residues were derived from cDNA-sequencing of the respective phage derived scFv-cDNA clones as described (FIG. 19).

Figure 22:
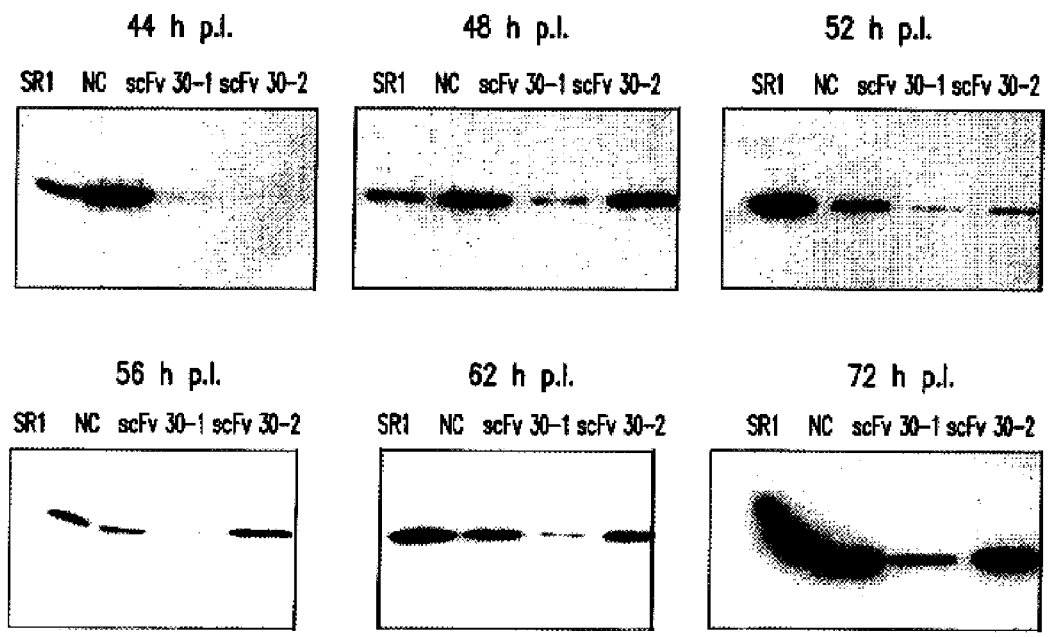

FIG. 22 shows the time course (44 h, 48 h, 52 h, 56 h, 62 h and 72 h post inoculation, p.i.) for monitoring the accumulation of coat protein in transgenic and non-transgenic anti-30K scFv expressing plants detected by western blotting using a TMV coat protein specific antibody (mAb 24) upon inoculation with TMV vulgare. SR1=SR1 wild-type plants, NC=negative control (Transgenic SR1 expressing the antitumor scFv T84.66).

FIG. 23 shows amino acid sequences derived from the cDNA sequences of antiviral scFv-antibodies obtained by hybridoma rescue (FIG. 24) directed against the 3a movement protein of CMV (SEQ ID NO: 113) (23a), a component of the TMV replicase (SEQ ID NO: 114) 23b, 54K of TMV) and a plant virus minimal protein (SEQ ID NO: 115) (23c, 3 min of PLRV).

Figure 24:
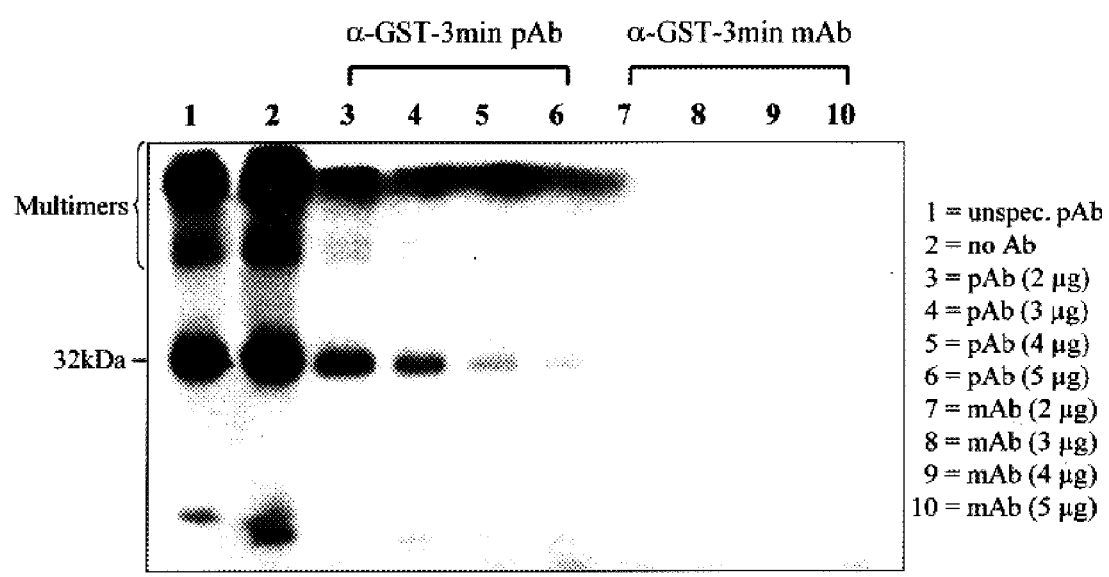

FIG. 24 shows binding competition between antibodies and PLRV ssRNA. 100 ng of the GST-3 min protein were incubated for 30 min at RT with either indicated amounts of polyclonal anti-3 min antibodies (pAb, lanes 3, 4, 5 and 6), anti-3 min antibody (mAb, lanes 7, 8, 9 and 10) and polyclonal anti-GST antibodies (lane 7) or without antibody (lane 2). The complexes were mixed with 0.5 ng of radioactively labeled ssRNA probe, incubated for 25 min at 4° C. and irradiated with UV light at RT. After digestion of unprotected RNA by RNase A, the complexes were analysed by 15% SDS-PAGE and the dried gel was autoradiographed.

FIG. 25: Epitope mapping of three different antiviral antibodies namely (a) mAb 29 (see Example 1), (b) scFv 54-1 (Example 6, FIG. 23b, FIG. 29) and (c) scFv 3a-2 (Example 6, FIG. 23a). Sequences were obtained from phage ELISA positive clones after the third round of biopanning using two peptide display libraries (Cortese et al. (1995) Curr. Opin. Biotechnol. 6, 73–80). Resulting sequences (SEQ ID NOS: 116–156) were aligned and the consensus epitope was determined. In each case the epitope could be mapped within the parental sequence of the different viral sequences analysed.

FIG. 25a: Epitope mapping and consensus-sequence of mAb 29 using peptide display and two different peptide display libraries (9 mer random library (pVIII 9aa) and 9 mer (9aa.Cys) constrained library). From the 9 mer random library 10 different positive clones could be characterized and sequenced, from the 9 mer constrained library 5 positive clones were characterized. Both libraries resulted in the identification of the same epitope based on a consensus sequence which could be mapped within the TMV-coatprotein sequence.

FIG. 25b: Epitope mapping and consensus-sequence of scFv 54-1 using peptid display (9 mer linear library). From the 9 mer linear library 4 different positive clones could be characterized and sequenced, resulting in the identification of the same scFv epitope based on a consensus sequence which could be mapped within the 54K protein sequence.

FIG. 25c: Epitope mapping and consensus-sequence of scFv 3 min using peptide display and two different peptide display libraries (9 mer random library (pVIII 9aa) and 9 mer (9aa.Cys). From the 9 mer random library 8 different positive clones could be characterized and sequenced, from the 9 mer constrained library 7 positive clones were characterized. Both libraries resulted in the identification of the same epitope based on a consensus sequence which could be mapped within the border region of GST-3 min.

FIG. 26 shows a cDNA construct for studying assembly of recombinant proteins. Constructs for expression of biscFv2429, PE280-tag29 and PE400-tag29 in the apoplast of plant cells and GST-tag29 in bacteria.

A) scFv cDNAs, composed of mAb24 and mAb29, variable light chain ($V_L$) and heavy chain ($V_H$) domains connected by a 14 amino acid 212 linker (linker 2), were fused using the CBHI-linker. biscFv2429 was subcloned into the plant expression vector pSS. B) PE280 composed of PE domain II (aa 280–364) and domain III (aa 381–609) was fused to the epitag-29 via a Gly$_4$Ser linker (linker 1). PE280-tag29 was subcloned into the plant expression vector pSS. C) PE400 composed of PE domain III (aa 381–609) was fused to the epitag-29 via a Gly$_4$Ser linker (linker 1). PE400-tag29 was subcloned into the plant expression vector pSS. D) The epitag-29 was fused to the C-terminus of GST via a Gly$_4$Ser linker (linker 1) in the pGEX-5X-3 vector. The DNA sequence of the EcoRI/XbaI fragment from PE280-tag29 is shown in SEQ ID NO: 161. The DNA sequence of the EcoRI/XbaI fragment from PE400-tag29 is shown in SEQ ID NO: 162.

35SS=double enhanced CaMV-35S promoter; Ptac=tac promoter; CHS-5'-UT=5' untranslated region of the chalcone synthase; LP=leader peptide of the murine monoclonal antibody mAb24 light chain; GST=glutathione S-tranferase; his6=histidine6 tag; tag29=epitag-29; TCaMV=CaMV termination sequence.

FIG. 27 shows the detection of GST-tag29 by immunoblot. Serial dilutions of bacterial produced and affinity purified GST-tag29 in PBS (A) or protein extract of *N. tabacum* cv. Petite Havana SR1 (B) were separated on a 12% (w/v) reducing SDS-PAA gel and transferred to nitrocellulose. Recombinant protein was detected by using rAb29 and goat-anti mouse antibody conjugated to alkaline phosphatase as a secondary antibody and followed by NBT/BCIP staining. Amounts of GST-tag29 loaded and molecular weights of the prestained protein marker are indicated.

Figure 28:
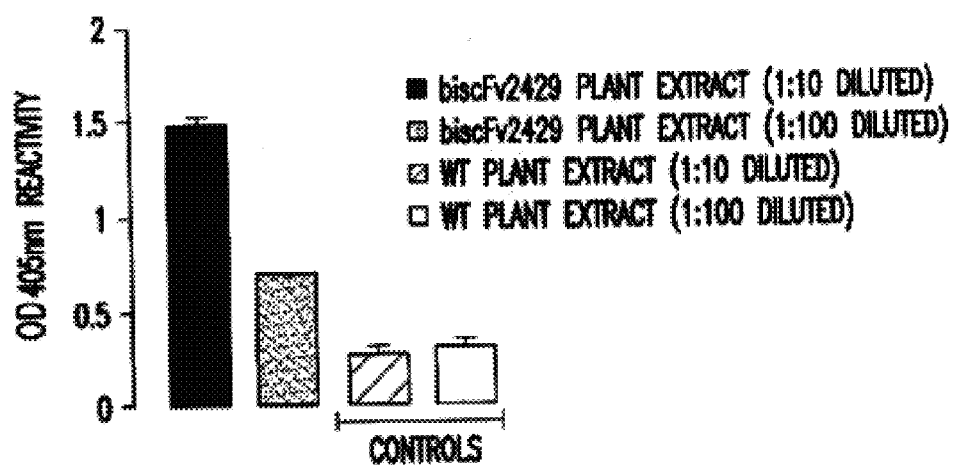

FIG. 28 shows simulation of in vivo assembly by ELISA. Assembly of biscFv2429 from transgenic plants and GST-tag29 produced in bacteria followed by affinity purification was analysed by ELISA. The components were added in the following order to the microtiter plate: Polyclonal TMV rabbit-anti TMV antibodies (7 μg/ml), 1% BSA for blocking, TMV virions (1 μg/ml), plant extracts from a transgenic plant producing biscFv2429 (diluted 1:10 or 1:100), bacterially expressed GST-tag29, mouse anti-GST mAb (1 μg/ml), 1:5000 diluted alkaline phosphatase labelled goat anti-mouse Fc antibody and substrate. Controls were performed using extracts from a non-transgenic tobacco plant. The levels of in vivo assembly are indicated as OD 405 nm. Each column represents the mean value of two independent ELISA experiments. Standard deviations are indicated with bars.

Figure 29:
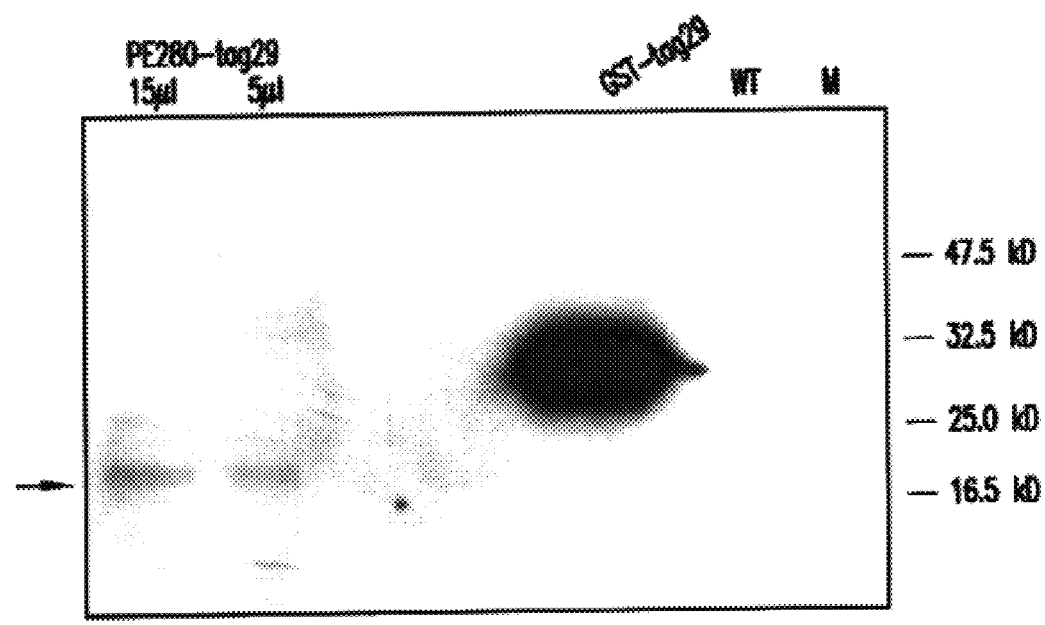

FIG. 29 shows immunoblot of PE280-tag29 transient transformed tobacco leaves. Tobacco leaves transformed using recombinant agrobacteria were incubated for 72 h and protein extract was isolated. 15 μl and 5 μl of total soluble proteins from tobacco leaves producing PE280-tag29, 10 μl of a non-transgenic plant (WT) and 400 ng affinity purified GST-tag29 as control were separated on a 12% (w/v) reducing SDS-PAGE gel and transferred to nitrocellulose. Recombinant protein was detected by using a mouse anti-GST mAb as primary antibody and goat-anti mouse antibody conjugated to horseradish peroxidase as a secondary antibody, followed by chemiluminescence detection. The arrow indicates the position of the degraded PE280-tag29 band. Molecular weights of a prestained marker are indicated.

Figure 30:
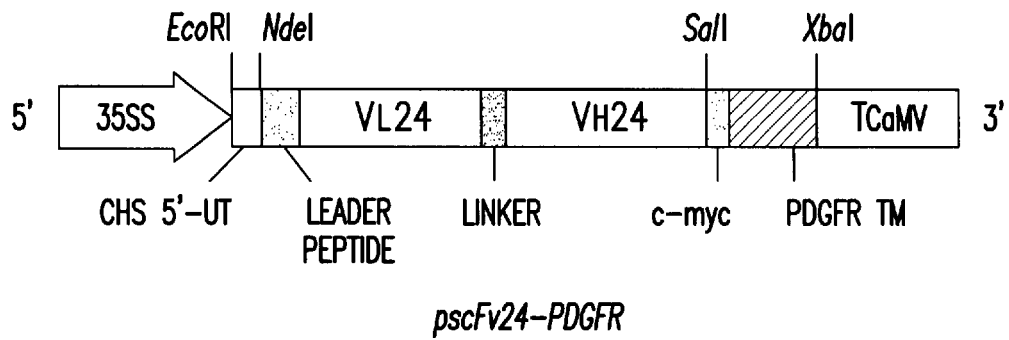

FIG. 30 shows a cDNA construct for targeting and expression of scFv24 on plant cell membranes. cDNAs of mAb24 variable light ($V_L$) and heavy chain ($V_H$) domains connected by a 14 Genex-212 amino acid linker (36) were fused to the PDGFR and cloned into EcoRI and XbaI restriction sites of the plant expression vector pSS (33). 35SS=double enhanced CaMV-35S promoter; CHS-5'-UT=5' untranslated region of the chalcone synthase; c-myc=c-myc-epitope tag; TM=transmembrane domain; TCaMV=CaMV termination sequence. The DNA sequence of the EcoRI/XbaI fragment from pscFv24-PDGFR is depicted in SEQ ID NO: 163.

Figure 31:
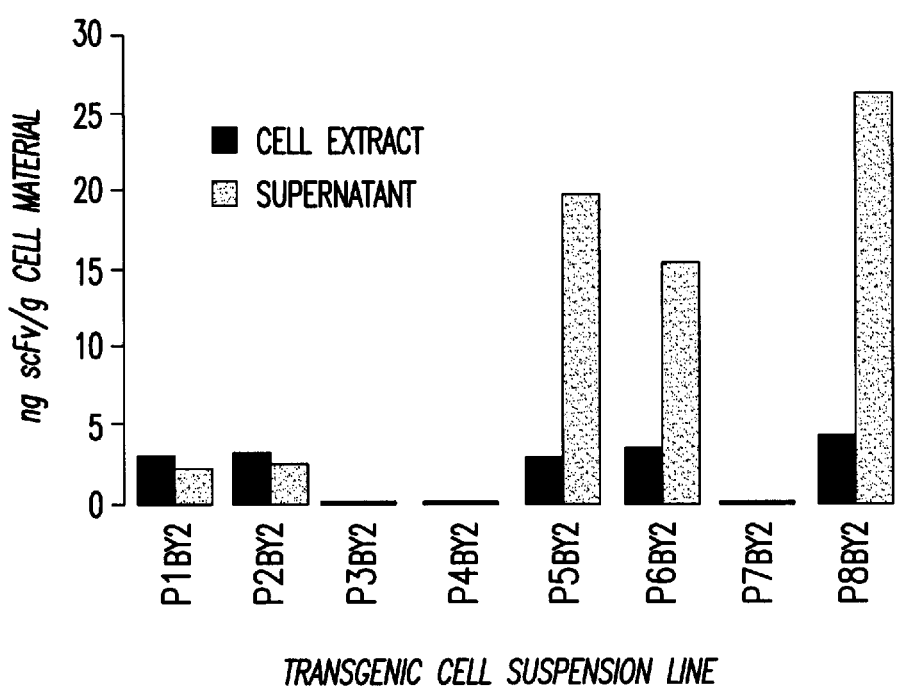

FIG. 31 shows the levels of functional scFv24-PDGFR in transgenic *N. tabacum* cv. BY-2 suspension cell lines. scFv24 production levels in tobacco BY-2 cell extracts and the culture supernatant were analyzed by ELISA using the anti-mAb24 antisera and are indicated as ng scFv24 per g cell material. $P1_{BY-2}$–$P8_{BY-2}$=transgenic BY-2 suspension cell lines producing scFv24-PDGFR.

FIG. 32 shows Western blot analysis of $T_1$ tobacco plants producing scFv24-PDGFR. Equivalent amounts of protein from intercellular washing fluids and total soluble proteins from three $T_1$ plants producing scFv24-PDGFR were separated on a 12% (w/v) reducing SDS-PAGE gel and transferred to nitrocellulose. Recombinant protein was detected by using a rabbit anti-mAb24 antisera as primary antibody and goat-anti rabbit antibody conjugated to alkaline phosphatase as a secondary antibody (A) or using a murine anti-c-myc antibody as primary antibody and goat-anti mouse antibody conjugated to alkaline phosphatase as secondary antibody (B) and followed by NBT/BCIP staining. Estimated molecular weights of recombinant proteins are indicated (marker). IWF=intercellular washing fluid; TSP=total soluble protein.

EXAMPLES

The following examples are given to better describe the practice and applications of the present invention and should not be considered to be a limiting description nor interpreted to limit the scope and applications of the present invention. Those skilled in the art will recognise that various modifications can be made to the methods and genes described here without substantively departing from the spirit and scope of the present invention.

Example 1

Expression of a Membrane Integrated Anti-viral Antibody

Plasma Membrane Targeted Expression of a Recombinant Antibody Against the Coat Protein of Tobacco Mosaic Virus (TMV)

The following steps are taken:
1) Antibodies against the coat protein of TMV, intact virions or specific coat protein peptides and monoclonals are generated by hybridoma technology.
2) Hybridoma cell lines are cloned and cDNA sequences encoding the antibody heavy and light chains are cloned to generate a recombinant antibody or any recombinant version thereof. This is achieved using antibody heavy and light specific oligonucleotides and the reverse transcriptase polymerase chain reaction using isolated mRNA from a single hybridoma clone. This permits cloning of the full size antibody.
3) The cloned full size specific antibody heavy and light chain cDNAs from step 2 are used as a template for amplification of the heavy and light chain variable domains using specific oligonucleotide primers including a linker peptide sequence (i.e. GENEX 212 or $(Gly_4Ser)_n$) and splice overlap extension polymerase chain reaction. This step then provides the single chain antibody fragment and the two variable domains are linked by a 14 amino acid sequence.
4) The recombinant scFv gene from step 3 is inserted in a microbial or eukaryotic expression vector.
5) The binding specificity and function of the recombinant scFv (i.e. specificity and affinity for the target antigen) is checked after expression of the construct from step 4 in a heterologous host, such as in the periplasm of *E. coli*, using ELISA, surface plasmon resonance or western blotting.
6) A signal sequence is added to the 5' end of the recombinant scFv nucleotide sequence from step 3. A 3' linker peptide sequence (human T cell receptor constant domain) is added and this is then followed by the addition of a 3' transmembrane sequence from the human T cell receptor β chain. Suitable membrane localisation sequences also include the platelet derived growth factor receptor (PDGFR) transmembrane domain.

7) The 5' untranslated region from chalcone synthase is added to the 5' end of the construct from step 6.
8) The chimeric gene from step 7 is then inserted into a plant expression vector, such as pSS (Voss et al., 1995), upstream of the 3' untranslated region from Cauliflower mosaic virus, or any other source and the termination region from Cauliflower mosaic virus downstream of the 35SS promoter (FIG. 2). This H-vector also contains a selectable marker. In case of markerless and vectorless gene transfer selection marker sequences can be omitted.
9) *Agrobacterium tumefaciens* is transformed by $N_2$ transformation with the construct from step 8.
10) Expression and function of the recombinant scfv construct in plants are checked by transient expression in plant cells and ELISA, surface plasmon resonance or western blotting.
11) Transgenic plants are generated by transferring the construct from step 8, and a screenable selection marker, which is present in the pSS expression vector (e.g. the NPT-II gene for kanamycin resistance), into the plant genome by Agrobacteria mediated transformation.
12) Regenerated plants are screened using the selection marker for integration of the fusion gene.
13) Expression of the fusion protein in regenerated plants is followed by western blotting cell extracts, ELISA or surface plasmon resonance analysis.
14) The activity of the expressed fusion protein (i.e. affinity and specificity) is checked by ELISA using intact TMV virions as the antigen.
15) Localisation of the fusion protein is checked by indirect immuno-fluorescence, or confocal microscopy or immuno-electron microscopy.
16) The activity of the antibody in generating resistance against viruses is assayed by viral infection bioassays on transgenic plants, generated in steps 11 to 12 by using virions or infectious transcripts.

The orientation of Type II or tetraspan membrane protein can be exploited to permit display of molecular pathogenicdes to the cytoplasm after their synthesis in the secretory pathway. For cytoplasmic display of the recombinant scFv, steps 6) to 16) of example 1 are repeated with the following adaptations, The C-terminal membrane localisation sequence including the linker sequence and leader sequence of step 6 in example 1 are removed and a suitable linker and N-terminal targeting sequence belonging to the tetraspan family is added to the pathogen specific recombinant antibody to target and posttranslationally integrate recombinant proteins into the bilayer of plasma membranes. Suitable members of the tetraspan family include CD9, CD20, CD81 and the In-Hc-Ic dualspan typeII-IV hybrid of the MHC invariant chain and H-$2^d$ hybrid protein. This method enables the orientation of a secreted and membrane anchored antibody construct with its N- and C-terminus into the cytosol.

Anyone of skill in the art will recognise that these steps can be followed for any other pathogen by selecting antibodies or fragments thereof specific for the target pathogen. For example, antibodies can be raised and cloned against structural and non structural proteins of any pathogen. Membrane anchor sequence(s) can be substituted against any sequence that facilitates membranes integration and provides a biological function. Moreover, example 1 can be combined with expression of any one of examples 2–8 in any combination(s) to give high level resistance to disease.

Construction of the scFv24 Fusion Expression Cassette

To integrate the TMV-specific scFv24 into the plant cell membrane, the antibody fragment was fused to an N-terminal mammalian signal peptide and C-terminal receptor transmembrane domain. The mouse N-terminal light chain signal peptide from the parental antibody (mAb24) used to generate scFv24 was used to target fusion proteins to the secretory pathway. The transmembrane domain sequence of the human T-cell receptor β chain (TcRβ) was selected for fusion with the C-terminus of scFv24, for heterologous targeting of the scFv24 antibody to the plasma membrane. To ensure proper folding of the expressed single chain antibody fragments, the construct contained the constant region of TcRβ (pscFv24-TcRβ) as a linker sequence between the scFv24 fragment and the membrane anchor (FIG. 7). The cloning of the neotope-specific anti-tobacco mosaic virus (anti-TMV) single-chain fragment scFv24CM including the leader peptide has been described (Zimmermann et al. 1998). To generate the fusion construct pscFv24-TcRβ (FIGS. 2 and 7), a cDNA fragment encoding the constant and transmembrane domain of the human TcRβ chain (Yoshikai et al. Nature 312: 521–524 (1984)) was PCR amplified from human spleen mRNA (Clontech, Heidelberg, Germany) using the primers 5'-GCC GTC GAC GAG GAC CTG MC AAG GTG TTC CCA-3' (SEQ ID NO:1) and 5'-GCC TCT AGA TCA GAA ATC CTT TCT CTT G-3' (SEQ ID NO:2). The primers contained restriction sites SalI and XbaI (italics) to enable in frame cloning of the PCR product with scFv24CM (Zimmermann et al. 1998) resulting in the final construct scFv24-TcRβ.

For expression in plant cells, the EcoRI/XbaI fragment (FIG. 7) of scFv24-TcRβ was subcloned into the EcoRI and XbaI restriction sites of the plant expression vector pSS (Voss et al. (1995)) containing the enhanced 35S promoter (Kay et al. (1987)) and the CaMV termination sequence (FIG. 7, pscFv24-TcRβ).

Expression of the scFv24 Fusion Proteins in *N. tabacum* cv. BY-2 Cell Suspensions To analyze the expression level of the recombinant scFv-fusion protein, the suspension cell line *N. tabacum* cv. BY-2 was stably transformed with recombinant *A. tumefaciens* and functional expression of the scFv24 domain of the fusion protein was analyzed by ELISA using anti-mAb24 antisera.

The vector construct pscFv24-TcRβ was transferred into *A. tumefaciens* GV3101 by liquid $N_2$ transformation (Höfgen and Willmitzer, Nucleic Acids Res. 16: 9877 (1988)). *N. tabacum* L. cv. bright yellow 2 (BY-2) cells were maintained in Murashige and Skoog basal salt with minimal organics (MSMO+: MSMO (Sigma, Deisenhofen, Germany) plus 200 mg/ml $KH_2PO_4$, 0.6 μg/ml thiamine, 3% sucrose and 0.2 μg/ml 2,4-D, pH 5.8) at 24° C. in the dark on an orbital shaker. Cells were subcultured every week with a 5% inoculum. Three days after subculture, plant cells were transformed by co-cultivation with recombinant *A. tumefaciens*, as described (An, Plant Physiol. 79: 568–570 (1985)). Selection of kanamycin-resistant transformants was performed on MSMO+ agar medium supplemented with 75 μg/ml kanamycin and 100 μg/ml claforan.

For extraction of total soluble proteins from transgenic BY-2 suspension culture, cells from 1 ml culture were collected by centrifugation at 4000×g for 5 min at 4° C. The cell pellet was resuspended in 1 ml protein extraction buffer (200 mM Tris-HCl (pH 7.5), 5 mM EDTA, 0.02% (w/v) sodium-azide and 0.1% (v/v) Tween 20) and cells were disrupted by sonication at 60 watt for 1 min using a sonicator probe (B. Braun, Melsungen, Germany) at 4° C. Cell debris was removed by centrifugation at 14000×g for 10 min at 4° C. The clear supernatant containing soluble protein was used for further analysis.

For ELISA and western blotting, anti-mAb24 antisera (Zimmermann et al. (1998)) was used as a primary antibody in combination with a 1:5000 dilution of goat anti-rabbit alkaline phosphatase conjugated secondary antibodies (Jackson Immuno Research Laboratories, West Grove, Pa.). Protein concentrations were determined with the Bio-Rad Protein Assay using Bovine Serum Albumin (BSA) as standard. Analysis of stably transformed N. tabacum BY-2 cells revealed that scFv24-TcRβ was completely intracellular (FIG. 8). scFv24-TcRβ was not detectable in the culture supernatant, indicating that the TcRβ transmembrane domain is stable and suitable for targeting scFv24 to tobacco cell membranes.

Characterization of Transgenic Plants

It was then tested whether the heterologous mammalian transmembrane domain TCRβ fused to scFv24 would target the single chain antibody to the plasma membrane in stably transformed tobacco plants. Transgenic N. tabacum cv. Petite Havana SR1 were generated by the leaf disc transformation with recombinant A. tumefaciens and transgenic $T_0$ plants were generated from transformed callus (Horsch et al., Science 227: 1229–1231 (1985)). Extraction of total soluble proteins from tobacco leaves and subsequent analysis of scFv24 by ELISA were performed as described by Fischer et al. [Fischer R, Drossard J, Liao Y C, Schillberg S: Characterisation and applications, of plant-derived recombinant antibodies. In: Cunningham C, Porter A J R (eds), Recombinant proteins in plants: Production and Isolation of Clinically useful compounds, pp. 45–68. Vol. 3. Humana press, Totowa, N.J. (1998)]. For ELISA and western blotting, anti-mAb24 antisera (Zimmermann et al. (1998)) was used as a primary antibody in combination with a 1:5000 dilution of goat anti-rabbit alkaline phosphatase conjugated secondary antibodies (Jackson Immuno Research Laboratories, West Grove, Pa.). Protein concentrations were determined with the Bio-Rad Protein Assay using Bovine Serum Albumin (BSA) as standard. Expression levels of scFv24-TcRβ were much higher in transgenic N. tabacum cv. Petite Havana SR1 plants than in suspension cultures (Table 1). The maximum level of detergent extracted scFv24-TcRβ was 296 fold higher (8866 ng/g leaf tissue) than that obtained in transgenic suspension cultures (FIG. 8).

To determine if the scFv24 fragment was stably integrated into the plasma membrane or secreted into the extracellular space of intact plants, intercellular washing fluid from leaves of transgenic $T_1$ tobacco plants was analyzed by ELISA. For detection of scFv24 fusion protein in intercellular washing fluids, leaves of N. tabacum cv. Petite Havana SR1 were prepared as described by Fischer et al. (Fischer: Characterisation and applications of plant-derived recombinant antibodies. In: Cunningham C, Porter A J R (eds), Recombinant proteins in plants: Production and Isolation of Clinically useful compounds, pp. 45–68. Vol. 3. Humana press, Totowa, N.J. (1998)). Total protein extracts from washing fluids were concentrated by ultrafiltration (Microcon 10, Amicon, Witten, Germany) and analyzed by 12% SDS-PAGE (Laemmli, Nature 227: 680–685 (1970)) followed by western blot. There was no detectable antibody in the intercellular washing fluid from ten $T_1$ progenies of two plant lines ($T4_{SR1}$ and $T6_{SR1}$) producing the scFv24-TcRβ fusion protein. In general, $T_1$ plants used for IWF analysis showed high expression levels of intracellular scFv24-TcRβ (1570–8940 ng/g leaf tissue).

Western blot analysis of total soluble protein isolated from a $T_1$ progeny of plant line $T4_{SR1}$ showed only the predicted full length 48.2 kDa scFv24-TcRβ fusion protein and neither the intact fusion protein nor any degradation products were detectable in the intercellular washing fluid (FIG. 9). This demonstrates that scFv24-TcRβ was not secreted and remained membrane anchored in transgenic plants.

Subcellular Localization of scFv24-TcR1 in Transoenic N. tabacum cv. BY-2 Protolasts Since the scFv24-TcRβ construct contains signal peptide and transmembrane sequences, fusion protein should be localised at the plasma membrane. To determine the subcellular localization of the scFv24-fusion protein, transgenic N. tabacum cv. BY-2 protoplasts were generated and analysed by immunofluorescence microscopy (FIG. 10).

Protoplasts were prepared by digesting 3 day old tobacco BY-2 cells with 1.5% (w/v) cellulase Onozuka RS (Yakult Honsha Co., Tokyo, Japan), 0.7% (w/v) hemicellulase (Sigma) and 0.1% (w/v) pectolyase Y23 (Seishin Pharmaceuticals, Nihonbashi, Tokyo, Japan) in MES buffer (0.5% (w/v) MES, 80 mM $CaCl_2$, 0.3 M mannitol, pH 5.8) for 1.5 h at 25° C. on a rotary shaker. Protoplasts were washed with MES buffer, transferred to fresh MSMO+ medium and incubated over night at 24° C. on an orbital shaker in the dark. Regenerating protoplasts were washed once with MES buffer and settled on poly-L-lysine-coated multiwell slides. Cells were fixed for 15 min at room temperature with 4% (w/v) formaldehyde in MTS buffer (50 mM Pipes, 5 mM EGTA, 5 mM $Mg_2SO_4$, pH 6.9) plus 0.3 M mannitol. The resulting protoplast ghosts were washed with MTS buffer and incubated for 1 h at room temperature with a 1:2500 dilution of rabbit anti-mAb24 antisera (Zimmermann et al. (1998)) or a 1:50 dilution of mouse anti-human TcRβ IgG (T Cell Diagnostics, Woburn, Mass.) in 3% (w/v) BSA MTS buffer supplemented with 0.3 M mannitol. Cells were washed with MTS buffer and then incubated for 1 h at room temperature with FITC-conjugated goat anti-rabbit or FITC-conjugated goat anti-mouse secondary antibodies (Jackson Immuno Research Laboratories) diluted 1:100 in 3% (w/v) BSA MTS buffer supplemented with 0.3 M mannitol. After washing with MTS buffer, slides were mounted in Citifluor antifade (Citifluor Ltd., London, England) and imaged on a Zeiss inverted microscope equipped with a 40× oil-immersion objective using 450–490 nm excitation and 520–560 nm emission interference filters. Images were recorded on T-max 400pro film (Kodak, Rochester, N.Y.).

Figure 10A:
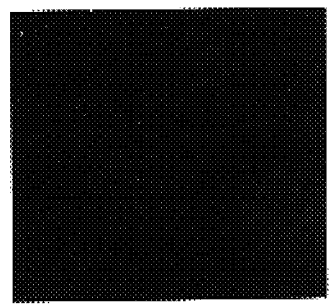
Figure 10B:
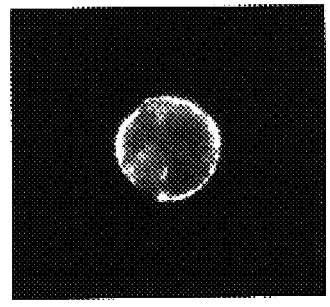
Figure 10C:
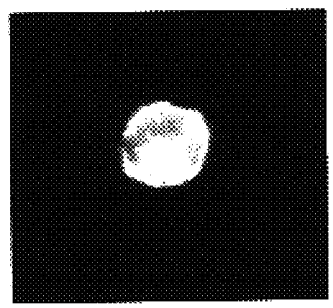
Figure 10D:
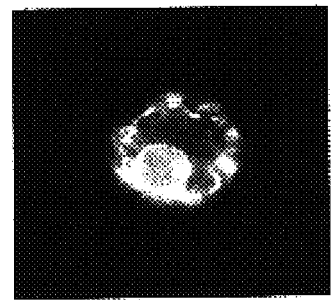

Protoplasting enzymes contain proteases which degrade cell surface proteins and there was no detectable cell surface staining directly after protoplasting BY-2 cells. However, overnight regeneration of protoplasts allowed delivery of newly synthesized membrane bound scFv24 to the cell surface and gave optimal staining. Control wild type N. tabacum cv. BY-2 cells showed no evidence of surface staining (FIG. 10A). In contrast, protoplasts derived from the transgenic N. tabacum cv. BY-2 suspension cell line $T2_{BY-2}$ producing scFv24-TcRβ were brightly stained with anti-Ab24 sera at the plasma membrane, demonstrating the plasma membrane localization of the scFv24-TcRβ fusion protein (FIG. 10B). In addition, the localisation of scFv24-TcRβto the plasma membrane was also observed by staining with the anti-human TcRβ antibody, which recognizes the constant region of TcRβ that links the TcRβ transmembrane domain to scFv24 (FIG. 10C). In addition to plasma membrane labeling, some protoplasts showed nuclear membrane staining for the scFv24-TcRβ fusion protein (FIG. 10D).

Immuno-electron Microscopy

Immuno-electron microscopy was performed on ultrathin section of leaves, to verify location of membrane bound scFv24.

Small tissue pieces of transgenic N. tabacum cv. Petite Havana SR1 plants were embedded at low temperature for immunogold labeling (Wells, Micron and Microscopica Acta 16: 49–53 (1985)). Immunogold labeling of thin sections on plastic-filmed gold grids was carried out as previously described (McCann et al. J. Microsc. 166: 123–136 (1992)), except that blocking buffer used for the incubations with antibodies contained 3% (w/v) BSA. Primary antibodies: rabbit anti-mAb24 antiserum at 1:100 dilution (Zimmermann et al. (1998)) or mouse anti-human TcRβ IgG at 1:25 dilution (T Cell Diagnostics), were incubated with sections for 1 h. Secondary antibodies were 12 nm gold conjugated goat anti-rabbit or 12 nm gold conjugated goat anti-mouse (Jackson Immuno Research Laboratories) and were incubated with sections at a dilution of 1:40 for 1 h. Bright-field light micrographs of 1 μm thick resin sections were viewed at 80 kV on a Joel 1200EX transmission electron microscope, and photographs were taken using Kodak film.

Figure 11:
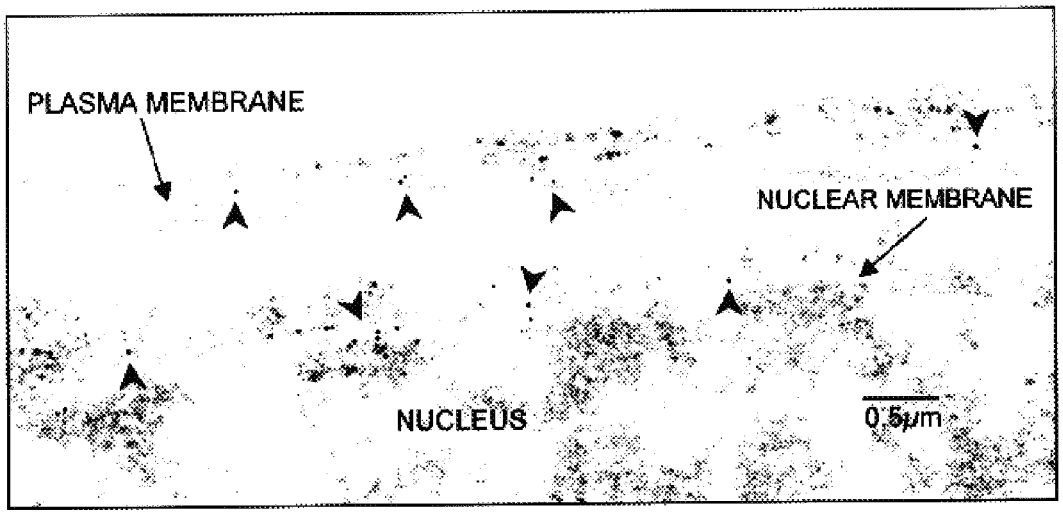
Figure 12A:
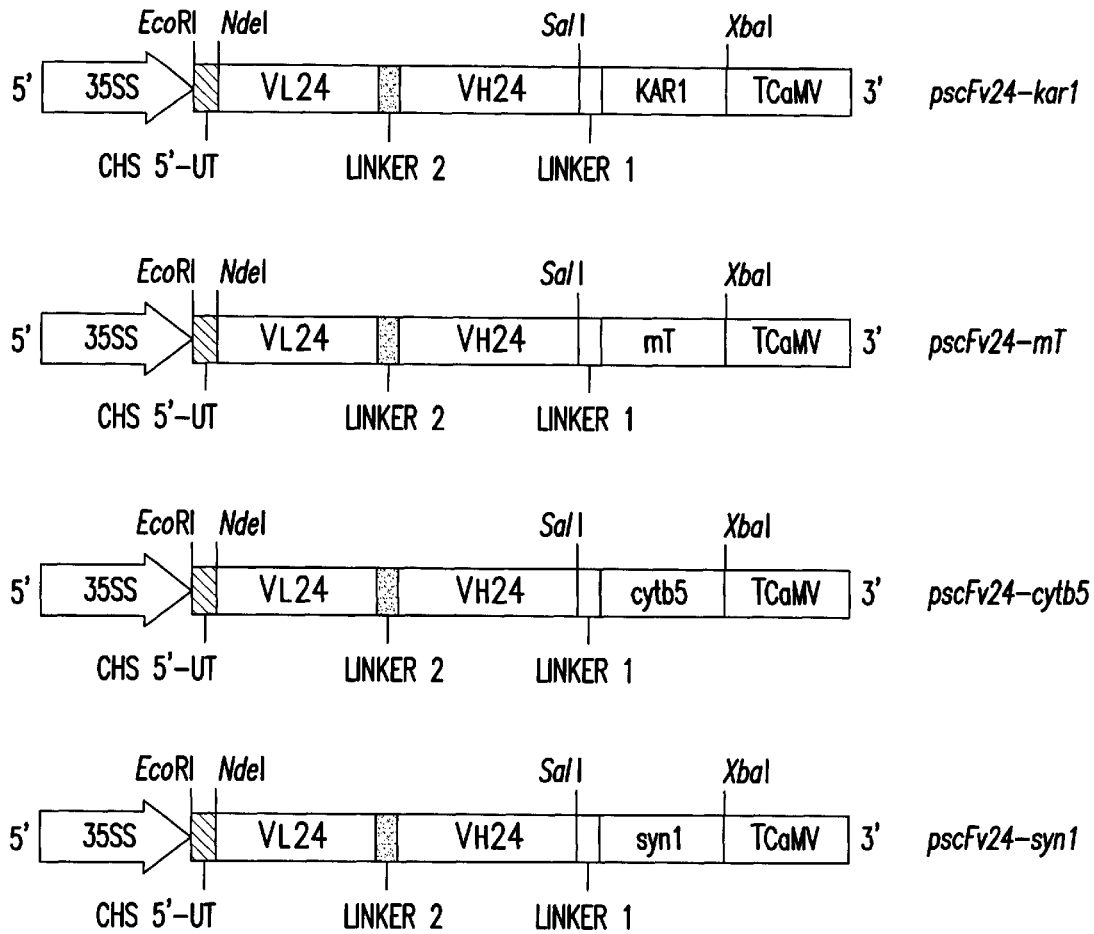
Figure 12B:
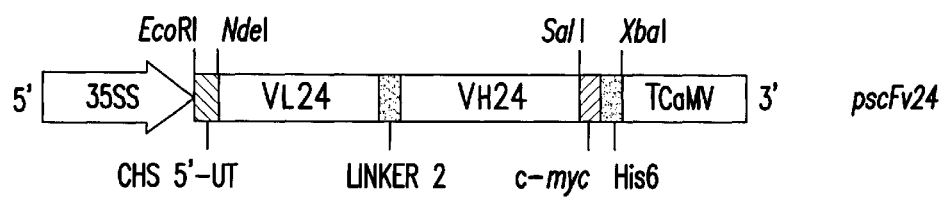

In young leaves of the transgenic $T_0$ plant $T4_{SR1}$ producing scFv24-TcRβ, scFv24 was localized to both the nuclear and plasma membranes (FIG. 11), confirming the subcellular localization of scFv24-TcRβ by immunofluorescence in transgenic N. tabacum cv. BY-2 protoplasts. The number of gold particles found in chloroplasts, mitochondria, glyoxysomes, cytoplasmic matrices and vacuoles was consistent with background labeling.

Bioassays of Viral Resistance

To analyze the biological effects of the membrane anchored anti-viral TMV-specific antibody on viral resistance, $T_1$ progenies of plant line expressing the scFv24-TcRβ fusion protein ($T6_{SR1}$) were inoculated with TMV.

Seeds were collected from antibody-producing $T_0$ plants and germinated on MSMO agar medium supplemented with 2% (w/v) sucrose, 0.4 μg/ml thiamine, 0.4 μg/ml glycine, 0.1 μg/ml nicotine acid, 0.1 μg/ml pyridoxine and 75 μg/ml kanamycin. Kanamycin-resistant $T_1$ plants were used for inoculation with TMV-v (1 μg/ml) as previously described (Dietzgen, Arch. Virol. 87: 73–86 (1986)). Wild type N. tabacum cv. Petite Havana SR1 plants were used as a control. Disease symptoms were monitored 6 to 20 days post inoculation (p.i.) and for resistant plants up to 180 days p.i.

Lower leaves were infected with TMV and systemic spread of the virus was followed by analyzing upper leaves 6–20 days later. All control non-transgenic tobacco plants were systemically infected, but 16% (out of 31 analyzed) of scFv24-TcRβ transgenic plants had no visible disease symptoms on the upper leaves (Table 2). Furthermore, ELISA analysis demonstrated that some of these plants accumulated virus particles in the upper leaves indicating that though systemic viral spread occurred, no symptoms were developed. Strikingly, in 6% of scFv24-TcRβ transgenic plants no virus was found in the upper leaves up to 90 days post inoculation. Virus could be detected at inoculation sites in the lower leaves by ELISA demonstrating that these plants had been efficiently inoculated with TMV. Antibody-fusion protein expression levels correlated with expression of TMV resistance (Table 2). Higher levels of scFv24 fusion protein expression led to an increased fraction of virus resistant plants, confirming that membrane anchored scFvs could be used to generate plants resistant to virus.

Conclusions

The recombinant fusion protein scFv24-TcRβ was functionally expressed in transgenic tobacco suspension cultures and transgenic plants. Expressed scFv24-TcR recognized TMV in ELISA and showed the expected size in immoblot analysis. Furthermore, immunofluorescence and electron microscopy showed that the TcR• transmembrane domain targeted scFv24 to the tobacco plasma and nuclear membrane. Bioassays of viral infection showed that transgenic tobacco plants expressing scFv24-TcR• were resistant to systemic TMV infection. These results demonstrated that membrane anchored anti-viral antibody fragments are functional, can be targeted to the plasma membrane in planta and are a novel method to shield plant cells from invading pathogens.

TABLE 1

Levels of functional scFv24 fusion protein in the $T_0$ generation of transgenic N. tabacum cv. Petite Havanna SR1.
Total soluble plant protein was isolated from leaves of transgenic plants producing scFv24-TcRβ. scFv24-fusion protein expression was quantified by TMV-specific ELISA using anti-mAb24 antisera and expressed as ng scFv24 per g leaf tissue.

| Construct | Number of transgenic plants | Number of plants expressing functional scFv24 | Range of expression (ng/g leaf tissue) | Average expression (ng/g leaf tissue) |
| --- | --- | --- | --- | --- |
| pscFv24-TcRβ | 6 | 6 | 30–8866 | 1991 |

TABLE 2

Virus infection assay of trangenic plants expressing membrane anchored scFv24. 1 μg/ml TMV-v was applied onto a lower leaf of non-transgenic N. tabacum cv. Petite Havana SR1 and transgenic $T_1$ progenies from plant line $P9_{SR1}$ producing scFv24-PDGFR or $T6_{SR1}$ producing scFv24-TcRβ. scFv24-fusion protein levels were determined by ELISA using the anti-mAb24 antisera 14 days p.i. and used for group formation (low, average and high producers).

| Plant lines | Tested plants | ng scFv24 per g leaf tissue | Healthy pheno-type[a] | Re-sistant plants[b] | Level of re-sistance (%)[c] |
| --- | --- | --- | --- | --- | --- |
| N. tabacum cv. Petite Havana SR1 | 62 | — | 0 | 0 | 0 |
| $T6_{SR1}$, low producer | 22 | 10–500 | 1 | 0 | |
| $T6_{SR1}$, average producer | 2 | 501–2000 | 2 | 1 | 6(16) |
| $T6_{SR1}$, high producer | 7 | 2001–21500 | 2 | 1 | |

[a] = upper leaves showed no visible disease symptoms;
[b] = based on TMV-ELISA;
[c] = level of resistance of all low, average and high producers, numbers in brackets include all plants without visible disease symptoms.

Example 2

Expression of a Neutralising Anti-viral Antibody with a C-terminal Membrane Localisation Sequence Cytoplasmic Presentation of a Membrane Localised Recombinant Antibody against the Coat Protein of Tobacco Mosaic Virus (TMV)

The steps 1) to 16) of example 1 are repeated with the following adaptations.

1) The N-terminal signal sequence is removed and replaced by a start codon.
2) The C-terminal membrane localisation sequence including the linker sequence of example 1 are replaced by suitable linker and C-terminal targeting sequences to posttranslationally target and integrate recombinant proteins into the bilayer of endomembranes. Suitable targeting sequences include transmembrane domains of KAR1 for nuclear membrane integration (Rose and Fink, 1987), middle-T antigen for plasma membrane integration (Kim et al., 1997) and cytochrome b5 for ER membrane integration (Kim et al., 1997). Moreover, prenylation, farnesylation, palmitoylation, myristoylation and ankyrin sequence motifs can be incorporated.

Anyone of skill in the art will recognise that these steps can be followed for any other pathogen by selecting antibodies or fragments thereof specific for the target pathogen. For example, antibodies can be raised against structural and non structural proteins of any pathogen. Membrane anchor sequence(s) can be substituted against any sequence that facilitates membranes integration and provides a biological function. Moreover, example 2 can be combined with examples 1 and 3–8 in any-combination(s).

Construction of the scFv24 Fusion Expression Cassette

To integrate the TMV-specific scFv24 into the bilayer of endomembranes the antibody fragment was fused to a C-terminal receptor transmembrane domain. No N-terminal signal sequence was included, therefore the scFv fragment is facing to the cytosol. The transmembrane domain sequence of KAR1 was selected for nuclear membrane integration (Rose and Fink, 1987), middle-T antigen for plasma membrane integration (Kim et al., 1997), cytochrome b5 for ER membrane integration (Kim et al., 1997) and syn1 for integration into vesicles (Kim et al., 1997). To ensure proper folding of the expressed single chain antibody fragments, the constructs scFv24-kar1, scFv24-mT, scFv24-cytb5 and scFv24-syn1 contained a $Gly_4Ser$ linker sequence between the scFv24 fragment and the membrane anchor (FIG. 12).

The C-terminal transmembrane domains KAR1, middle-T (mT), cytochrome b5 (cytb5) and synaptobrevin 1 (syn1) including the $Gly_4Ser$ linker sequence were fused to the scFv24 by PCR. The template scFv24CW cDNA (Zimmermann et al. (1998)), the forward primer −40 (5'-GTT TTC CCA GTC ACG AC-3' (SEQ ID NO:4)) and the following backward primers were used for PCR amplification: for kar1 5'-GGC TCT AGA CGC TCG AGT TTA AAA CCT ATA ATA CAC ATA GAT GTT GCA ATA AAG CAA AAT CAG TAT ACA AAT AGT CCA CCA GAA ATA CTC CCT ATA CTT CTT AGC GGC CGC AGA ACC TCC ACC TCC GTC G-3' (SEQ ID NO:5); for mT 5'-GGC TCT AGA CGC TCG AGT TTA GAA ATG CCT AGA TCT CTT AAT CAA GAT GAA GAG CAT CAA GCA AAT TCC GAG CAG CGC TGC CAA GAA AGT CAC CAA GAG CAA AGT TCT TCC CAA TCT CCT AGC GGC CGC AGA ACC TCC ACC TCC GTC G-3' (SEQ ID NO:6); for cvtb5 5'-GGC TCT AGA CGC TCG AGT TTA ATC CTC TGC CAT GTA GAG TCT ATA CAT GAG AGC AAC CAC GAG TGC TGA TAT CGC TGG GAT CAC CCA ATT GGT CCA CCA TGA AGA GTT AGA CTC AAC AGC GGC CGC AGA ACC TCC ACC TCC GTC G-3' (SEQ ID NO:7) and for syn1 5'-GGC TCT AGA CGC TCG AGT TTA AGT GAA GAA ATA AAT AAC AAT AAC AAC AAC AAT AAT AGC ACA AAT AGC ACC AAG CAT AAT CAT CAT CTT ACA ATT CTT CCA AGC GGC CGC AGA ACC TCC ACC TCC GTC G-3'(SEQ ID NO:8). The codons of the transmembrane domains were codon optimized for expression in tobacco, pea and wheat. The 5'-EcoRI and 3'-XbaI restricted PCR fragments were subcloned into pUC18 and sequenced. Mutations in the mT and syn1 transmembrane domain were eliminated by PCR using the forward primer −40 (5'-GTT TTC CCA GTC ACG AC-3' (SEQ ID NO:9)) and the backward primers MUT7MT 5'-GGC TCT AGA CGC TCG AGT TTA GAA ATG CCT AGA TC-3' (SEQ ID NO:10) for mT and SYN1SHORT 5'-GGC TCT AGA CGC TCG AGT TTA AGT GAA GAA ATA AAT AAC AAT AAC AAC AAC-3' (SEQ ID NO:11) for syn1. The chalcone synthase 5' untranslated region and scFv24 was substituted by the EcoRI and SalI fragment from scFv24CW (Zimmermann et al. (1998)). The subsequent ligation of the EcoRI-XbaI fragments into the plant expression vector pSS, containing an double enhanced 35S promoter (Voss et al. (1995)), resulted in the final expression constructs pscFv24-kar1, pscFv24-mT, pscFv24-cytb5 and pscFv24-syn1 (FIG. 12).

Transient Expression in Tobacco Leaves

To analyze the expression level of the recombinant scFv-fusion proteins, *N. tabacum* cv. Petite Havana SR1 leaves were transiently transformed with recombinant *A. tumefaciens* and functional expression of the scFv24 domiain of the fusion protein was analyzed by ELISA using anti-mAb24 antisera.

The vector constructs were transferred into *A. tumefaciens* GV3101 by liquid $N_2$ transformation (Höfgen and Willmitzer (1988)). Transient transformation of *N. tabacum* cv. Petite Havana SR1 was performed as described (Kapila et al., Plant Science 122 (1996) 101–108). To extract total soluble proteins, Tobacco leaves were frozen and ground in liquid nitrogen and scFv-fusion protein level was analysed by ELISA using anti-mAb24 antisera (Zimmermann et al. (1998)) as a primary antibody in combination with a 1:5000 dilution of goat anti-rabbit alkaline phosphatase conjugated secondary antibodies (Jackson Immuno Research Laboratories, West Grove, Pa.) (Fischer et al. in: C. Cunningham, A. J. R. Porter, (Eds.), Methods in biotechnology Vol. 3: Recombinant proteins in plants: Production and Isolation of Clinically useful compounds. Humana Press, Totowa, N.J. (1998), ELISA III).

The fusion proteins scFv24-mT, scFv24-syn1 and the control scFv24 lacking a C-terminal transmembrane domain were not detectable in plant extracts from transient transformation experiments (detection limit: 0.5 ng per gram leaf tissue). However, scFv24-kar1 and scFv24-cytb5 accumulated in the cytosol of plant cells to a maximum level of 1.8 ng and 1.0 ng per gram leaf tissue, respectively.

Conclusions

Generation of stable transformed *N. tabacum* cv. Petite Havana SR1 and bioassays to analyse the biological effects of cytosolic scFv24-kar1 and scFv24-cytb5 in transgenic tobacco plants are in progress. Based on our results with the scFv24-TcRβ (example 1) integration of the fusion proteins into the plant cell membrane was expected via the C-terminal transmembrane domains KAR1 or syn1. The scFv24 is facing to the plant cytosol, which will result in an increased viral resistance because the biological effect of scFv24 is high in the plant cytosol and membrane integration targets the scFv24 to the localisation where the virus is most vulnerable. The virus replication and movement takes place at plant cell membrane systems, therefore virus dissambly will be effectively prevented.

Example 3

Viral Resistance by Expression of a Molecular Pathogenicide

Fusion of a Nuclease Activity to a Recombinant Antibody Specific for TMV

The steps 1) to 16) of example 1 and/or the steps 1) to 2) of example 2 are repeated with the following adaptations.

1) The plant expression construct contains a 5' signal sequence to enable delivery of the recombinant antibody to the ER lumen and then secretion to the apoplast.

2) The transmembrane targeting domain is replaced by linker coupling the protein to a C-terminal fusion with a toxin—in this case an RNAse enzyme which degrades cellular RNA, viral RNA, replicative forms and/or replicative intermediates.
3) Upon binding to the virions in the apoplast, the fusion protein will enter the cytosol of damaged cells via the entering virions, where the cytotoxic RNase will degrade viral RNA, replicative intermediates and replicative forms or/and cellular RNA and cause cell death of virally infected cells and therefore prevent replication and spread of the pathogen.

Anyone of skill in the art will recognise that these steps can be followed for any other pathogen by selecting antibodies or fragments thereof specific for the target pathogen. For example, antibodies can be raised against structural and non structural proteins of any pathogen. The RNase sequence(s) can be substituted against any enzyme sequence that interferes in the pathogen life cycle. Moreover, example 3 can be combined with examples 1–2 and 4–8 in any combination(s).

Construction of the scFv24 Fusion (immunotoxin) Expression Cassette

To generate an apoplastic expressed immunotoxin, the TMV-specific scFv24 was fused to an N-terminal mammalian signal peptide and C-terminal toxin. The mouse N-terminal light chain signal peptide from the original antibody (mAb24) used to generate scFv24 was used to target fusion proteins to the secretory pathway. The domain III of the Pseudomonas exotoxin (PE) was selected for fusion with the C-terminus of scFv24. The domain III of the Pseudomonas exotoxin mediates the ADP-ribosylation of elongation factor 2, which arrests protein synthesis and causes cell death. To ensure proper folding of the expressed single chain antibody fragments, the cDNA construct contained the cellobiohydrolase I (CBHI) linker of *Trichoderma reesi* (Mallender and Voss, 1994, J. Biol. Chem. 269, 199–206) between the scFv24 fragment and the domain III of the PE. A 12 amino acid residue epitope tag (tag54) was fused to the C-terminus via a Gly$_4$Ser linker to enable detection of the recombinant protein in plant extracts.

Figure 13:
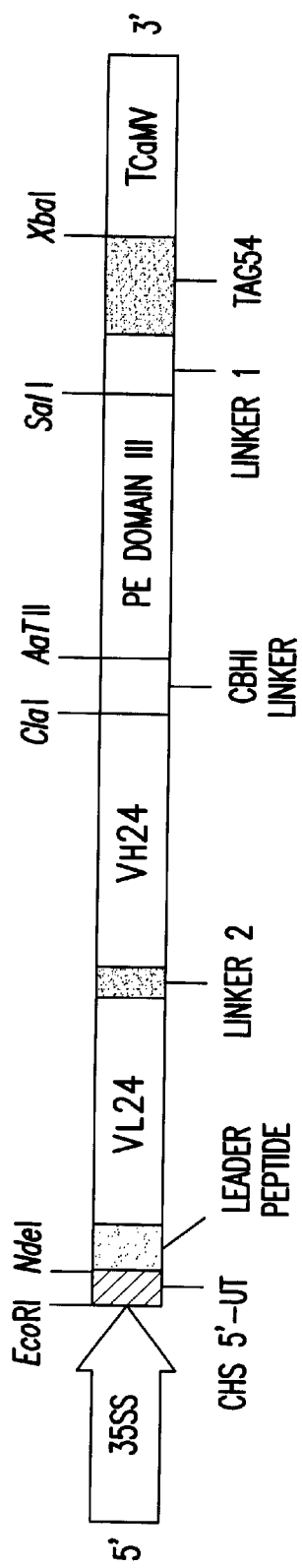

The PE domain III was PCR amplified from the plasmid PE38 (Theuer et al., Cancer Res 15, 340–347 (1993)) using the primers PE400-for 5'-GCG GAA TTC GAC GTC GCC ATG GCC TTC CTC GGC GAC GGC GGC GAC-3' (SEQ ID NO:16) and PE-back 5'-GCG AAG CTT GTC GAC CGG CGG TTT GCC GGG CTG GCT G-3' (SEQ ID NO:17). The primers contained restriction sites EcoRI, AatII and NcoI (PE400-for) and SalI and HindIII (PE-back) for cloning. The PCR fragment was subcloned via EcoRI and HindIII into pUC18 resulting in the construct PE400-intermediate and the sequence was verified by sequencing. To generate the immunotoxin, the scFv29 sequence from the biscFv2429-apoplast in pUC18 (Fischer et al., *Eur. J. Biochem.* 262, 810–816 (1999)) was removed by AatII and SalI and exchanged by the AatII (internal restriction site) and SalI fragment of PE400-intermediate. Finally, the EcoRI and SalI fragment containing the chalcone synthase 5' untranslated region, the leader signal of mAb24 light chain (Voss et al., 1995), the scFv24, the CBHI linker and PE domain III was subcloned into the EcoRI and SalI restriction sites of pSS derivate containing the enhanced 35S promoter (Kay et al., 1987), the epitope tag54 and the CaMV termination sequence resulting in the final plant expression construct pscFv24-PE400 (FIG. 13).

Conclusions

Generation of stable transformed *N. tabacum* cv. Petite Havana SR1 and bioassays to analyse the biological effects of scFv24-PE400 in transgenic tobacco plants are in progress. However, PE280-tag29 was transiently expressed in tobacco leaves and a slightly degraded product of was detected in plant extracts of transient transformed tobacco leaves, indicating that PE280-tag29 is most likely expressed and secreted to the apoplast and therefore not toxic to the plant cells (see example 7). Consequently, expression of the immunotoxin scFv24-PE400 will be non-toxic to plants. The scFv24-PE fusion (scFv24-PE400) will be secreted to the apoplast of transgenic tobacco plants. During TMV infection the fusion protein will bind to the virus particle via the scFv24 (as shown for the full-size rAb24) and TMV virions that enter the cell will carry bound scFv24-toxin fusion. PE400 mediates the ADP-ribosylation of elongation factor 2, which arrests protein synthesis and causes cell death. PE is a very effective toxin, as only a few molecules are required to kill the infected cell, thus preventing virus replication and spread, leading to highly resistant plants.

Molecular Pathogenicide Fusion (RNAse Fusion)

A C- or N-terminal fusion of a coat protein specific antibody scFv gene (scFv24) with a cDNA encoding a RNAse gene (for example *E. coli* RNAse E) results in an scFv-enzyme fusion protein which can be targeted to the plant cytoplasm—or to cellular organelles, membranes, or the apoplast to interfere in viral replication.

Such an scFv-RNAse fusion was engineered based on the TMV-specific scFv24 which binds to the intact TMV virions instead of coat protein alone. This scFv24 was chosen for targeting the viral RNA at the earliest timepoint of the viral infection cycle to immediately act on the released viral RNA upon viral dissassembly. A second contruct is based on a 30K specific scFv-RNAse fusion which follows the same set up as given in FIG. 14 based on the scFv24. This scFv is described in Example 5 (scFv 30-1 or scFv 30-2) and will be coexpressed with the scFv24-RNaseE fusion in double transgenic plants transformed with both constructs. For fusion to the above mentioned scFv antibodies the *E. coli* RNAse E. was selected (Claverie-Martin et al., *J. Biol. Chem.* 266, 2843–2851] and connected to the scFv upon PCR-amplification using standard cloning technologies known by any person skilled in the art.

Example 4

Enhanced Coat Protein Mediated Resistance with an Antibody-viral Coat Protein Fusion Protein Fusion of a Viral Coat Protein to a Recombinant Antibody Specific for TMV The steps 1) to 16) of example 1 and/or the steps 1) to 2) of example 2 are repeated with the following adaptations.
1) The transmembrane targeting domain listed in example 1 are removed but the C-terminal anchor and linker sequences of example 2 can be maintained.
2) The N-terminal signal sequence of example 1 is replaced by an upstream located (N-terminal) TMV coat protein monomer and then connected via a flexible linker to the recombinant antibody cDNA.
3) The fusion protein is expressed in the cytosol.
4) Alternatively, the transmembrane domain is replaced by a linker enabling C-terminal fusion with the TMV coat protein monomer. The fusion protein is expressed in the cytosol (without N-terminal signal sequence) or sent into the secretory pathway via a N-terminal signal peptide.

Anyone of skill in the art will recognise that these steps can be followed for any other pathogen by selecting antibodies or fragments thereof specific for the target pathogen. For example, antibodies can be raised against structural and non structural proteins of any pathogen. The N-terminal coat protein sequence(s) can be substituted against any sequence (for example Glutathione S-Transferase, Thioredoxin, plant virus movement proteins, replicase, minimal proteins or domains thereof) that stabilises a cytosolic expressed recombinant antibody and interferes in the pathogen life cycle. Moreover, example 4 can be combined with examples 1–3 and 5–8 in any combination(s).

Construction of the scFv24 Fusion Expression Cassettes

A cytoplasmically expressed protein (the coat-protein of tobacco mosaic virus) was selected as fusion partner to analyse its effect on the function and stability of the TMV-specific scFv24. The tobacco mosaic virus coat protein (CP) was cloned 5' upstream-of the scFv24 (FIG. 15).

The gene fusion partner coat protein (CP) from TMV was amplified by PCR. cDNAs was amplified from a cDNA clone from TMV as a template. The forward primers introduced a NcoI restriction site (5' end) and the backward primers a C-terminal $(Gly_4Ser)_2$ linker sequence and an AatII restriction site (3' end). The following forward and backward primers were used for PCR amplification: CP-for 5'-ACT GCG CCA TGG CTT ACA GTA TCA CT-3' (SEQ ID NO:20), CP-back 5'-CCG TCA GAC GTC AGA ACC TCC ACC TCC ACT TCC GCC GCC TCC AGT TGC AGG ACC AGA GGT CCA AAC CAA ACC-3' (SEQ ID NO:21). The 5'-NcoI and 3'-AatII restricted PCR fragments were subcloned into a pUC18 derivative containing the TMV specific scFv24 (Zimmermann et al., 1998) flanked by the 5' Ω untranslated region (omega-sequence) and 3' untranslated region (Pw sequence) from TMV (Schmitz et al., Nucleic Acids Res 24 (1996) 257–263); (Gallie and Kobayashi, Gene 142 (1994) 159–165). A C-terminal His6- (H) or KDEL-sequence (K) were added to scFv24 of the fusion construct by PCR using the backward primers: His6-back 5'-CTA CCC CTC GAG TTT AGT GAT GGT GAT GGT GAT GAG CGG CCG CGT CGA CTG CAG AGA CAG TGA CCA GAG TC-3' SEQ ID NO:22) and KDEL-back 5'-CCC TCA CTC GAG TTT AGA GCT CAT CTT TCT CAG ATC CAC GAG CGG CCG CAG AAC CTC CAG CTC CGT CGA CTG CAG AGA CAG TGA CCA G-3' (SEQ ID NO:23). The subsequent ligation of the EcoRI-AscI fragments into the plant expression vector pSS, containing an double enhanced 35S promoter (Voss et al., 1995), resulted in the final expression constructs CP-scFv24H and CP-scFv24K, which were used for analyzing scFv-fusion protein accumulation in the cytoplasm (FIG. 15A).

For ER targeting and retention, the plant codon optimized leader sequence derived from the light chain of the murine monoclonal antibody mAb24 (Voss et al., 1995) was integrated between the 5' Ω untranslated region and scFv24 of the cytoplasmic construct containing the KDEL sequence, giving the plant expression vector L-CP-scFv24K (FIG. 15C). For targeting the same construct to the apoplast, the c-terminal KDEL sequence was replaced by a His 6 sequence, giving the plant expression vector L-CP-scFv24H (FIG. 15D).

Two expression vectors lacking a leader sequence and an N-terminal fusion partner but containing scFv24 with a C-terminal His6 or KDEL sequence were used as controls for cytoplasmic accumulation (scFv24H, scFv24K, FIG. 15B).

Analysis of Fusion Protein Accumulation in the ER

Accumulation of functional fusion protein in the ER was analysed by transient expression in *N. tabacum* cv. Petite Havana SR1 leaves and functional scFv24 was detected by a TMV-specific ELISA. Plant expression constructs were transferred into *A. tumefaciens* GV3101 by $N_2$ transformation (Höfgen and Willmitzer, Nucleic Acids Res 16 (1988) 9877). Transient transformation of *N. tabacum* cv. Petite Havana SR1 was performed as described (Kapila et al., Plant Science 122 (1996) 101–108). To extract total soluble proteins, Tobacco leaves were frozen and ground in liquid nitrogen and scFv-fusion protein level was analysed by ELISA and Western blot (Fischer et al., Methods in biotechnology Vol. 3: Recombinant proteins in plants: Production and Isolation of Clinically useful compounds. Humana Press, Totowa, N.J. (1998), ELISA III). A Fab fragment of the mAb24 was used as the ELISA standard. Protein concentrations were determined with the BioRad Protein Assay using bovine serum albumin (BSA) as the standard.

The level of functional scFv24 detected for the ER retained L-CP-scFv24K fusion protein, amounted to 1 μg per gram leaf material (average 0.6 μg per gram leaf material, FIG. 16).

To verify the integrity of scFv24 fusion proteins, western blot analysis was carried out using affinity purified L-CP-scFv24K. For affinity purification of scFv-fusion proteins from plant extracts (prepared as described above), TMV virions were coupled to an activated CNBr sepharose matrix. 300 mg of CNBr activated sepharose 4B matrix (Pharmacia, Freiburg, Germany) was resuspended in 1 ml PBS pH 7.4 (1.37M NaCl, 27 mM KCl, 81 mM $Na_2HPO_4$, 15 mM $KH_2PO_4$) and incubated for 1 h at RT on a rotator. The matrix was pelleted (5000×g, 5 min, RT), resuspended in 1 ml PBS pH7.4 containing 10 mg TMV virions and incubated for 2h at RT on a rotator. The TMV coupled matrix was centrifuged (5000×g, 5 min, RT), resuspended in 1 ml PBS pH 7.4 containing 1% (w/v) BSA and 1% (w/v) powdered milk and rotated over night at 8° C. to block nonspecific binding sites. The TMV coupled matrix was washed three times with PBS pH 7.4 and resuspended in 1 ml PBS pH 7.4. 30 μl TMV-matrix was added to 1.5 ml plant extract (prepared as described above) and incubated for 1 h at RT on a rotator. Then the TMV-matrix was washed three times with PBS and the TMV-matrix bound proteins were solubilised in sample buffer and analysed by SDS-PAGE (Laemmli, Nature 227 (1970) 680–685) and Coomassie brillant blue staining. Intact fusion proteins were detected with the expected size of 49.5kDa for L-CP-scFv24K (FIG. 17).

Analysis of Fusion Protein Accumulation in the Cytoplasm

For transient cytoplasmic accumulation of fusion proteins *N. benthamiana* leaves were used. The vector constructs were transferred into *A. tumefaciens* GV3101 by liquid $N_2$ transformation (Höfgen and Willmitzer, Nucleic Acids Res. 16: 9877 (1988)). Transient transformation of *N. benthamiana* was performed as described (Kapila et al., Plant Science 122 (1996) 101–108). To extract total soluble proteins, Tobacco leaves were frozen and ground in liquid nitrogen and scFv-fusion protein level was analysed by ELISA and Western blot (Fischer et al., Methods in biotechnology Vol. 3: Recombinant proteins in plants: Production and Isolation of Clinically useful compounds. Humana Press, Totowa, N.J. (1998), ELISA III). A Fab fragment of the mAb24 was used as the ELISA standard.

Analysis using the constructs containing the C-terminal His6 sequence (FIG. 15) demonstrated that CP-scFv24H was detectable in a TMV-specific ELISA, with an average protein level of 0.9 ng functional active scFv24 per gram leaf material. Protein levels of the control construct scFv24H lacking an N-terminal fusion partner was below the ELISA detection limit (0.5 ng) (FIG. 18).

We evaluated the influence of a C-terminal KDEL sequence on the accumulation of scFv24 fusion proteins. Addition of the C-terminal KDEL sequence increased the level of the fusion protein (FIG. 18). The average protein level of the KDEL tagged CP-scFv24K was 3fold higher than CP-scFv24H (2.9 ng per gram leaf material). Level of the control construct scFv24K was below the ELISA detection threshold. A control ELISA performed without the antigen TMV gave no signal, indicating that values of CP-scFv24H and CP-scFv24K could not be correlated with specific binding of CP-fusions to anti TMV polyclonal sera.

Characterization of Transgenic Plants Expressing Cytoplasmic scFv Fusion Proteins We then tested to which level the cytoplasmically expressed CP-scFv24K accumulated in stably transformed tobacco plants. Transgenic N. tabacum cv. Petite Havana SR1 were generated by the leaf disc transformation with recombinant A. tumefaciens and transgenic $T_0$ plants were generated from transformed callus (Horsch et al., Science 227: 1229–1231 (1985)). Extraction of total soluble proteins from tobacco leaves and subsequent analysis of scFv24 by ELISA were performed as described by Fischer et al. (Fischer et al., In: Cunningham C, Porter A J R (eds), Recombinant proteins in plants: Production and Isolation of Clinically useful compounds, pp. 45–68. Vol. 3. Humana press, Totowa, N.J. (1998)). For ELISA anti-mAb24 antisera (Zimmermann et al., Molecular Breeding 4: 369–379 (1998)) was used as a primary antibody in combination with a 1:5000 dilution of goat anti-rabbit alkaline phosphatase conjugated secondary antibodies (Jackson Immuno Research Laboratories, West Grove, Pa.) (Fischer, Methods in biotechnology Vol. 3: Recombinant proteins in plants: Production and Isolation of Clinically useful compounds. Humana Press, Totowa, N.J. (1998), ELISA III).

Protein levels of CP-scFv24K showed an average of 1.2 ng per gram leaf material in 12 analysed transgenic N. tabacum cv. Petite Havana SR1 plants. The maximum level of detergent extracted CP-scFv24K was 2.3 ng per g leaf tissue, thus higher than the scFv24 without fusion partner and KDEL sequence (maximum 1.8 ng/g leaf tissue; average 0.8 ng/g leaf tissue; Zimmermann et al., Molecular Breeding 4 (1998).

Conclusions

Bioassays to analyse the biological effects of cytosolic CP-scFv24K in transgenic N. tabacum cv. Petite Havana SR1 plants are in progress. Based on other inoculation experiments, an increase of viral resistance can be expected when compared to cytosolic scFv24 without fusion partner which creates a resistant phenotype, based on the increase of scFv24 protein levels and the presence of TMV-CP and TMV-RNA sequences to induce CP-mediated and RNA mediated virus resistance in addition to the primary antibody resistance.

Example 5

Enhanced Resistance by the Expression of an Antiviral Movement Protein Antibody

Expression of Recombinant Antibodies Against the TMV 30K Movement Protein in Transgenic Tobacco The steps 1) to 16) of example 1 and/or the steps 1) to 2) of example 2 are repeated with :the following adaptations.
1) Specific antibodies recognising the TMV 30K movement protein are raised by hybridoma technology, phage or ribosome display screening and subsequently cloned to engineer single chain antibodies or any recombinant form thereof.
2) The antibody is expressed in the cytosol or sent into the secretory pathway or membrane localised. The recombinant antibody may cause the desired biological effect without a fusion partner so the toxin sequence may be omitted.
3) For ELISA and surface plasmon resonance the test antigen for antibody function is the native or the recombinant TMV 30K movement protein or domains thereof.
4) Additionally to the bioassays listed in example 1 generated transgenic plants will be tested for broad spectrum resistance against different viral strains or viral genera by inoculation of transgenic plants with virions or infectious transcripts.

Anyone of skill in the art will recognise that these steps can be followed for any other viral pathogen by selecting antibodies or fragments thereof specific for the movement protein and any functional domain. Moreover, example 5 can be combined with examples 1–4 and 6–8 in any combination(s).

Generation of Anti-30K Movement Protein Specific Antibodies by Phage Display

Movement protein (MP)—specific recombinant antibodies were generated by phage display using bacterially expressed 30K TMV movement protein fused to GST to faciliate affinity purification (Pharmacia GST-System). Female Balb/c mice were immunized using a standard protocol with soluble GST-30K fusion proteins or domains thereof. The native structure of the GST and the fused 30K was tested by GST activity assay (Smith et al., Gene 67 (1988), 31–40) and RNA binding of the 30K (Vaquero, J. Gen. Virol. 78 (1997) 2095–2099). Antibody $V_H$- and $V_L$-regions were subsequently rescued from plasma cells of hyperimmunized mice and assembled to scFv antibodies using an SOE-PCR protocol (Mc Cafferty et al., Nature 348 (1990), 552–554). An extended set of PCR-primers for $V_H$ and $V_L$ family specific amplification was developed and used (Table 4). Using this protocol a library>$10^6$ different scFv was generated for scFv presentation on the phage surface in fusion to the gene III M13-pilot protein. Using phage display a panel of 10 different movement protein specific antibodies could be isolated and characterised which all showed strong binding affinity to the bacterial expressed GST-30K fusion protein and not to the bacterially expressed GST-protein alone (FIG. 20a). The binding domain of these 10 antibodies on the 30K were mapped by expression of 5 distinct 30K domains and ELISA analysis (FIG. 20b). For evaluation of the biological effects of plant expressed anti 30K antibodies the 6 strongest binders were subsequently cloned into plant expression vectors and expressed and analysed by phenotypic evaluation and molecular analyses to evaluate their effects on viral infection with TMV. From these experiments two plant lines expressing the antibody fragments scFv 30-1 and scFv 30-2 (FIG. 21) showed significant inhibition on TMV infection confirmed by a healthy phenotype of the plants, reduced amount and delayed accumulation of TMV coat protein compared to wild type N. tabacum Petite Havana SR1.

Construction of the Anti-30K Antibody Expression Cassette for Expression in Plants To express the anti-30K antibodies in the cytosol of N. tabacum cv. Petite Havana SR1, the antibody fragments were cloned into the plant expression vector pSSH1. (FIG. 19) (Voss et al., Molecular Breeding 1 (1995), 39–50). The cloning of the bispecific antibody fragment BISCA2429, which was used as parental construct for anti-30K antibody expression, including the TMV-derived Omega sequence, into the plant expression vector pSSH1 has been described (Fischer, et al., (1999) Eur. J. Biochem. 262, 810–816). For cloning of the resulting scFvs into this vector the primers used for establishing the phage display library contained the restriction enzyme sites NcoI and SalI which faciliated the in-frame cloning into the intermediate construct pUC18-

BISCA2429 (5'-UTR of TMV omega sequence, scFv, His6 tag). For expression in plant cells, the EcoRI/XbaI fragment (FIG. 19) of this intermediate construct was subcloned into the EcoRI and XbaI restriction sites of the plant expression vector pSS containing the enhanced 35S promoter (Kay et al., Science 236 (1987), 1299–1302) and the CaMV termination sequence (FIG. 19). The final constructs contained an expression cassette starting with the 35 SS promoter followed by the 5'-UT of the TMV omega sequence, the 30K specific scFv, a His6 tag for affinity purification and the 3'-UTR of CaMV (FIGS. 19 and 21).

Generation and Molecular Characterization of Transgenic Plants

Upon completion of scFv analysis in vitro, tobacco plants were stably transformed for in vivo testing of scFv effects on TMV infection. Transgenic N. tabacum cv. Petite Havana SR1 were generated by leaf disc transformation using recombinant A. tumefaciens and transgenic $T_0$ plants were generated from transformed callus (Horsch et al., Science 227 (1985), 1229–1231). From the $T_0$ generation several plants were selected and homozygous $T_1$ and $T_2$ progenies selected for phenotypic and molecular evaluation of scFv-antibody mediated resistance.

To test if the anti 30K-specific scFv expression in transgenic plants had an biological effect on TMV replication and spread within the plant, a time course based TMV coat protein assay was established where the amount of viral coat protein was monitored in upper leaves after infection of transgenic and nontransgenic plants with TMV vulgare. Extraction of TMV coat protein from systemically infected tobacco leaves and subsequent analysis on SDS-PAGE (Laemmli, Nature 227,(1970), 680–685) was performed as described by Fischer et al. (Fischer et al., (1998) In: Cunningham C, Porter A J R (eds), Recombinant proteins in plants: Production and Isolation of Clinically useful compounds, pp. 45–68. Vol. 3. Humana press, Totowa, N.J.). Monitoring the coat protein expression in systemically infected wild type and control tobacco leaves by western blotting revealed increasing amounts of the TMV coat protein. In case of plants-expressing the 30K specific scFvs, accumulation of coat protein was significantly delayed and levels were significantly lower compared to wild type N. tabacum cv. Petite Havana SR1, and transgenic N. tabacum Petite Havana SR 1 expressing a non-related scFv, used as control (FIG. 22). Although coat protein was detectable in all transgenic plants they developed no or only mild symptoms based on phenotypic evaluations (Table 3).

Bioassays to Test Viral Resistance

To analyse the biological effects of the TMV-specific 30K scFvs on viral resistance, $T_1$ and $T_2$ progenies of plant lines expressing the scFv 30-1 and scFv 30-2 S (FIG. 21) were inoculated with TMV. Seeds were collected from different $T_0$ plants and germinated on MSMO agar medium supplemented with 2% (w/v) sucrose, 0.4 μg/ml thiamine, 0.4 μg/ml glycine, 0.1 μg/ml nicotine acid, 0.1 μg/ml pyridoxine and 75 μg/ml kanamycin. Germinating plants were transferred to soil and fully grown $T_0$ plants self fertilized for seed collection. Kanamycin-resistant homozygous $T_1$ and $T_2$ plants were used for inoculation with TMV-vulgare (4C ng/ml). Four to six week old plants were mechanically infected on two lower leaves using 200 μl of the TMV containing suspension. *N. tabacum* cv. Petite Havana SR1 wild type or transgenic plants producing the tumorspecific scFv T84.66 as a control were inoculated as described. Disease symptoms were monitored 7 to 14 days post inoculation (p.i.).

Upon infection of the two lower leaves with TMV, systemic spread of the virus was monitored by phenotypic evaluation of upper leaves after 7, 9, 11 and 14 days p.i. All control plants were systemically infected, and showed increasing amounts of viral coat protein. Transgenic $T_1$ and $T_2$ plants derived from different $T_0$-plant lines expressing scFv 30K-1 or scFv 30K-2 showed no visible or weak disease symptoms on the upper leaves (Table 3). In cases where the symptom development was visible this was consistent among plants derived from one plant line. In the case of the scFv 30K-2 one plant line was obtained which showed severe symptoms in the $T_1$ as well as in the $T_2$ generation. This may be due to positional effects of the transgene or silencing effect of the transgene in the $T_1$ and $T_2$ generation. Furthermore, SDS-PAA based analysis and subsequent western-blotting of TMV coat protein accumulation over 72 hrs p.i. in infected plants demonstrated that all of these plants accumulated virus particles in the upper leaves although to a lower degree (FIG. 22). This lead to the conclusion that expression of movement protein specific scFv can prevent symptom onset and delay on CP accumulation upon TMV infection.

Other Viral Movement Proteins

To broaden the application of antiviral antibodies in transgenic plants for engineering resistance the 3a movement protein of cucumber mosaic virus was expressed in *E. coli* as a GST-fusion (Vaquero et al., (1997) J. Gen. Virol. 78, 2095–2099). Specific anti-3a antibodies were generated by phage display and hybridoma technology using bacterially expressed 3a CMV movement protein as already described for the 30K movement protein of TMV (FIG. 19). The mAb 3a-2 was cloned from hybridoma cells (Krebber et al., (1997). J. Immunol. Methods 201, 35–55) and the resulting scFv 3a-2 characterized in vitro by ELISA technique (FIG. **23*a***). Using epitope mapping by peptide display the epitope of the antibody could be mapped to a distinct region on the 3a movement protein.

TABLE 3

Phenotypic evaluation of TMV-30K-specific scFv expressing transgenic *N. tabacum* plants in the $T_1$ and $T_2$ generation. Different plants were tested from the $T_1$ and the $T_2$ generation for phenotypically visible disease symptoms upon infection of two lower leaves with 40 ng/ml TMV. Disease symptoms were monitored at 7, 9, 11 and 14 days p.i. in the most upper leaves.

| | $T_1$-Plants | | $T_2$-Plants | |
|---|---|---|---|---|
| Construct | No. of infected plants | symptoms | No. of infected plants | symptoms |
| pSS-scFv-30-1 | 55 | no symptoms after 11 to 14 days | 22 | weak symptoms after 14 days in all plants |
| pSS-scFv-30-2 | 124 | weak or medium, rarely severe symptoms | 65 | no to weak, rarely severe symptoms |

TABLE 4

Primers used for amplifying murine $V_H$ and $V_L$ antibody domains for scFv generation. These primers were used for cloning of scFvs prior to phage display as well as for cloning scFvs from preexisting hybridoma cell lines ("hybridoma rescue"). The specificity of all primers according to the Kabat-database (Kabat: "Sequences of immunological interest", 1991) is listed, all primers contain a 5'-noncoding 10 bp overhang to faciliate restriction enzyme digestion and cloning. For cloning $V_H$-fragments restriction enzymes Sfi I, Fse I, for cloning $V_L$-fragments restriction enzymes Asc I/ Not I were used.

| Name | Specificity according to Kabat (1991) | Overhang/Enzyme Region | Annealing region |
|---|---|---|---|
| MPD VHF 1 (SEQ ID NO: 31) | Mu $V_H$ IA Front | C ATG CCA TGA CTC GCG GCC CAG CCG GCC ATG GCC | GAK GTR CAG CTT CAG GAG TCR GGA |
| MPD VHF 2 (SEQ ID NO: 32) | Mu $V_H$ IB Front | C ATG CCA TGA CTC GCG GCC CAG CCG GCC ATG GCC | CAG GTG MAG CTG AWG GAR TCT GG |
| MPD VHF 3 (SEQ ID NO: 33) | Mu $V_H$ IIA Front | C ATG CCA TGA CTC GCG GCC CAG CCG GCC ATG GCC | GAG GTC CAG CTR CAR CAR TCT GGA CC |
| MPD VHF 4 (SEQ ID NO: 34) | Mu $V_H$ IIA Front | C ATG CCA TGA CTC GCG GCC CAG CCG GCC ATG GCC | CAG GTW CAG CTS CAG CAG TCT G |
| MPD VHF 5 (SEQ ID NO: 35) | Mu $V_H$ IIB Front | C ATG CCA TGA CTC GCG GCC CAG CCG GCC ATG GCC | SAG GTC CAR CTG CAG SAR YCT GGR |
| MPD VHF 6 (SEQ ID NO: 36) | Mu $V_H$ IIC Front | C ATG CCA TGA CTC GCG GCC CAG CCG GCC ATG GCC | GAG GTT CAG CTG CAG CAG TCT GGG |
| MPD VHF 7 (SEQ ID NO: 37) | Mu $V_H$ IIIA Front | C ATG CCA TGA CTC GCG GCC CAG CCG GCC ATG GCC | GAR GTG AAG CTG GTG GAR TCT GGR |
| MPD VHF 8 (SEQ ID NO: 38) | Mu $V_H$ IIIB Front | C ATG CCA TGA CTC GCG GCC CAG CCG GCC ATG GCC | GAG GTG AAG STY MTC GAG TCT GGA |
| MPD VHF 9 (SEQ ID NO: 39) | Mu $V_H$ IIIC Front | C ATG CCA TGA CTC GCG GCC CAG CCG GCC ATG GCC | GAR GTG AAG CTK GAK GAG WCT GR |
| MPD VHF 10 (SEQ ID NO: 40) | Mu $V_H$ IIID Front | C ATG CCA TGA CTC GCG GCC CAG CCG GCC ATG GCC | GAV GTG MWG CTK GTG GAG TCT GGK |
| MPD VHF 11 (SEQ ID NO: 41) | Mu $V_H$ IIID Front | C ATG CCA TGA CTC GCG GCC CAG CCG GCC ATG GCC | GAG GTG CAR CTK GTT GAG TCT GGT G |
| MPD VHF 12 (SEQ ID NO: 42) | Mu $V_H$ VA Front | C ATG CCA TGA CTC GCG GCC CAG CCG GCC ATG GCC | SAG GTY CAG CTK CAG CAG TCT GGA |
| MPD VHF 13 (SEQ ID NO: 43) | Mu $V_H$ 1 Front | C ATG CCA TGA CTC GCG GCC CAG CCG GCC ATG GCC | CAG ATC CAG TTG GTG CAG TCT GGA |
| MPD VHF 14 (SEQ ID NO: 44) | Mu $V_H$ 2 Front | C ATG CCA TGA CTC GCG GCC CAG CCG GCC ATG GCC | CAG GTS CAC STG RWG SAG TCT GGG |
| MPD VHF 15 (SEQ ID NO: 45) | Mu $V_H$ 3 Front | CAG GTS CAC STG RWG SAG TCT GGG | CAG GTT ACT CTR AAA GWG TST GGC C |
| MPD VHF 16 (SEQ ID NO: 46) | Mu $V_H$ 4 Front | C ATG CCA TGA CTC GCG GCC CAG CCG GCC ATG GCC | GAT GTG AAC TTG GAA GTG TCT GG |
| MPD VLF1 (SEQ ID NO: 47) | Mu kappa $V_L$ I Front | CAT GCC ATG ACT CGC GGC GCG CCT | GAC ATT GTG MTG WCH CAG TCT CCA |
| MPD VLF2 (SEQ ID NO: 48) | Mu kappa $V_L$ I Front | CAT GCC ATG ACT CGC GGC GCG CCT | GAC ATT CAG ATG ATT CAG TCT CC |
| MPD VLF3 (SEQ ID NO: 49) | Mu kappa $V_L$ I Front | CAT GCC ATG ACT CGC GGC GCG CCT | GAC ATT GTT CTC WHC CAG TCT CC |
| MPD VLF4 (SEQ ID NO: 50) | Mu kappa $V_L$ I Front | CAT GCC ATG ACT CGC GGC GCG CCT | GAC ATT GTG MTG WCH CAG TCT CAA |
| MPD VLF5 (SEQ ID NO: 51) | Mu kappa $V_L$ II Front | CAT GCC ATG ACT CGC GGC GCG CCT | GAT RTT KTG ATG ACC CAR RCK GCA |
| MPD VLF6 (SEQ ID NO: 52) | Mu kappa $V_L$ II Front | CAT GCC ATG ACT CGC GGC GCG CCT | GAT RTT KTG ATG ACC CAR RCK CCA |
| MPD VLF7 (SEQ ID NO: 53) | Mu kappa $V_L$ II Front | CAT GCC ATG ACT CGC GGC GCG CCT | GAC ATT GTG ATG ACC CAR BHT G |
| MPD VLF8 (SEQ ID NO: 54) | Mu kappa $V_L$ II Front | CAT GCC ATG ACT CGC GGC GCG CCT | GAT ATT KTG ATG ACC CAR AYT CC |
| MPD VLF9 (SEQ ID NO: 55) | Mu kappa $V_L$ III Front | CAT GCC ATG ACT CGC GGC GCG CCT | RAM ACT GTG MTG ACC CAA TYT CCW |
| MPD VLF10 (SEQ ID NO: 56) | Mu kappa $V_L$ IV Front | CAT GCC ATG ACT CGC GGC GCG CCT | SAA AWT GTK CTS ACC CAG TCT CCA |
| MPD VLF11 (SEQ ID NO: 57) | Mu kappa $V_L$ V/VI Front | CAT GCC ATG ACT CGC GGC GCG CCT | GAY ATY CAG ATG ACM CAG WCT AC |
| MPD VLF12 (SEQ ID NO: 58) | Mu kappa $V_L$ V/VI Front | CAT GCC ATG ACT CGC GGC GCG CCT | GAY ATY CAG ATG ACH CAG WCT CC |
| MPD VLF13 (SEQ ID NO: 59) | Mu kappa $V_L$ V/VI Front | CAT GCC ATG ACT CGC GGC GCG CCT | GAC ATT GTG ATG ACT CAG GCT AC |
| MPD VLF14 (SEQ ID NO: 60) | Mu lambda $V_L$ 1 Front | CAT GCC ATG ACT CGC GGC GCG CCT | CAR SYT GTK STS ACT CAG KAA T |
| MPD VLF15 (SEQ ID NO: 61) | Mu lambda $V_L$ 1 Front | CAT GCC ATG ACT CGC GGC GCG CCT | CAR SYT GTK STS ACT CAG KCA T |
| MPD VHB1 (SEQ ID NO: 62) | Mu $V_H$ $J_H$ 1 Back | CTA GTG GTA CTC CAC GGC CGG CCC CTG | MRG AGA CDG TGA SMG TRG TC |
| MPD VHB2 (SEQ ID NO: 63) | Mu $V_H$ $J_H$ 2 Back | CTA GTG GTA CTC CAC GGC CGG CCC CTG | MRG AGA CDG TGA SRG TRG TG |

TABLE 4-continued

Primers used for amplifying murine V$_H$ and V$_L$ antibody domains for scFv generation. These primers were used for cloning of scFvs prior to phage display as well as for cloning scFvs from preexisting hybridoma cell lines ("hybridoma rescue"). The specificity of all primers according to the Kabat-database (Kabat: "Sequences of immunological interest", 1991) is listed, all primers contain a 5'-noncoding 10 bp overhang to faciliate restriction enzyme digestion and cloning. For cloning V$_H$-fragments restriction enzymes Sfi I, Fse I, for cloning V$_L$-fragments restriction enzymes Asc I/ Not I were used.

| Name | Specificity according to Kabat (1991) | Overhang/Enzyme Region | Annealing region |
|---|---|---|---|
| MPD VHB3 (SEQ ID NO: 64) | Mu V$_H$ J$_H$ 3 Back | CTA GTG GTA CTC CAC GGC CGG CCC CTG | MRG AGA CDG TGA SCA GRG TC |
| MPD VHB4 (SEQ ID NO: 65) | Mu V$_H$ J$_H$ 4 Back | CTA GTG GTA CTC CAC GGC CGG CCC CTG | MRG AGA CDG TGA STG AGG TT |
| MPD VHB5 (SEQ ID NO: 66) | Mu V$_H$ J$_H$ 4 Back | CTA GTG GTA CTC CAC GGC CGG CCC CTG | MRG AGA CDG TGA STG ARA TT |
| MPD VLB1 (SEQ ID NO: 67) | Mu kappa V$_L$ I/II/IV back | CT AGT GGT ACT CCA CGC GGC CGC GTC GAC | AGC MCG TTT CAG YTC CAR YTT |
| MPD VLB2 (SEQ ID NO: 68) | Mu kappa V$_L$ I/II/IV back | CT AGT GGT ACT CCA CGC GGC CGC GTC GAC | AGC MCG TTT KAT YTC CAR YTT |
| MPD VLB3 (SEQ ID NO: 69) | Mu kappa V$_L$ IV back | CT AGT GGT ACT CCA CGC GGC CGC GTC GAC | AGC MCG TTT BAK YTC TAT CTT TGT |
| MPD VLB4 (SEQ ID NO: 70) | Mu kappa V$_L$ I/II/V back | CT AGT GGT ACT CCA CGC GGC CGC GTC GAC | AGC MCG AGC MCG TTT TAT TTC CAA MKT |
| MPD VLB5 (SEQ ID NO: 71) | Mu lambda V$_L$ back | CT AGT GGT ACT CCA CGC GGC CGC GTC GAC | CTG RCC TAG GAC AGT SAS YTT GGT |

Example 6

Enhanced Resistance by the Expression of Antibodies Against the Tobacco Mosaic Virus Replicase Expression of Antibodies Against the TMV 54K/TMV 183K Replicase Subunits in Transgenic Tobacco The steps 1) to 16) of example 1 and/or the steps 1) to 2) of example 2 are repeated with the following adaptations:
1) Specific antibodies recognising the TMV 54K/183K replicase are raised by hybridoma and phage display or ribosome technology by using recombinant TMV 54K/ TMV 183K proteins as the antigen and cloned to engineer single chain antibody fragments or any recombinant form thereof including bispecific scFvs.
2) These antibodies are expressed in the cytosol or targeted to cytoplasmic face of intracellular membranes, where the virus replication complexes are formed, by using a C-terminal sequence as described in example 2. The recombinant antibody may cause the desired biological effect without a fusion to a toxin.
3) For ELISA and surface plasmon resonance the test antigen for antibody function is the native or the recombinant TMV 54K and 183K replicase proteins or domains thereof.
4) Additionally to the bioassays listed in example 1, generated transgenic plants will be tested for broad spectrum resistance against different viral strains or viral genera by inoculation of transgenic plants with virions or infectious transcripts.

Anyone of skill in the art will recognise that these steps can be followed for any other viral pathogen by selecting antibodies or fragments thereof specific for the movement protein and any functional domain. Moreover, example 6 can be combined with examples 1–5 and 7–8 in any combination(s).

Anti-replicase Specific scFv (scFv 54K)

An alternative method to prevent viral infection is based on the intracellular expression of antibodies such as replicase specific scFvs which can interact with the viral replicase to interfere or inhibit viral proliferation in infected cells. As described in example 5 for the 30K movement protein the "54K protein" of TMV, was expressed in E. coli and antibodies were generated using standard hybridoma technologies available to anyone skilled in the art. The 54K protein can be considered as an integrative component of the 183K protein, the major replicase protein of TMV, since it is expressed from its own subgenomic RNA and promoter but it shares the same reading frame of the last 1400 bases of the 183K protein. Herein conserved regions such as the GDD-Motif are encoded which can be found in all plant viral replicases. Antibody V$_H$ and V$_L$ regions were cloned from hybridomas using the same set of primers described in example 5 and assembled into scFv antibodies using standard cloning procedures (Krebber et al. (1997), J. Immunol. Methods 201, 35–55). The activity of the resulting scFv antibody scFv 54-1 (FIG. 23a) was monitored by western blot detection and ELISA using the bacterial expressed GST-54K. The epitope of the scFv 54-1 was determined by peptide display (FIG. 25b) and could be mapped to a distinct region on the 54K/183K gene of TMV.

Plant Virus Minimal Proteins

Alternative viral proteins for engineering viral resistance are the "plant viral minimal proteins" 1 min, 2 min and 3 min as decribed for PLRV. One characteristic of the minimal-protein 3 min is its ability to bind to nucleic acids wherby preferentially single stranded RNA is bound (FIG. 24) (Prüfer et al., (1992) EMBO Journal 11, 1111–1117). 3 min-specific antibodies were generated by hybridoma technology using bacterial expressed GST-3 min as antigen and the antibody scFv 3 min was cloned from hybridoma cells (FIG. 23c). Since the 3 min protein of PLRV is described as a nucleic-acid binding protein the native structure of the bacterial expressed GST-3 min could be confirmed by nucleic acid binding assays using GST 3 min and in vitro transcripts of viral RNA and DNA. Using the antibody scFv 3 min the RNA/DNA binding activity of the 3 min protein could be completely blocked in vitro. Using epitope mapping by peptide display the epitope of the antibody could be mapped to a distinct region on the 3 min minimal protein wherby the epitope identified by peptide display overlapped with the GST cloning region of the GST-3 min construct (FIG. 25c).

Epitopemapping of Antiviral scFvs (scFv 29. 3 min and 54 K-1)

For elucidation of viral epitopes recognised by the developed recombinant antibodies two peptide display libraries were used for epitope mapping of monoclonal antibodies (Cortese et al. (1995), Curr. Opin. Biotechnol. 6, 73–80). Both libraries express 9mer random peptides at the N-terminus of filamentous phage pVIII protein. One library displays the peptides in linear form, the other library displays the peptides flanked by two Cysteine-residues which form a disulfide-bridge, constraining the peptide to a loop structure.

To identify the epitopes of scFv 29, scFv 54-1, and scFv 3 min immunotubes were coated using 20 µg affinity purified antigen using a standard procedure available to anyone skilled in the art (Cortese et al., (1995) Curr. Opin. Biotechnol. 6, 73–80). For the first round of panning, $5 \times 10^{12}$ phages in 1 ml PBS were incubated with the immobilized antigen (16 h, 4° C.). After extensive washing (15 times PBST and 5 times PBS), bound phages were eluted with 1 ml Glycine-HCl pH 2.2, 0.1% (w/v) BSA (10 min, 20° C.), neutralized with 60 µl 2M Tris and used for infection of E. coli. The titer of eluted phages was determined by plating 100 Ill of the infected bacteria on 2×TY-Amp-plates and counting the colony forming units. Enrichment factors were calculated upon comparison to a control panning using BSA as antigen. Monoclonal phages from the third round of panning were tested for reactivity to their antigens by phage-ELISA.

Positively identified phages from phage ELISA, using both phage libraries individually on all scFvs, were subsequentely sequenced. Obtained sequences were aligned and the resulting consensus sequence was determined. In all three cases (scFv 29, scFv 54-1 and scFv 3 min) a consensus sequence could be determined (FIG. 25). The resulting consensus sequence could also be mapped back to the parental sequence of the antigen the antibodies were generated against. Since the 9 mer random peptide library presents preferentially linear peptides it is considered that all three epitopes of the scFvs represent a linear motif on the antigen. The epitope of scFv29, scFv54-1 and scFv3 min were determined by peptide display and a consensus sequence was mapped for each scFv (FIG. 25). For the scFv29, the consensus sequence was mapped to a distinct region of the coat protein (FIG. 25a) land the scFv54-1 consensus sequence was mapped to a distinct region of the TMV 54K protein (FIG. 25b). For the scFv3 min the consensus sequence contained part of the GST and 3 min proteins (FIG. 25c) at the point where the 3 min was fused to the GST. ScFv3 min can be considered useful for engineering virus resistance as it inhibits the nucleic acid binding activity of the 3 min protein (FIG. 24).

Example 7

In Vivo Assembly of a Molecular Pathogenicide

In Vivo Assembly of a Molecular Pathogenicide Consisting of a TMV Specific Antibody Labelled with an Epitope Specific Single Chain Antibody and an Epitome Tag Labelled Toxin The following steps are taken:

1) Antibodies are generated against intact TMV virions and monoclonals are generated by hybridoma technology.
2) Hybridoma cell lines are cloned and cDNA sequences encoding the antibody variable regions are cloned to generate a single chain antibody or any recombinant version thereof binding to the TMV vidons (scFv24).
3) The single chain antibody binding to the intact virions (scFv24) is fused to a cloned cDNA from the single chain antibody (scFv-epitag29), which binds to a specific amino acid epitope (epitag29), using a flexible linker such as the linker peptide of Trichoderma reesi cellobiohydrolase I (CBHI) to generate a recombinant protein which recognises the pathogen, TMV, and the epitope tag. The scFv-epitag29 has been previously generated (by conventional hybridoma technology and then cloned as an scFv) and the specific epitope identified by phage peptide display. Any other high affinity antibody recognising an identified peptide epitope would be suitable as one half of the binding pair with its corresponding epitope as the other partner.
4) The recombinant gene from step 3 is inserted in a microbial or eukaryotic expression vector.
5) The binding specificity and function (i.e. specificity and affinity) of the recombinant protein from step 3 is checked after expression in a heterologous host; such as in the periplasm of E.coli.
6) A signal sequence is added to the N-terminus of the recombinant bispecific scFv construct from step 3, to permit delivery of the protein to the ER and secretion to the apoplast upon expression in plants. A 5' untranslated and a 3' untranslated region and a detection tag sequence (i.e. c-myc) will be introduced by recombinant DNA technology, if necessary.
7) The chimeric gene from step 6 is inserted into a plant expression vector, e.g. pSS (Voss et al., 1995). Suitable plant expression vectors include suitable promoter, enhancer, terminator and selection marker sequences. In case of markerless and vectorless gene transfer selection marker sequences can be omitted.
8) The cDNA encoding a RIP (ribosome inactivating protein) fused via a suitable linker to the epitag-29 epitope tag (either at the N- or C-terminus), which is specifically recognised by scFv-epitag29, is prepared in parallel to generate a second independent expression construct encoding a tagged RIP gene.
9) The tagged RIP gene is inserted in a microbial or eukaryotic expression vector and the functionality of the RIP-epitope fusion is checked upon expression in a heterologous host.
10) A second, independent plant expression vector, such as pSS, containing the recombinant tagged RIP gene with an N-terminal signal peptide will be prepared, as described in step 6 and step 7. The tagged RIP sequence can then be integrated either in tandem array on the same plasmid as the fusion protein from step 3 or integrated in a second independent plasmid. Note that the sequences remain discrete even if they are in tandem array.
11) Both plant expression constructs listed in steps 6 and 10 are transformed into two independent plant lines or they are co-transformed into the same plant genome, or if the antibody fusion protein from step 3 and the tagged toxin from step 10 are integrated in tandem array that construct is transformed into the same plants.
12) Regenerated plants are screened using the selection marker for integration of the fusion gene in the independent plant lines or the co-transformed lines from step 11.
13) Transgenic plants that express only one of either the antibody fusion protein from step 3 or epitope tagged RIP from step 10 are then sexually crossed to give offspring which will produce both proteins. Plants producing both proteins, whether from this or earlier steps, will produce assembled protein complexes were the two binding partners, the epitope specific antibody (scFv-epitag29) and the epitope bind and permit assembly of a molecular pathogenicide protein complex.
14) Expression of the bispecific scFv fusion protein and/or the tagged RIP as well as the in vivo assembled molecular pathogenicide is monitored by western blotting cell extracts, ELISA or surface plasmon resonance analysis. Activity of the bispecific scFv is checked by ELISA using intact TMV virions as the antigen.
15) Activity of the assembled molecular pathogenicide is checked by ELISA and cytotoxicity assays.
16) Localisation of the fusion protein is checked by indirect immuno-fluorescence, confocal microscopy or immuno-electron microscopy and western blotting or ELISA or surface plasmon resonanace analysis of the intercellular washing fluid.
17) The biological activity of the in vivo assembled molecular pathogenicide against TMV is assayed by bioassays on the generated transgenic plants using virions or infectious transcripts.

Anyone of skill in the art will recognise that these steps can be followed for any other pathogen by selecting antibodies or fragments thereof specific for the target pathogen. For example, antibodies can be raised and cloned against structural and non structural proteins of any pathogen. Instead of RIPs, similar toxins with cell killing activity or interference in pathogenicity (RNAase, DNase etc.) can be used. Assembly of molecular pathogenicides can be achieved by using any epitope tag and a given epitope specific antibody with a suitable and stable molecular interaction in vivo, or any other pair of proteins that bind to each other. Moreover, example 7 can be combined with examples 1–6 and 8 in any combination(s).

Constructs for Analysing Assembly of Fusion Partners

To analyse assembly of a molecular pathogenicide consisting of a TMV specific antibody labelled with an epitope specific single chain antibody and an epitope tag labelled toxin different constructs were generated and assembly was studied by immunoblot and ELISA.

TMV specific antibody labelled with an epitope specific single chain antibody (biscFv2429): The single chain antibody binding to the intact virions (scFv24) was fused to a cloned cDNA from the single chain antibody scFv-epitag29, which binds to a specific amino acid epitope (epitag29), using the flexible linker peptide of *Trichoderma reesi* cellobiohydrolase I (CBHI) to generate a recombinant protein which recognises the pathogen, TMV, and the epitope tag. The scFv-epitag29 has been previously generated (by convential hybridoma technology and then cloned as an scFv) as described for the scFv24 (Schillberg et al., *Transgenic Research* 8, 255–263 (1999)) and the specific epitope identified by phage peptide display. The mouse N-terminal light chain signal peptide from the original antibody (mAb24) used to generate scFv24 was used to target biscFv2429 to the secretory pathway. For expression in plant cells, the 5' UT from the chalcone synthase was introduced and the cassette was inserted between the enhanced 35S promoter and the CaMV termination sequence in the pSS expression vector (FIG. 26) (Fischer et al., *Eur. J. Biochem.* 262, 810–816 (1999)).

Epitope tag labelled toxin (PE280-tag29 and PE400-tag29): Two constructs were generated containing parts of the Pseudomonas exotoxin (PE) and the C-terminal epitag-29 fused via a Gly$_4$Ser linker. The construct PE280-tag29 (FIG. 26B) contains the sequence from amino acid (aa) 280 to aa 609, which comprises domain II and domain III from PE. The construct PE400-tag29 (FIG. 26C) contains PE domain III from aa 400 to aa 609. PE domain III mediates the ADP-ribosylation of elongation factor 2, which arrests the protein synthesis and causes cell death. The epitag-29, which is specifically recognised by scFv-epitag29, was fused C-terminal to both constructs via Gly$_4$Ser linker. The mouse N-terminal light chain signal peptide from the murine monoclonal antibody mAb24 was used to target PE280-tag29 and PE400-tag29 to the secretory pathway.

The PE280 and PE400 were PCR amplified from the plasmid PE38 using the following primers: for PE280: PE280-for 5'-GCG GAA TC GAC GTC GCC ATG GGC TGG GAA CAA CTG GAG CAG-3' SEQ ID NO:157) and PE-back 5'-GCG AMG CTT GTC GAC CGG CGG UT GCC GGG CTG GCT G-3'(SEQ ID NO:158); for PE400: PE400-for 5'-GCG GAATC GAC GTC GCC ATG GCC UTC CTC GGC GAC GGC GGC GAC-3' SEQ ID NO:159) and PE-back 5'-GCG AAG CTT GTC GAC CGG CGG UT1 GCC GGG CTG GCT G-3' SEQ ID NO:160). The primers contained restriction sites EcoRI, AatII and NcoI (PE280-for and PE400-for) and and HindIII (PE-back) for cloning. The PCR fragments were subcloned via EcoRI and HindIII into pUC18 resulting in the constructs PE280- and PE400-intermediate and the sequence was verified by sequencing. The NcoI/SalI fragment from both constructs (PE280- and PE400-intermediate) was subcloned into a pUC18 derivate containing the chalcone synthase 5' untranslated region, the codon optimized leader signal from mAb24 light chain and the C-terminal epitope tag29 resulting in the constructs PE280-tag29 and PE400-tag29. For expression in plant cells, the EcoRI/XbaI fragments (FIG. 26) of PE280-tag29 and PE400-tag29 were subcloned into the EcoRI and XbaI restriction sites of the plant expression vector pSS (Voss et al., *Molecular Breeding* 1: 39–50 (1995)) containing the enhanced 35S promoter (Kay et al., *Science* 236: 1299–1302 (1987)) and the CaMV termination sequence (FIGS. 26B and C).

Control construct, epitope tag labelled GST (GST-tag29): To analyse the assembly of the epitag29 and the corresponding antibody, the control construct GST-tag29 was generated by introducing the epitag-29 sequence into the pGEX-5X-3 vector (Pharmacia) at the C-terminus of GST.

Analysis of GST-tag29

The epitag-29 is specifically recognised by scFv-epitag29 and the corresponding recombinant full-size antibody mAb29 or its recombinant version rAb29. To analyse the binding specificity of rAb29 to epitag-29, affinity purified, bacterial expressed GST-tag29 was diluted either in PBS or in protein extract of a wild type *N. tabacum* cv. Petite Havana SR1 plant and serial dilutions were seperated on a SDS-PAA gel and blotted onto a nitrocellulose membrane.

The recombinant plasmid GST-tag29 was transformed into *E. coli* BL21 (DE3) (Stratagene, La Jolla. Calif., USA) and the fusion protein was expressed by inducing a log phase culture with 0.2–1.0 mM IPTG for 1–3 h at 30° C. GST-tag29 fusion protein was affinity purified on glutathione agarose by batch purification according to the manufacturer's instructions (Pharmacia). Serial dilutions of GST-tag29 were resolved by SDS-PAGE and blotted onto Hybond™-C nitrocellulose membranes (Amersham, Braunschweig, Germany). The membranes were blocked overnight with 2% non-fat skim milk in PBS (MPBS) at 4° C. followed by incubation with rAb29 (Schillberg, et al., *Transgenic Research* 8, 255–263 (1999)) at room temperature for 2 h. Bound antibodies were detected using goat anti-mouse IgG conjugated to alkaline phosphatase (Jackson ImmunoResearch, West Grove, Pa., USA) and the substrates p-nitrobluetetrazolium chloride (NBT) and 5-bromo-4-chloro-3-indolyl phosphate (BCIP).

Figure 27A:
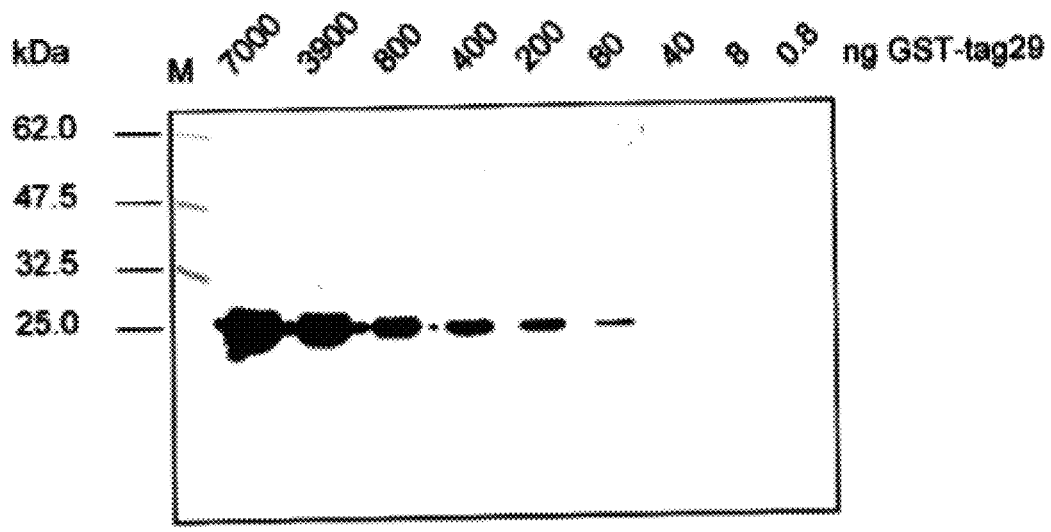
Figure 27B:
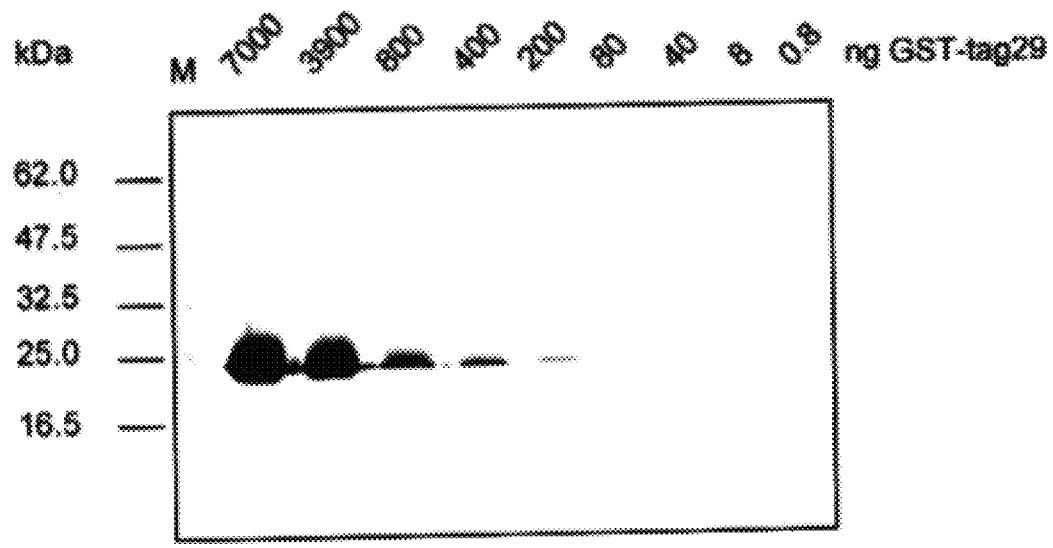

As shown in FIG. 27A, 80 ng GST-tag29 in PBS was detectable using rAb29. Although in tobacco extract the detection limit decreased to 200 ng GST-tag29 (FIG. 27B), this result indicates that plant derived proteins did not prevent binding of rAb29 to the epitag-29.

The in vivo assembly in a plant cell was simulated by ELISA, in which the scFv-epitag29 bound to epitop-29. As shown in FIG. 28, a significant OD reactivity was detectable, indicating that binding of the two partners took place in plant extracts.

Transient Expression in Tobacco Leaves

To analyze the protein level of the recombinant PE280-tag29, N. tabacum cv. Petite Havana SR1 leaves were transiently transformed with recombinant A. tumefaciens and accumulation of PE280-tag29 was analyzed by immunoblot.

Plant expression construct PE280-tag29 was transferred into A. tumefaciens GV3101 by $N_2$ transformation (Höfgen and Willmitzer, Nucleic Acids Res 16 (1988) 9877). Transient transformation of N. tabacum cv. Petite Havana SR1 was performed as described (Kapila et al., Plant Science 122 (1996) 101–108). To extract total soluble proteins, Tobacco leaves were frozen and ground in liquid nitrogen and scFv-fusion protein level was analysed by Western blot (Fischer et al., in: C. Cunningham, A. J. R. Porter, (Eds.), Methods in biotechnology Vol. 3: Recombinant proteins in plants: Production and Isolation of Clinically useful compounds. Humana Press, Totowa, N.J. (1998)).

A protein of the expected size (37.1 kDa) was not detectable in plant extracts (FIG. 29). However a degradation product was detectable, indicating that the recombinant PE280-tag29 protein accumulated in tobacco leaves. The plant leaves showed a healthy phenotype, indicating that PE280-tag29 was most likely secreted to the apoplast and therefore not toxic to the plant cell.

Characterization of Transgenic Plants

N. tabucum cv. Petite Havana SR1 was transformed with the construct PE280-tag29 using recombinant agrobacteria. Transgenic N. tabacum cv. Petite Havana SR1 were generated by the leaf disc transformation with recombinant A. tumefaciens and transgenic $T_0$ plants were generated from transformed callus (Horsch et al., Science 227: 1229–1231 (1985)). Regeneration of transgenic plants is in progress.

In addition, transgenic N. tabucum cv. Petite Havana SR1 plants accumulating biscFv2429 in the apoplast will be retransformed with the plant expression construct PE280-tag29 to analyse in vivo assembly and biological effects of the molecular pathogenicide.

Conclusions

The Molecular Pathogenicide will be assembled in the ER via the scFv-epitag29 and epitag29. The presented experiments show that proteins can be assembled using scFv-epitag29 and epitag29 in plant extracts. Upon assembly the Molecular Pathogenicide will be secreted to the apoplast. During TMV infection the fusion protein will bind to the virus particle via the scFv24 part and TMV virions that enter the cell will carry bound scFv24-toxin fusion. PE400 mediates the ADP-ribosylation of elongation factor 2, which arrests protein synthesis and causes cell death. PE is a very effective toxin as only a few molecules are required to kill the infected cell, thus preventing virus replication and spread, leading to highly resistant plants.

Example 8

In Vivo Proteolysis

The steps 1) to 16) of example 1 and steps 1) to 2) example 2 are repeated with the following adaptations.
1) A protease cleavage sequence which is processed by a plant and/or a pathogen protease in vivo is added either between the recombinant scFv construct and the C-terminal membrane localisation sequence, using a suitable linker, or between an N-terminal toxin and a C-terminal membrane anchored recombinant antibody or vice versa.
2) The chimeric gene is inserted into a plant expression vector e.g. pSS (Voss et al., 1995).
3) Suitable protease cleavage sequences include a selected sequence from a random linker library (Doskeland, Biochem. J. 313 (1996), 409–414) that had been selected by in vitro proteolysis and any known protease site that is unique to the fusion protein and does not destroy the molecular viricide and its activity in vivo. As an example, the c-myc tag or the CBHI linker is sensitive to plant proteases.

Anyone of skill in the art will recognise that these steps can be followed for any other pathogen by selecting antibodies or fragments thereof specific for the target pathogen. For example, antibodies can be raised and cloned against structural and non structural proteins of any pathogen. In addition, toxins can be cloned C- or N-terminal of the protease cleavage sequence. Toxins include all proteins and peptides that have a detrimental or toxic effect on a pathogen during its life cycle and/or an effect on the pathogen during plant infection or pathogen replication, spread or transmission. This includes toxins that specifically kill an infected host cell and so limit the spread and development of a disease. Moreover, example 8 can be combined with examples 1–7 in any combination(s).

Construction of the scFv24 Fusion Expression Cassettes

To integrate the TMV-specific scFv24 into the plant cell membrane, the antibody fragment was fused to an N-terminal mammalian signal peptide and C-terminal receptor transmembrane domain. The mouse N-terminal light chain signal peptide from the parental antibody (mAb24) used to generate scFv24 was used to target fusion proteins to the secretory pathway. We selected the transmembrane domain sequences of the human platelet derived growth factor receptor (PDGFR) for fusion with the C-terminus of scFv24, for heterologous targeting of the scFv24 antibody to the plasma membrane. To ensure proper folding of the expressed and subsequent cleaved single chain antibody fragment, the construct contained the c-myc sequence (pscFv24-PDGFR) as a linker and cleavage sequence between the scFv24 fragment and the membrane anchor (FIG. 30).

To construct pscFv24-PDGFR, the cDNA encoding the c-myc epitope followed by the human platelet-derived growth factor receptor (PDGFR) transmembrane domain (18) was excised from the pHOOK-1 vector (Invitrogen, Leek, Netherlands) and ligated into the SalI and XbaI restriction sites of the pscFv24-TcRβ plasmid (Example 1) to generate the pscFv24-PDGFR fusion construct (FIG. 30).

Expression of the scFv24 Fusion Protein in N. tabacum cv. BY-2 Cell Suspensions

To analyze the expression level of the recombinant scFv-fusion proteins, the suspension cell line N. tabacum cv. BY-2 was stably transformed with recombinant A. tumefaciens and functional expression of the scFv24 domain of the fusion protein was analyzed by ELISA using anti-mAb24 antisera.

The vector construct pscFv24-PDGFR was transferred into *A. tumefaciens* GV3101 by liquid $N_2$ transformation (H öfgen and Willmitzer, Nucleic Acids Res. 16: 9877 (1988)). *N. tabacum* L. cv. bright yellow 2 (BY-2) cells were maintained in Murashige and Skoog basal salt with minimal organics (MSMO+: MSMO (Sigma, Deisenhofen, Germany) plus 200 mg/ml $KH_2PO_4$, 0.6 µg/ml thiamine, 3% sucrose and 0.2 µg/ml 2,4-D, pH 5.8) at 24° C. in the dark on an orbital shaker. Cells were subcultured every week with a 5% inoculum. Three days after subculture, plant cells were transformed by co-cultivation with recombinant *A. tumefaciens*, as described (An, Plant Physiol. 79: 568–570 (1985)). Selection of kanamycin-resistant transformants was performed on MSMO+ agar medium supplemented with 75 µg/ml kanamycin and 100 µg/ml clafaran.

For extraction of total soluble proteins from transgenic BY-2 suspension culture, cells from 1 ml culture were collected by centrifugation at 4000×g for 5 mn at 4° C. The cell pellet was resuspended in 1 ml protein extraction buffer (200 mM Tris-HCl (pH 7.5), 5 mM EDTA, 0.02% (w/v) sodium-azide and 0.1% (v/v) Tween 20) and cells were disrupted by sonication at 60 waft for 1 min using a sonicator probe (B. Braun, Melsung en, Germany) at 4° C. Cell debris was removed by centrifugation at 14000×g for 10 min at 4° C. The clear supernatant containing soluble protein was used for further analysis.

For ELISA and western blotting, anti-mAb24 antisera (Zimmermann et al., Molecular Breeding 4: 369–379 (1998)) or the anti-c-myc monoclonal antibody 9E10 (Evan et al., Mol. Cell. Biol. 5: 3610–3616 (1985)) were used a s a primary antibody in combination with a 1:5000 dilution of goat anti-rabbit or goat anti-mouse alkaline phosphatase conjugated secondary antibodies (Jackson Immuno Research Laboratories, West Grove, Pa). Protein concentrations were determined with the Bio-Rad Protein Assay using Bovine Serum Albumin (BSA) as standard.

Analysis of stably transformed *N. tabacum* BY-2 cells revealed that scFv24-PDGFR was present in both cell extracts and culture supernatant (FIG. 31). Transgenic cell suspension lines showed similar expression levels for both recombinant proteins, but 44–88% (mean value=69%, n=5) of scFv24-PDGFR was secreted into the culture supernatant. This indicated that the scFv:24-PDGFR is released by proteolysis from the plasma membrane.

Characterization of Transgenic Giants

We then tested whether the heterologous mammalian transmembrane domain PDGFR fused to scFv24 would target the s ingle chain antibody to the plasma membrane in stably transformed tobacco, plants. Transgenic *N. tabacum* cv. Petite Havana SR1 were generated by the leaf disc transformation with recombinant *A. tumefaciens* and transgenic To plant s were generated from transformed callus (Horsch et al., Science 227: 1229–1231 (1985)a. Extraction of total soluble proteins from tobacco leaves and subsequent analysis of scFv24 by ELISA we re performed as described by Fischer et al. (Fischer et al., in: Cunningham C, Porter A J R (eds), Recombinant proteins in plants: Production and Isolation of Clinically useful compounds, pp. 45–68. Vol. 3. Humana press, Totowa, N.J. (1998)). For ELISA and western blotting, anti-mAb24 antisera (Zimmermann et al., Molecular Breeding 4: 369–379 (1998)) was used as a primary antibody in combination with a 1:5000 dilution of goat anti-rabbit alkaline phosphatase conjugated secondary antibodies (Jackson Immuno Research Laboratories, West Grove, Pa.). Protein concentrations were determined with the Bio-Rad Protein Assay using Bovine Serum Albumin (BSA) as a standard.

Expression levels of scFv24-PDGFR were much higher in transgenic *N. tabacum* cv. Petite Havana SR1 plants than in suspension cultures (Table 5). The maximum level of detergent extracted scFv24-PDGFR was 13 fold higher (388 ng/g leaf tissue) than that obtained in transgenic suspension cultures (FIG. 31).

In *N. tabacum* cv. BY-2 suspension cells producing the scFv24-PDGFR fusion protein, scFv24 was detectable in the culture supernatant. To determine if scFv24 fragments were secreted into the extracellular space of intact plants, intercellular washing fluid from leaves of transgenic $T_1$ tobacco plants was analyzed by ELISA. For detection of scFv24 fusion proteins in intercellular washing fluids, leaves of *N. tabacum* cv. Petite Havana SR1 were prepared as described by Fischer et al. (Fischer et al., in: Cunningham C, Porter A J R (ads), Recombinant proteins in plants: Production and Isolation of Clinically useful compounds, pp. 45–68. Vol. 3. Humana press, Totowa, N.J. (1998)). Total protein extracts from washing fluids were concentrated by ultrafiltration (Microcon 10, Amicon, Witten, Germany) and analyzed by 12% SDS-PAGE (Laemmli, Nature 227: 680–685 (1970)) followed by western blot. scFv24 was present in the intercellular washing fluid of seven progenies of a plant line ($P9_{SR1}$) producing scFv24-PDGFR and the level of secreted scFv24 did not correlate to levels of protein expression in intact leaves. In general, $T_1$ plants used for IWF analysis showed scFv24 expression levels of 1080–1540 ng/g leaf tissue. Therefore, the protein is cleaved by a host protease.

Figure 32A:
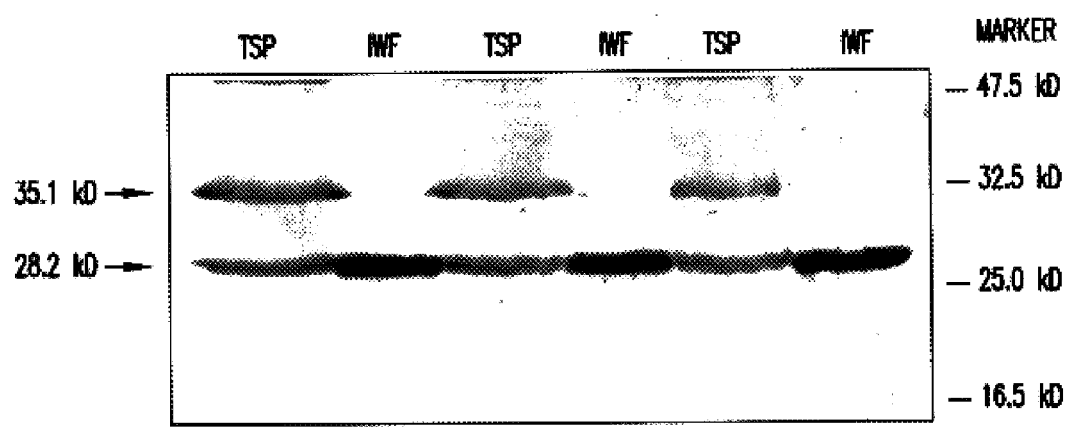
Figure 32B:
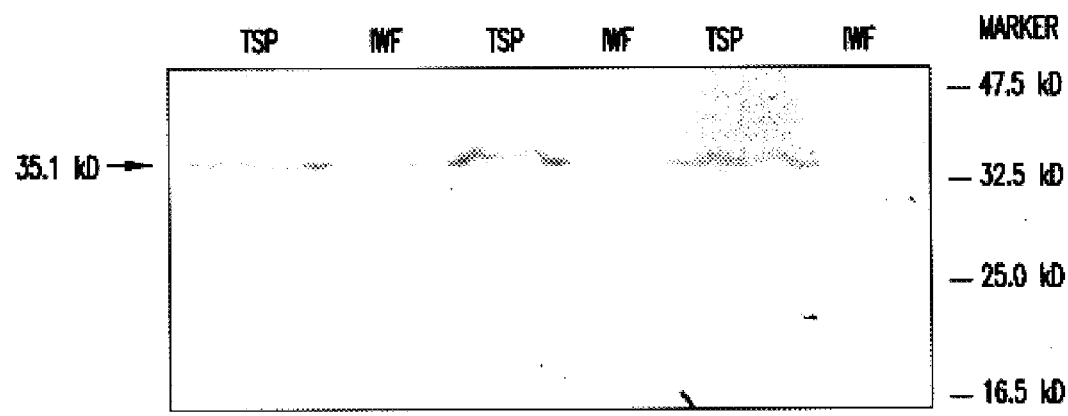

Western blot analysis, using an anti-mAb24 antisera, revealed that a single 28 kDa scFv24 polypeptide was detected in the intercellular washing fluid of $T_1$ progenies from scFv24-PDGFR transgenics ($P9_{SR1}$). This corresponded to a fusion protein cleavage product since the predicted molecular weight of scFv24-PDGFR was 35 KDa. However, both the full length (35 KDa) and cleaved (28 KDa) fragments of scFv24 were present in total soluble cell protein extracts at a 1:1 ratio of full-length product to the fragment (FIG. 32A). Western blot analysis of total soluble protein extracts with an anti c-myc antibody only detected the intact fusion protein scFv24-PDGFR (FIG. 32B). This indicates that the scFv24 fragment in the apoplast was cleaved off the membrane near or within the c-myc epitopSe tag.

Bioassays of Viral Resistance

To analyze the biological effects of the membrane anchored anti-viral TMV-specific antibody on viral resistance, $T_1$ progenies of plant line expressing the scFv24-PDGFR fusion protein ($P9_{SR1}$) were inoculated with TMV. Seeds were collected from antibody-producing $T_0$ plants and germinated on MSMO agar medium supplemented with 2% (w/v) sucrose, 0.4 µg/ml thiamine, 0.4 µg/ml glycine, 0.1 µg/ml nicotine acid, 0.1 pg/ml pyridoxine and 75 µg/ml kanamycin. Kanamycin-resistant $T_1$ plants were used for inoculation with TMV-v (1 µg/ml) as previously described (Dietzgen et al., Arch. Virol. 87: 73–86 (1986)). Wild type *N. tabacum* cv. Petite Havana SR1 plants were used as a control. Disease symptoms were monitored 6 to 20 days post inoculation (p.i.) and for resistant plants up to 180 days p.i.

Lower leaves were infected with TMV and systemic spread of the virus was followed by analyzing upper leaves 6–20 days later. All non-transgenic tobacco control plants were systemically infected, but 19% (out of 68 analyzed) of scFv24-PDGFR transgenic plants had no visible disease symptoms on the upper leaves (Table 6). Furthermore, ELISA analysis demonstrated that some of these plants accumulated virus particles in the upper leaves indicating that though systemic viral spread occurred, no symptoms were developed. Strikingly, in 13% of scFv24-PDGFR transgenic plants no virus was found in the upper leaves up to 90 days post inoculation. Virus could be detected at inoculation sites in the lower leaves by ELISA demonstrating that these plants had been efficiently inoculated with TMV. Antibody-fusion protein expression levels correlated with expression of TMV resistance (Table 6). Higher levels of scFv24 fusion protein expression led to an increased fraction of virus resistant plants.

Conclusions

It could be shown that the linker region between the scFv24 and the PDGFR transmembrane domain is sensitive to plant proteases, the scFv24 is cleaved off in vivo and secreted to the apoplast in transgenic plants. scFv24 retains its function post cleavage and creates a virus resistant phenotype.

TABLE 5

Levels of functional scFv24 fusion protein in the $T_0$ generation of transgenic *N. tabacum* cv. Petite Havanna SR1.
Total soluble plant protein was isolated from leaves of transgenic plants producing scFv24-PDGFR. scFv24-fusion protein expression was quantified by TMV-specific ELISA using anti-mAb24 antisera and expressed as ng scFv24 per g leaf tissue.

| Construct | Number of transgenic plants | Number of plants expressing functional scFv24 | Range of expression (ng/g leaf tissue) | Average expression (ng/g leaf tissue) |
|---|---|---|---|---|
| pscFv24-PDGFR | 12 | 9 | 3–388 | 114 |

TABLE 6

Virus infection assay of trangenic plants expressing membrane anchored scFv24. 1 μg/ml TMV-v was applied onto a lower leaf of non-transgenic *N. tabacum* cv. Petite Havana SR1 and transgenic $T_1$ progenies from plant line $P9_{SR1}$ producing scFv24-PDGFR. scFv24-fusion protein levels were determined by ELISA using an anti-mAb24 antisera 14 days p.i. and used for group formation (low, average and high producers).

| Plant lines | Tested plants | ng scFv24 per g leaf tissue | Healthy phenotype[a] | Resistant plants[b] | Level of resistance (%)[c] |
|---|---|---|---|---|---|
| *N. tabacum* cv. Petite Havana SR1 | 62 | — | 0 | 0 | 0 |
| $P9_{SR1}$, low producer | 34 | 10–500 | 1 | 0 | |
| $P9_{SR1}$, average producer | 23 | 501–2000 | 6 | 4 | 13(19) |
| $P9_{SR1}$, high producer | 11 | 2001–4200 | 6 | 5 | |

[a] = upper leaves showed no visible disease symptoms;
[b] = based on TMV-ELISA;
[c] = level of resistance of all low, average and high producers, numbers in brackets include all plants without visible disease symptoms.

References

Anderson, J. M., P. Palukaitis, and M. Zaitlin. 1992. A defective replicase gene induces resistance to cucumber mosaic virus in transgenic sugarbeet plants. Proc. Natl. Acad. Sci. USA. 89:8759–8763.

Barbieri, L., M. G. Battelli, and F. Stirpe. 1993. Ribosome-inactivating proteins from plants. Biochim Biophys Acta. 1154:237–282.

Baulcombe, D. 1994. Novel strategies for engineering virus resistance in plants. Current Opinion in BioTechnology. 5:117–124.

Benfey, P., L. Ren, and N. -H. Chua. 1989. The CaMV 35S enhancer contains at least two domains which can confer different developmental and tissue-specific expression patterns. EMBO J. 8:2195–2202.

Bennett, A., and K. Osteryoung. 1991. Protein transport and targeting within the endomembrane system of plants. In Plant Genetic Engineering. Vol. 1. D. Grierson, editor. Blackie publishing, London. 199–237.

Benvenuto, E., R. J. Ordas, R. Tavazza, G. Ancora, S. Biocca, A. Cattaneo, and P. Galeffi. 1991. 'Phytoantibodies': a general vector for the expression of immunoglobulin domains in transgenic plants. Plant Mol Biol. 17:865–74.

Bird, R. E., K. D. Hardman, J. W. Jacobson, S. Johnson, B. M. Kaufmann, S.-M. Lee, T. Lee, H. S. Pope, G. S. Riordan, and M. Whitlow. 1988. Single-chain antigen-binding proteins. Science. 242:423–426.

Bjorck, L., P. Akesson, M. Bohus, J. Trojnar, M. Abrahamson, I. Olafsson, and A. Grubb. 1989. Bacterial growth blocked by a synthetic peptide based on the structure of a human proteinase inhibitor. Nature. 337:385–6.

Bjorck, L., A. Grubb, and L. Kjellen. 1990. Cystatin C, a human proteinase inhibitor, blocks replication of herpes simplex virus. Nature. 337:385–386.

Caddick, M., A. Greenland, I. Jepson, K. Krause, N. Qu, K. Riddell, M. Salter, W. Schuch, U. Sonnewald, and A. Tomsett. 1998. An ethanol inducible gene switch for plants used to manipulate carbon metabolism. Nat. Biotechnol. 16:177–180.

Carter, P., and A. Merchant. 1997. Engineering antibodies for imaging and therapy. Curr Opin Biotechnol. 8:449–454.

Carter, P., J. Ridgway, and Z. Zhu. 1995. Toward the production of bispecific antibody fragments for clinical applications. J Hematother. 4:463–470.

Chen, S. Y., Y. Khouri, J. Bagley, and W. A. Marasco. 1994. Combined intra- and extracellular immunisation against human immunodeficiency virus type 1 infection with a human anti-gp 120 antibody. Proc. Nati. Acad. Sci USA. 91:5932–5936.

Chowrira, G., V. Akella, and P. Lurquin. 1995. Electroporation-mediated gene transfer into intact nodal meristems in planta. Generating transgenic plants without in vitro tissue culture. Mol Biotechnol. 3:17–23.

Comai, L., P. Moran, and D. Maslyar. 1990. Novel and useful properties of a chimeric plant promoter combining CaMV 35S and MAS elements. Plant Mol. Biol. 15:373–381.

De Neve, M., M. De Loose, A. Jacobs, H. Van Houdt, B. Kaluza, U. Weidle, M. Van Montagu, and A. Depicker. 1993. Assembly of an antibody and its derived antibody fragment in Nicotiana and Arabidopsis. Transgenic Res. 2:227–37.

Dempsey, D., H. Silva, and D. Klessig. 1998. Engineering disease and pest resistance in plants. Trends Microbiol. 6:54–61.

D'Halluin, K., E. Bonne, M. Bossut, M. De Beuckeleer, and J. Leemans. 1992. Transgenic maize plants by tissue electroporation. Plant Cell. 4:1495–1505.

Duan, L., O. Bagasra, M. A. Laughlin, J. W. Oakes, and R. J. Pomerantz. 1994. Potent inhibition of human immunodeficiency virus type 1 replication by an intracellular anti-Rev single chain antibody. Proc. Natl. Acad. Sci USA. 91 :5075–5079.

Düring, K., S. Hippe, F. Kreuzaler, and J. Schell. 1990. Synthesis and selfassembly of a functional monoclonal antibody in transgenic *Nicotiana tabacum*. Plant Mol. Biol. 15:281–293.

Eiklid, K., S. Olsnes, and A. Pihl. 1980. Entry of lethal doses of abrin, ricin and modeccin into the cytosol of HeLa cells. Exp Cell Res. 126:321–6.

Endo, Y., and K. Tsurugi. 1987. RNA N-glycosidase activity of ricin A-chain. Mechanism of action of the toxic lectin ricin on eukaryotic ribosomes. J Biol Chem. 262:8128–30.

Endo, Y., and K. Tsurugi. 1988. The RNA N-glycosidase activity of ricin A-chain. Nucleic Acids Symp Ser. 19:139–42.

Falk, B. W., and G. Bruening. 1994. Will transgenic crops generate new viruses and new diseases. Science. 263:1395–1396.

Fiedler, U., J. Phillips, O. Artsaenko, and U. Conrad. 1997. Optimisation of scFv antibody production in transgenic plants. Immunotechnology. 3:205–216.

Fischer, R. S., A. Schillberg, Y.-D. Stierhof, and F. Kreuzaler. 1999. Production, characterisation and molecular cloning of Tobacco Mosaic Virus (TMV)-specific neutralizing monoclonal antibodies with different epitope specificities. Molecular Immunology.

Florack, D., W. Dirkse, B. Visser, F. Heidekamp, and W. Stiekema. 1994. Expression of biologically active hordothionins in tobacco. Effects of pre- and pro-sequences at the amino and carboxyl termini of the hordothionin precursor on mature protein expression and sorting. Plant Mol Biol. 24:83–96.

Friedler, A., N. Zakai, O. Karni, Y. Broder, L. Baraz, M. Kotler, A. Loyter, and C. Gilon. 1998. Backbone cyclic peptide, which mimics the nuclear localisation signal of human immunodeficiency virus type 1 matrix protein, inhibits nuclear import and virus production in nondividing cells. Biochemistry. 37:5616–5622.

Furth, P. 1997. Gene transfer by biolistic process. Mol Biotechnol. 7:139–143.

Gadani, F., M. Mansky, R. Medici, W. A. Miller, and J. H. Hill. 1990. Genetic engineering of plants for virus resistance. Archives of Virology. 115:1–21.

Gerber, L. D., K. Kodukula, and S. Udenfriend. 1992. Phosphatidylinositol glycan (PI-G) anchored membrane proteins. Amino acid requirements adjacent to the site of cleavage and PI-G attachment in the COOH-terminal signal peptide. J Biol Chem. 267:12168–73.

Girbes, T., J. Ferreras, R. Iglesias, L. Citores, C. De Torre, M. Carbajales, P. Jimenez, F. De Benito, and R. Munoz. 1996. Recent advances in the uses and applications of ribosome-inactivating proteins from plants. Cell Mol Biol (Noisy-le-grand). 42:461–471.

Gross, G., and Z. Eshhar. 1992. Endowing T cells with antibody specificity using chimeric T cell receptors. Faseb J. 6:3370–8.

Ham, P. J., C. Albuquerque, B. Smithies, R. Chalk, S. Klager, and H. Hagen. 1994. Antibacterial peptides in insect vectors of tropical parasitic disease. Ciba Found Symp. 186:140–51.

Harrison, B. D., M. -A. Mayo, and D. C. Baulcombe. 1987. Virus resistance in transgenic plants that express cucumber mosaic virus satellite RNA. Nature. 328:799–802.

Hartley, M. R., J. A. Chaddock, and M. S. Bonness. 1996. The structure and function of ribosome inactivating proteins. Trends in Plant Science. 1:254–260.

Hayakawa, Y. 1991. Structure of a growth-blocking peptide present in parasitzed insect hemolymph. J Biol Chem. 266:7982–7984.

Hiatt, A., R. Cafferkey, and K. Bowdish. 1989. Production of antibodies in plants. Nature. 342:469–470.

Kapila, J., R. De Rycke, M. Van Montagu, and G. Angenon. 1997. An Agrobacterium mediated transient gene expression system for intact leaves. Plant Sci. 122:101–108.

Kim, P., F. Janiak-Spens, W. Trimble, B. Leber, and D. Andrews. 1997. Evidence for multiple mechanisms for membrane binding and integration via carboxyl-terminal insertion sequences. Biochemistry. 36:8873–8882.

Klein, T., and S. Fitzpatrick-McElligott. 1993. Particle bombardment: a universal approach for genetransfer to cells and tissues. Curr Opin Biotechnol. 4:583–590.

Köhler, G., and C. Milstein. 1975. Continuous cultures of fused cells secreting antibody of predefined specificity. Nature. 256:495–497.

Lambert, S., and V. Bennett. 1993. From anemia to cerebellar dysfunction. A review of the ankyrin gene family. Eur J Biochem. 211:1–6.

LaVallie, E., E. DiBlasio, S. Kovacic, K. Grant, P. Schendel, and J. McCoy. 1993. A thioredoxin gene fusion expression system that circumvents inclusion body formation in the E. coli cytoplasm. Biotechnology (N.Y.). 11:187–193.

Leland, P., L. Schultz, B. Kim, and R. Raines. 1998. Ribonuclease A variants with potent cytotoxic activity. Proc Natl Acad Sci USA. 95:10407–10412.

Madshus, I., and H. Stenmark. 1992. Entry of ADP-ribosylating toxins into cells. Curr Top Microbiol Immunol. 175:1–26.

Marasco, W. A., W. A. Haseltine, and S. Y. Chen. 1993. Design, intracellular expression, and activity of a human anti-human immunodeficiency virus type 1 gp 120 single-chain antibody. Proc. Natl. Acad. Sci USA. 90:7889–7893.

Mitra, A., and A. Gynheung. 1989. Three distinct regulatory elements comprise the upstream promoter of the nopaline synthase gene. Mol. Gen. Genet. 215:294–299.

Montanaro, L., S. Sperti, A. Mattioli, G. Testoni, and F. Stirpe. 1975. Inhibition by ricin of protein synthesis in vitro. Inhibition of the binding of elongation factor 2 and of adenosine diphosphate-ribosylated elongation factor 2 to ribosomes. Biochem J. 146:127–31.

Namba, S., K. Ling, C. Gonsalves, D. Gonsalves, and J. L. Slightom. 1991. Expression of the gene encoding the coat protein of cucumber mosaic virus (CMV) strain WL appears to provide protection to sugarbeet plants against infection by several different strains. Gene. 107:181–188.

Ni, M., D. Cui, J. Einstein, S. Narasimhulu, C. E. Vergara, and S. B. Gelvin. 1995. Strength and tissue specificity of chimeric promoters derived from octopine and nopaline synthase genes. Plant J. 7:661–676.

Owen, M., A. Gandecha, B. Cockburn, and G. Whitelam. 1992. Synthesis of a functional anti-phytochrome single-chain Fv protein in transgenic tobacco. Bio/Technology. 10:790–794.

Palukaitis, P., and M. J. Roossinck. 1996. Spontaneous change of a benign satellite RNA of cucumber mosaic virus to a pathogenic variant. Nature Biotechnology. 14:1264–1268.

Peters, L. L., and S. E. Lux. 1993. Ankyrins: structure and function in normal cells and hereditary spherocytes. Semin Hematol. 30:85–118.

Plückthun, A. 1991. Antibody engineering. Current Opirion in Biotechnology. 2:238–246.

Pluckthun, A., and P. Pack. 1997. New protein engineering approaches to multivalent and bispecific antibody fragments. Immunotechnology. 3:83–105.

Poljak, R. J. 1994. Production and structure of diabodies. Structure. 2:1121–3.

Rose, M., and G. Fink. 1987. KAR1, a gene required for function of both intranuclear and extranuclear microtubules in yeast. Cell. 48:1047–1060.

Sanford, J. C., E. D. Wolf, and N. K. Allen. 1990. Method for transporting substances into living cells and apparatus therefore. Patent #4,945,050. Cornell Research Foundation Inc, Ithaca, N.Y.

Sangster, B. 1997. Identification of cytotoxic peptide as possible mechanism for neurotoxicity of HIV viral envelope and AIDS pathogenesis. Med Hypotheses. 48:463–8.

Schouten, A., J. Roosien, J. M. de Boer, A. Wilmink, M.-N. Rosso, D. Bosch, W. J. Stiekema, F. J. Gommers, J. Bakker, and A. Schots. 1997. Improving scFv antibody expression levels in the plant cytosol. FEBS letters. 415:235–241.

Silburn, K., D. McPhee, A. Maerz, P. Poumbourios, R. Whittaker, A. Kirkpatrick, W. Reilly, M. Manthey, and C. Curtain. 1998. Efficacy of fusion peptide homologs in blocking cell lysis and HIV-induced fusion. AIDS Res Hum Retroviruses. 14:385–392.

Smith, D., and K. Johnson. 1988. Single-step purification of polypeptides expressed in *Escherichia coli* as fusions with glutathione S-transferase. Gene. 67:31–40.

Spörlein, B., and H.-U. Koop. 1991. Lipofectin: direct gene transfer to higher plants using cationic liposomes. Theor. Appl. Genet. 83:1–5.

Tang, Y., N. Jiang, C. Parakh, and D. Hilvert. 1996. Selection of linkers for a catalytic single-chain antibody using phage display technology. J Biol Chem. 271:15682–6.

Taviadoraki, P., E. Benvenuto, S. Trinca, D. DeMartinis, and P. Galeffi. 1993. Transgenic plants expressing a functional scFv antibody are protected from virus attack. Nature. 366:469–472.

Tedder, T. F., and P. Engel. 1994. CD20: a regulator of cell-cycle progression of B lymphocytes. Immunol Today. 15:450–4.

Tumer, D. J., M. A. Ritter, and A. J. George. 1997. Importance of the linker in expression of single-chain Fv antibody fragments: optimisation of peptide sequence using phage display technology. J Immunol Methods. 205:43–54.

Turpen, T. H., A. M. Turpen, N. Weinzettl, M. H. Kumagai, and W. O. Dawson. 1993. Transfection of whole plants from wounds inoculated wtih *Agrobacterium tumefaciens* containing cDNA of Tobacco Mosaic Virus. J. Virol. Meth. 42:227–240.

von Heiine, G. 1985. Signal sequences. The limits of variation. J Mol Biol 1985. 184:99–105.

Voss, A., M. Niersbach, R. Hain, H. J. Hirsch, Y. C. Liao, F. Kreuzaler, and R. Fischer. 1995. Reduced virus infectivity in N. tabacum secreting a TMV-specific full size antibody. Mol. Breeding, 1:39–50.

White, F. F. 1992. Vectors for gene transfer in higher plants. In Transgenic Plants. Vol. 1. Academic Press. 15–47.

Wilson, T. M. A. 1993. Strategies to protect crop plants against viruses: Pathogen-derived resistance blossoms. Proc. Natl. Acad. Sci. USA. 90:3134–3141.

Winter, G., A. D. Griffiths, R. E. Hawkins, and H. R. Hoogenboom. 1994. Making antibodies by phage display technology. Annu Rev Immunol. 12:433–55.

Winter, G., and C. Milstein. 1991. Man made antibodies. Nature. 349:293–299.

Wright, M. D., and M. G. Tomlinson. 1994. The ins and outs of the transmembrane 4 superfamily. Immunol Today. 15:588–94.

Zimmermann, S., S. Schillberg, Y. C. Liao, and R. Fischer. 1998. Intracellular expression of a TMV-specific single chain Fv fragment leads to improved virus resistance in Nicotiana tabacum. Molecular Breeding. 4:369–379.

What is claimed is:

1. A fusion protein comprising
   (a) at least one binding domain comprising an antibody or binding site thereof that specifically recognizes an epitope of a plant pathogen; and
   (b) a membrane localization sequence and/or motif that leads to membrane anchoring,
   wherein said membrane localization sequence and/or motif is C-terminal to said binding domain.

2. The fusion protein of claim 1 further comprising at least one domain comprising a protein or peptide sequence that is toxic to the pathogen or detrimental to its replication, transmission or life cycle.

3. The fusion protein of claim 2 wherein the toxic activity of the protein or peptide sequence is activated by the presence of the pathogen, a component thereof or a component of a host cell.

4. The fusion protein of claim 3 wherein the toxic activity of the protein or peptide sequence is activated by a pathogen specific or host cell protease.

5. The fusion protein of claim 1 wherein said binding domain comprises an antibody, a T-cell receptor, a pathogen specific receptor, a peptide specific for an epitope of a pathogen, or at least the binding site of any one of those.

6. The fusion protein of claim 5 wherein said antibody or binding site thereof is a recombinant full-size antibody, dimeric secretory IgA antibody, multimeric IgM antibody, $F(ab')_2$-fragment, Fab-fragment, Fv-fragment, single chain Fv antibody (scFv), bispecific scFv, diabody, single domain antibody (dAb), minibody or molecular recognition unit (MRU), derived from hybridoma cells, synthetic, semi-synthetic, naïve and immunocompetent phage display or ribosome display libraries, or by the generation of fully synthetic designer antibodies.

7. The fusion protein of claim 1 comprising at least two binding domains for the same or different epitope(s).

8. The fusion protein of claim 7 wherein said epitopes are from the same or different pathogen(s).

9. The fusion protein of claim 2 wherein the toxin is an enzyme or a viral structural or non-structural protein or a binding domain comprising an antibody or binding site thereof that specifically recognizes an epitope of a plant pathogen.

10. The fusion protein of claim 9 wherein said enzyme is chitinase or glucanase, glucose oxidase, superoxide dismutase, DNAse or RNAse or ribosomal-inactivating-protein ("RIP") or lipase or active fragments thereof either singly or in any combination(s).

11. The fusion protein of claim 1 wherein the pathogen is a virus, bacterium, mycoplasma, fungus, nematode or insect.

12. The fusion protein of claim 1 wherein at least one of said domains is fused to a C- or N-terminal carrier protein.

13. The fusion protein of claim 1 wherein at least one of said domains comprises a fluorophore.

14. A pathogenicide comprising the fusion protein of claim 1 or 2.

15. The fusion protein of claim 1, wherein said binding domain(s) and/or said further domain(s) are capable of self assembly in vivo.

16. The pathogenocide of claim 14 wherein the antibody or binding site thereof specifically recognizes a viral movement and/or replicase protein.

17. The pathogenicide of claim 16 which comprises an antibody.

18. A kit comprising the fusion protein of claim 1 or the pathogenocide of claim 14.

19. The fusion protein of claim 1 or 2, wherein the membrane localization sequence is proteolytically sensitive.

20. The fusion protein of claim 1 or 2, wherein the membrane localization sequence is a member of the immunoglobulin super family.

21. The fusion protein of claim 1 or 2, wherein the membrane localization sequence is human T cell receptor transmembrane domains, glyco-phosphatidyl inositol (GPI) anchors, KAR1, middle-T antigen, cytochrome b5 or syn1.

22. The fusion protein of claim 1 or 2, wherein the domains are linked by covalent or non-covalent bonds.

23. The fusion protein of claim 1, wherein further comprising a cellular targeting sequence.

24. The pathogenocide of claim 14, wherein said binding domain(s) and/or said further domain(s) are capable of self assembly in vivo.

25. A kit comprising the pathogenocide of claim 14.

* * * * *